(12) United States Patent
Itoi

(10) Patent No.: US 10,600,968 B2
(45) Date of Patent: Mar. 24, 2020

(54) AMINE COMPOUND AND ORGANIC ELECTROLUMINESCENCE DEVICE INCLUDING THE SAME

(71) Applicant: Samsung Display Co., Ltd., Yongin-si, Gyeonggi-do (KR)

(72) Inventor: Hiroaki Itoi, Yokohama (JP)

(73) Assignee: Samsung Display Co., Ltd., Yongin-si (KR)

( * ) Notice: Subject to any disclaimer, the term of this patent is extended or adjusted under 35 U.S.C. 154(b) by 252 days.

(21) Appl. No.: 15/863,720

(22) Filed: Jan. 5, 2018

(65) Prior Publication Data

US 2018/0287062 A1    Oct. 4, 2018

(30) Foreign Application Priority Data

Apr. 3, 2017    (KR) .................. 10-2017-0043118

(51) Int. Cl.
| | |
|---|---|
| *H01L 51/50* | (2006.01) |
| *H01L 51/00* | (2006.01) |
| *C07C 211/61* | (2006.01) |
| *C07D 213/74* | (2006.01) |
| *C07D 239/42* | (2006.01) |

(Continued)

(52) U.S. Cl.
CPC ......... *H01L 51/006* (2013.01); *C07C 211/61* (2013.01); *C07D 213/74* (2013.01); *C07D 239/42* (2013.01); *C07D 307/91* (2013.01); *C07D 333/76* (2013.01); *H01L 51/0058* (2013.01); *C07C 2602/10* (2017.05); *C07C 2603/18* (2017.05); *C07C 2603/94* (2017.05);

(Continued)

(58) Field of Classification Search
None
See application file for complete search history.

(56) References Cited

U.S. PATENT DOCUMENTS

| | | |
|---|---|---|
| 8,318,395 B2 | 11/2012 | Saitoh et al. |
| 9,595,681 B2 | 3/2017 | Mujica-Fernaud et al. |
| 2017/0186978 A1* | 6/2017 | Kim .................... H01L 51/0072 |

FOREIGN PATENT DOCUMENTS

| | | |
|---|---|---|
| JP | 2009-29726 A | 2/2009 |
| JP | 2009-267255 A | 11/2009 |

(Continued)

*Primary Examiner* — Gregory D Clark
(74) *Attorney, Agent, or Firm* — Lewis Roca Rothgerber Christie LLP

(57) ABSTRACT

An amine compound and an organic electroluminescence device including the same are provided. The amine compound according to an embodiment of the inventive concept is represented by Formula 1.

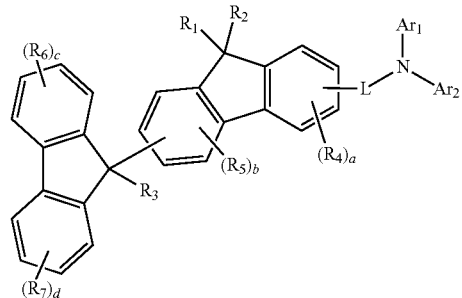

Formula 1

19 Claims, 1 Drawing Sheet

(51) Int. Cl.
*C07D 307/91* (2006.01)
*C07D 333/76* (2006.01)

(52) U.S. Cl.
CPC .... *H01L 51/5056* (2013.01); *H01L 2251/556* (2013.01)

(56) References Cited

FOREIGN PATENT DOCUMENTS

| | | |
|---|---|---|
| KR | 10-1069062 B1 | 9/2011 |
| KR | 10-2015-0034390 A | 4/2015 |
| KR | 10-2015-0036721 A | 4/2015 |
| WO | WO 2015/046955 A1 | 4/2015 |
| WO | WO 2015/084114 A1 | 6/2015 |

* cited by examiner

AMINE COMPOUND AND ORGANIC ELECTROLUMINESCENCE DEVICE INCLUDING THE SAME

CROSS-REFERENCE TO RELATED APPLICATION

This patent application claims priority to and the benefit of Korean Patent Application No. 10-2017-0043118, filed in the Korean Intellectual Property Office on Apr. 3, 2017, the entire content of which is incorporated herein by reference.

BACKGROUND

1. Field

The present disclosure herein relates to an amine compound and an organic electroluminescence device including the same.

2. Description of the Related Art

As an image display device, an organic electroluminescence device has been actively developed. The organic electroluminescence display device is different from a liquid crystal display device and the like, and is a self-emission display device that realizes display by recombining holes and electrons injected from a first electrode and a second electrode in a light emitting layer to emit light from a light emitting material, which is an organic compound included in the light emitting layer.

As an example of the organic electroluminescence device, a related art organic device includes a first electrode, a hole transfer layer arranged on the first electrode, a light emitting layer arranged on the hole transfer layer, an electron transfer layer arranged on the light emitting layer, and a second electrode arranged on the electron transfer layer. Holes are injected from the first electrode, and the injected holes move to the hole transfer layer and are injected into the light emitting layer. On the other hand, electrons are injected from the second electrode, and the injected electrons move to the electron transfer layer and are injected into the light emitting layer. Excitons are generated in the light emitting layer by recombination of the holes and electrons injected into the light emitting layer. The organic electroluminescence device emits light when the excitons fall back to the ground state. Also, the organic electroluminescence device is not limited to the structure described above, and several suitable changes are possible. In applying the organic electroluminescence device to a display device, a lower driving voltage and long lifetime of the organic electroluminescence devices are required.

SUMMARY

An aspect according to one or more embodiments of the present disclosure is directed toward an amine compound capable of being utilized in an organic electroluminescence device to provide a low driving voltage and an improved lifetime.

Another aspect according to one or more embodiments of the present disclosure is directed toward an organic electroluminescence device having a low driving voltage and an improved lifetime.

According to an embodiment of the inventive concept, an amine compound is represented by Formula 1.

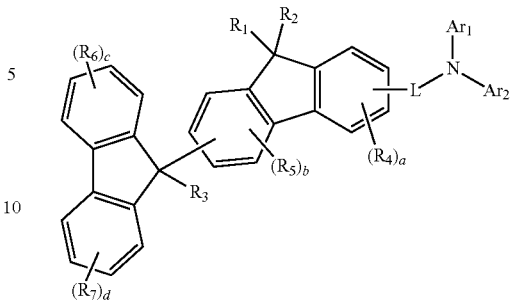

Formula 1

In Formula 1, $Ar_1$ and $Ar_2$ are each independently a substituted or unsubstituted aryl group having 6 to 30 carbon atoms for forming a ring, or a substituted or unsubstituted heteroaryl group having 2 to 30 carbon atoms for forming a ring; L is a direct linkage, a substituted or unsubstituted arylene group having 6 to 30 carbon atoms for forming a ring, or a substituted or unsubstituted heteroarylene group having 2 to 30 carbon atoms for forming a ring; $R_1$ to $R_7$ are each independently hydrogen, deuterium, a halogen atom, a substituted or unsubstituted alkyl group having 1 to 20 carbon atoms, a substituted or unsubstituted aryl group having 6 to 30 carbon atoms, for forming a ring, or a substituted or unsubstituted cyclic heteroaryl group having 2 to 30 carbon atoms for forming a ring; $R_1$ and $R_2$ may combine with each other to form a ring; a and b are each independently an integer of 0 to 3; and c and d are each independently an integer of 0 to 4.

The amine compound represented by Formula 1 may be represented by Formula 2-1.

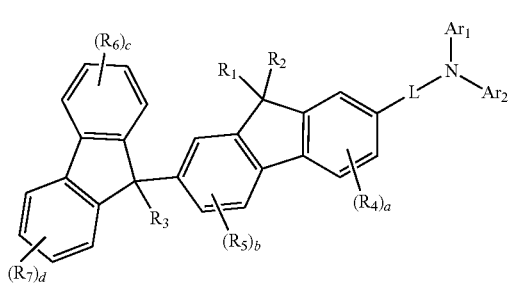

Formula 2-1

In Formula 2-1, $Ar_1$, $Ar_2$, L, $R_1$ to $R_7$, and a to d are the same as defined above.

The amine compound represented by Formula 1 may be represented by Formula 2-2.

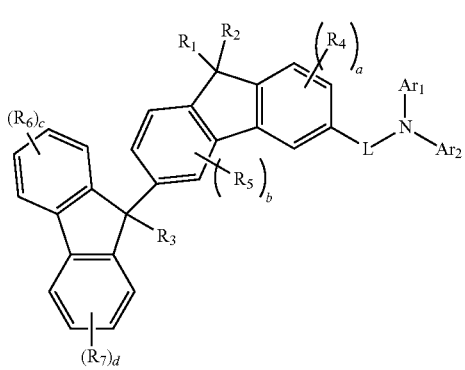

Formula 2-2

In Formula 2-2, $Ar_1$, $Ar_2$, L, $R_1$ to $R_7$, and a to d are the same as defined above.

$Ar_1$ and $Ar_2$ may be each independently a substituted or unsubstituted phenyl group, a substituted or unsubstituted naphthyl group, a substituted or unsubstituted dibenzofuranyl group, or a substituted or unsubstituted dibenzothiophenyl group. $R_1$ to $R_2$ may be each independently a methyl group, a substituted or unsubstituted phenyl group, or combine with each other to form a ring.

The amine compound represented by Formula 1 may be represented by any one of Formulae 3-1 to 3-3.

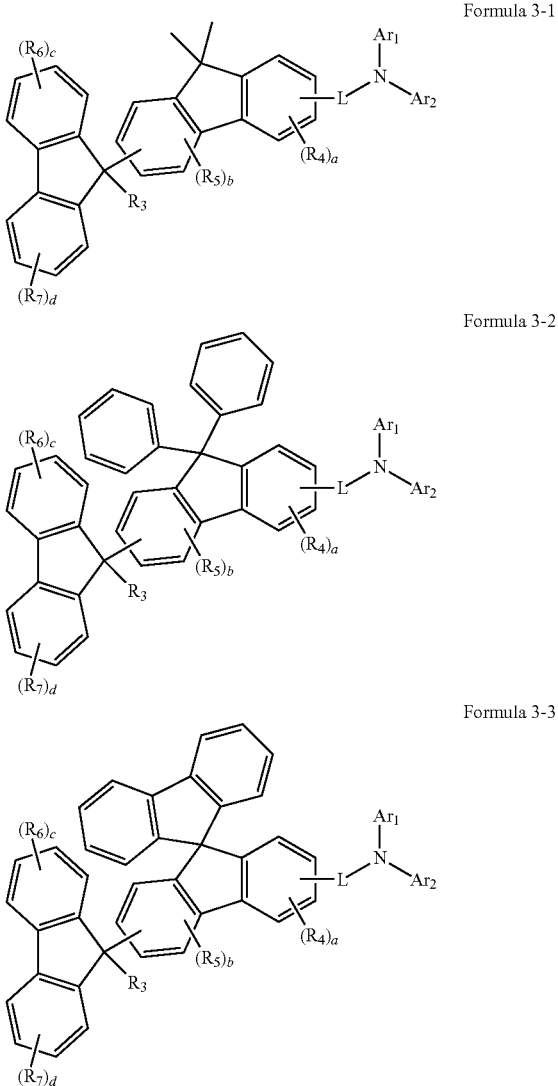

Formula 3-1

Formula 3-2

Formula 3-3

In Formulae 3-1 to 3-3, $Ar_1$, $Ar_2$, L, $R_3$ to $R_7$, and a to d are the same as defined above.

According to an embodiment of the inventive concept, an organic electroluminescence device includes a first electrode; a hole transfer region on the first electrode; a light emitting later on the hole transfer layer; an electron transfer region on the light emitting layer; and a second electrode on the electron transfer layer. The hole transfer region may include an amine compound according to an embodiment of the inventive concept.

The hole transfer region may include a hole injection layer on the first electrode and a hole transfer layer on the hole injection layer, and the hole transfer layer may include the amine compound represented by Formula 1.

BRIEF DESCRIPTION OF THE DRAWINGS

The above and other aspects, features and other enhancements of the present disclosure will be more clearly understood from the following detailed description taken in conjunction with the accompanying drawings, in which.

DETAILED DESCRIPTION

Figure 1:
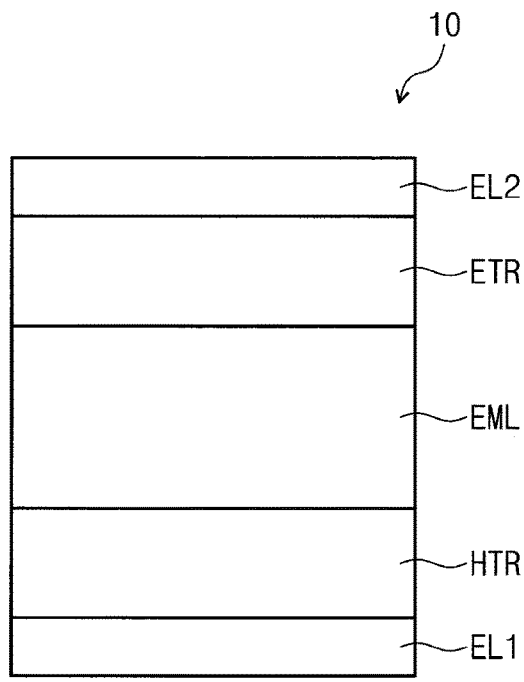
FIG. 1 is a cross sectional view schematically illustrating an organic electroluminescence device according to an embodiment of the inventive concept.

The above and other objects, features, and enhancements of the present invention will be more readily understood with reference to the accompanying drawings and the following exemplary embodiments. The present disclosure may, however, be embodied in many different forms and should not be construed as being limited to the embodiments set forth herein. Rather, these embodiments are provided so that this disclosure will be thorough and complete, and will fully convey the concept of the invention to those skilled in the art.

Like reference numerals have been used for like elements in describing each drawing. In the accompanying drawings, the dimensions of structures are exaggerated for clarity of illustration. Although the terms first, second, etc., may be used herein to describe various elements, these elements should not be limited by these terms. These terms are only used to distinguish one element from another element. For example, without departing from the teachings of the present disclosure, a first element could be termed a second element, and similarly, a second element could also be termed a first element. The singular forms are intended to include the plural forms as well, unless the context clearly indicates otherwise.

It will be understood that the terms "includes" and/or "including", when used in this specification, specify the presence of stated features, integers, steps, operations, elements, and/or components, but do not preclude the presence or addition of one or more other features, integers, steps, operations, elements, and/or components. Also, when a portion of a layer, film, region, plate, etc., is referred to as being "on" or "under" another part, it can be directly on or directly under the other part, or intervening layers, films, regions, plates, etc., may also be present.

In the present specification, the term "substituted" may refer to a compound in which at least one hydrogen atom is substituted with one or more substituents selected from deuterium, a halogen atom, a cyano group, a nitro group, an amino group, a silyl group, a boron group, an arylamine group, a phosphine oxide group, a phosphine sulfide group, an alkyl group, an alkenyl group, an aryl group and a heterocyclic group. Also, each of the exemplified substituents may be substituted or unsubstituted. For example, a biphenyl group may be construed as an aryl group, or a phenyl group substituted with a phenyl group.

In the present specification, the term "combine with a neighboring group to form a ring" may refer to the combination of neighboring groups with each other to form a substituted or unsubstituted hydrocarbon ring, or a substituted or unsubstituted heterocyclic group. The hydrocarbon ring may include an aliphatic hydrocarbon ring and/or an aromatic hydrocarbon ring. The heterocyclic group may include an aliphatic heterocyclic group and/or an aromatic heterocyclic group. The hydrocarbon ring and the heterocyclic group may be monocyclic or polycyclic. Furthermore, the ring formed by combining neighboring groups with each other may be connected to another ring to form a spiro structure.

In the present specification, the term "an adjacent group" to a first substituent may refer a substituent substituting an atom directly linked to an atom substituted with the corresponding first substituent (e.g., two substituents for two directly linked neighboring atoms are referred to as an adjacent group to each other); another substituent substituted with an atom substituted with the corresponding first substituent (e.g., two substituents, both linked to the same atom, are referred to as an adjacent group to each other); or a substituent most closely positioned sterically to the corresponding first substituent. For example, two methyl groups in 1, 2-dimethylbenzen may be construed as "an adjacent group" to each other, and two ethyl groups in 1,1-diethyl-cyclopentene may be construed as "an adjacent group" to each other.

In the present specification, the term "a direct linkage" may refer to a single bond.

In the present specification, examples of the halogen atom are a fluorine atom, a chlorine atom, a bromine atom and/or an iodine atom.

In the present specification, the alkyl group may be linear, branched, or cyclic. The number of carbon atoms of the alkyl group may be 1 to 30, 1 to 20, 1 to 15, 1 to 10, or 1 to 6. Non-limiting examples of the alkyl group may include a methyl group, an ethyl group, an n-propyl group, an isopropyl group, an n-butyl group, an s-butyl group, a t-butyl group, an i-butyl group, a 2-ethyl butyl group, a 3, 3-dimethyl butyl group, an n-pentyl group, an i-pentyl group, a neopentyl group, a t-pentyl group, a cyclopentyl group, a 1-methylpentyl group, a 3-methylpentyl group, a 2-ethylpentyl group, a 4-methyl-2penthyl group, an n-hexyl group, a 1-methylhexyl group, a 2-ethylhexyl group, a 2-butylhexyl group, a cyclohexyl group, a 4-methylcyclrohexyl group, a 4-t-butylcyclrohexyl group, an n-heptyl group, a 1-methylheptyl group, a 2, 2-dimethylheptyl group, a 3,7-dimethyloctyl group, a cyclooctyl group, an n-nonyl group, an n-decyl group, an adamantyl group, a 2-ethyldecyl group, a 2-butyldecyl group, a 2-hexyldecyl group, a 2-octyldecyl group, an n-undecyl group, an n-dodecyl group, an ethyldodecyl group, a butyldodecyl group, a hexyldodecyl group, an octyldodecyl group, an n-tridecyl group, an n-tetradecyl group, a pentadecyl group, an n-hexadecyl group, a 2-ethylhexadecyl group, a 2-butylhexadecyl group, a 2-hexylhexadecyl group, a 2-octylhexadecyl group, an n-heptadecyl group, an n-octadecyl group, an n-nonadecyl, an n-eicosyl group, a 2-ethylicosyl group, a 2-butyleicosyl group, a 2-hexyleicosyl group, a 2-octyl eicosyl group, an n-henicosyl group, an n-docosyl group, an n-tricosyl group, an n-tetracosyl group, an n-pentacosyl group, an n-hexacosyl group, an n-heptacosyl group, an n-octacosyl group, an n-nonacosyl group, an n-triacontyl group, or the like.

In the present specification, the term "aryl group" may refer to any functional group or substituent derived from the aromatic hydrocarbon ring. The aryl group may be a monocyclic aryl or a polycyclic aryl. The ring-forming carbon number of the aryl group may be 6 to 30, 6 to 20, or 6 to 15. Non-limiting examples of the aryl group may include a phenyl group, a naphthyl group, a fluorenyl group, an anthracenyl group, a phenanthryl group, a biphenyl group, a terphenyl group, a quaterphenyl group, a quinquephenyl group, a sexyphenyl group, a triphenylene group, a pyrenyl group, a benzofluoranthenyl group, a chrysenyl group, etc.

In the present specification, the term "fluorenyl group" may refer to an unsubstituted or a substituted fluorenyl group, and two substituents may combine with each other to form the spiro structure.

In the present specification, the term "heteroaryl group" may refer to a heteroaryl group including at least one of O, N, P, S or Si as a ring forming hetero atom. The heteroaryl group may be a monocyclic heteroaryl group or a polycyclic heteroaryl. The ring-forming carbon number of the heteroaryl group may be 2 to 30, or 2 to 20. Non-limiting examples of the heteroaryl group may include a thiophenyl group, a furanyl group, a pyrrolyl group, an imidazolyl group, a thiazolyl group, an oxazolyl group, an oxadiazolyl group, a triazolyl group, a pyridyl group, a bipyridyl group, a pyrimidyl group, a triazinyl group, a triazolyl group, an acridyl groups, a pyridazinyl group, a pyrazinyl group, a quinolinyl group, a quinazolinyl group, a quinoxalinyl group, a phenoxazyl group, a phthalazinyl group, a pyrido pyrimidinyl group, a pyrido pyrazinyl group, a pyrazino pyrazinyl group, an isoquinolinyl group, an indolyl group, a carbazolyl group, an N-arylcarbazolyl group, an N-heteroarylcarbazolyl group, an N-alkylcarbazolyl group, a benzoxazolyl group, a benzoimidazolyl group, a benzothiazolyl group, a benzocarbazolyl group, a benzothiophenyl group, a dibenzothiophenyl group, a thienothiophenyl group, a benzofuranyl group, a phenanthrolinyl, a thiazolyl group, an isoxazolyl group, an oxadiazolyl group, a thiadiazolyl group, a benzothiazolyl group, a phenothiazinyl group, a dibenzosilolyl group, a dibenzofuranyl group, etc.

In the present specification, the previous description for the aryl group may be applied to the term "arylene group", except that the arylene group is a divalent group. In the present specification, the previous description for the heteroarylene group may be applied to the term "heteroarylene group", except that the heteroarylene group is a divalent group.

In the present specification, the term "silyl group" may refer to an alkylsilyl group and/or an arylsilyl group. Non-limiting examples of the silyl group may include a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group, etc.

In the present specification, the term "boron group" may include an alkyl boron group and/or an aryl boron group. Non-limiting examples of the boron group may include a trimethylboron group, a triethylboron group, a t-butyldimethylboron group, a triphenylboron group, a diphenylboron group, and a phenylboron group.

In the present specification, the alkenyl group may be linear or branched. The number of carbon atoms is not particularly limited, and may be 2 to 30, 2 to 20, or 2 to 10. Non-limiting examples of the alkenyl group may include a vinyl group, a 1-butenyl group, a 1-pentenyl group, a 1,3-butadienyl aryl group, a styrenyl group and a styrylvinyl group.

In the present specification, the number of carbon atoms of the amine group is not particularly limited, and may be 1 to 30. The amine group may include an alkyl amine group and/or an aryl amine group. Non-limiting examples of the amine group may include a methylamine group, a dimethylamine group, a phenylamine group, a diphenylamine group, a naphthylamine group, a 9-methyl-anthracenylamine group, a triphenylamine group, etc.

Hereinafter, the amine compound according to an embodiment of the inventive concept will be described. The amine compound according to an embodiment of the inventive concept may be a monoamine compound.

The amine compound according to an embodiment of the inventive concept is presented by Formula 1.

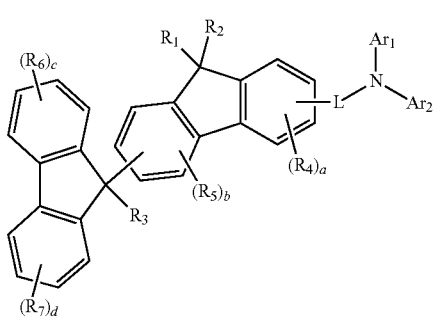

Formula 1

In Formula 1, $Ar_1$ and $Ar_2$ are each independently a substituted or unsubstituted aryl group having 6 to 30 carbon atoms for forming a ring, or a substituted or unsubstituted heteroaryl group having 2 to 30 carbon atoms for forming a ring. For example, $Ar_1$ and $Ar_2$ may be each independently a substituted or unsubstituted aryl group having 6 to 20 carbon atoms for forming a ring, or a substituted or unsubstituted heteroaryl group having 2 to 20 carbon atoms for forming a ring. For example, $Ar_1$ and $Ar_2$ may be each independently a substituted or unsubstituted phenyl group, a substituted or unsubstituted biphenyl group, or a substituted or unsubstituted naphthyl group. For example, $Ar_1$ and $Ar_2$ may be each independently a substituted or unsubstituted dibenzofuran group, or a substituted or unsubstituted dibenzothiophene group. $Ar_1$ and $Ar_2$ may be the same as or different from each other. For example, $Ar_1$ and $Ar_2$ may be a substituted or unsubstituted biphenyl group, and may be identically to each other. Alternatively, $Ar_1$ may be an unsubstituted phenyl group, and $Ar_2$ may be a phenyl group substituted with a naphthyl group.

L is a direct linkage, a substituted or unsubstituted arylene group having 6 to 30 carbon atoms for forming a ring, or a substituted or unsubstituted heteroarylene group having 2 to 30 carbon atoms for forming a ring. For example, L may be a direct linkage, a substituted or unsubstituted arylene group having 6 to 15 carbon atoms for forming a ring, or a substituted or unsubstituted heteroarylene group having 2 to 15 carbon atoms for forming a ring. For example, L may be a direct linkage, a substituted or unsubstituted phenylene group, or a substituted or unsubstituted naphthylene group. For example, L may be a heteroarylene group including nitrogen (N). For example, L may be a substituted or unsubstituted pyridylene group, or a substituted or unsubstituted pyrimidylene group.

$R_1$ to $R_7$ are each independently hydrogen, deuterium, a halogen atom, a substituted or unsubstituted alkyl group having 1 to 20 carbon atoms, a substituted or unsubstituted aryl group having 6 to 30 carbon atoms for forming a ring, or a substituted or unsubstituted heteroaryl group having 2 to 30 carbon atoms for forming a ring. For example, $R_1$ to $R_7$ may be each independently hydrogen, deuterium, a substituted or unsubstituted methyl group, or a substituted or unsubstituted phenyl group. $R_3$ may be a substituted or unsubstituted methyl group, or a substituted or unsubstituted phenyl group.

$R_1$ and $R_2$ may combine with each other to form a ring. For example, $R_1$ and $R_2$ may be each a substituted or unsubstituted phenyl group, and $R_1$ and $R_2$ may combine with each other to form a ring. For example, $R_1$ and $R_2$ are each independently a substituted or unsubstituted phenyl group, and when $R_1$ and $R_2$ combine with each other to form a ring, the fluorenyl group connected to the amine group through L may be a spirobifluorenyl group.

$R_4$ to $R_7$ may not combine with a neighboring group to form a ring. Specifically, the compound represented by Formula 1 excludes the case where the bifluorenyl group are substituted with $R_4$ to $R_7$ and $R_4$ to $R_7$ combine with neighboring groups to form a ring. $R_4$ to $R_7$ may not combine with neighboring groups to form an aromatic hydrocarbon ring or an aromatic heterocyclic ring. Accordingly, the compound represented by Formula 1 may not include fluorene derivatives such as a benzofluorenyl group or a benzofluorenothiophenyl group.

a and b are each independently an integer of 0 to 3. When a is 0, the amine compound represented by Formula 1 is not substituted with $R_4$. When b is 0, the amine compound represented by Formula 1 is not substituted with $R_5$. When a is an integer of 2 or more, a plurality of $R_4$s may be the same as or different from each other. When b is an integer of 2 or more, a plurality of $R_5$s may be the same as or different from each other.

c is an integer of 0 to 4. When c is 0, the amine compound represented by Formula 1 is not substituted with $R_6$. When c is an integer of 2 or more, a plurality of $R_6$s may be the same as or different from each other. When d is 0, the amine compound represented by Formula 1 is not substituted with $R_7$. When d is an integer of 2 or more, a plurality of $R_7$s may be the same as or different from each other.

The amine compound represented by Formula 1 may be represented by Formula 2-1 or Formula 2-2.

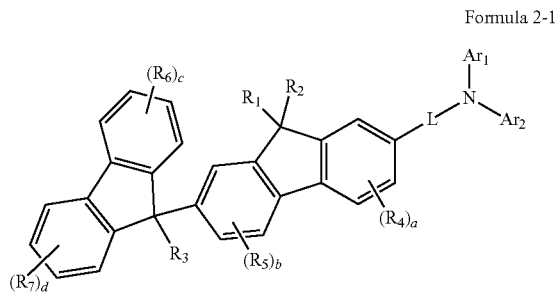

Formula 2-1

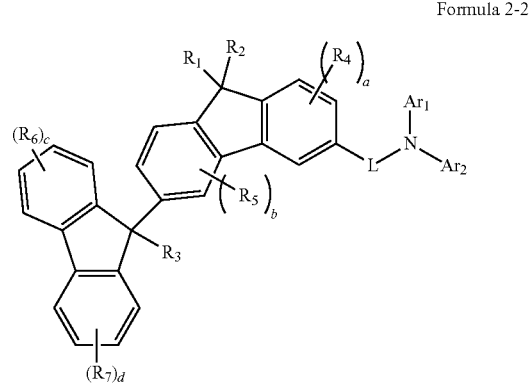

Formula 2-2

In Formulae 2-1 and 2-2, $Ar_1$, $Ar_2$, L, $R_1$ to $R_7$, and a to d are the same as defined above in association with Formula 1.

In the amine compound according to an embodiment of the inventive concept, the carbon position at which the amine group is linked by a linker at one (e.g., a first) fluorenyl group and the carbon position at which another (e.g., a second) fluorenyl group is substituted (e.g., a second fluorenyl group is substituted into the first fluorenyl group) may be symmetrically positioned. For example, as in Formula 2-1, the amine compound according to an embodiment of the inventive concept may have the amine group linked by the linker at No. 2 carbon position of one (e.g., the first) fluorenyl group, and (e.g., the first fluorenyl group is further) substituted with another fluorenyl group at No. 7 carbon position. In addition, as in Formula 2-2, the compound of an embodiment of the inventive concept may have the amine group linked by the linker at No. 3 carbon position of one (e.g., the first) fluorenyl group, and (e.g., the first fluorenyl group is further) substituted with another fluorenyl group at No. 8 carbon position.

The amine compound represented Formula 1 may be represented by one of Formulae 3-1 to 3-3.

In Formulae 3-1 to 3-3, $Ar_1$, $Ar_2$, L, $R_3$ to $R_7$, and a to d are the same as defined above in association with Formula 1.

When the amine compound according to an embodiment of the inventive concept is represented by Formula 3-1, $R_1$ and $R_2$ in Formula 1 may be each an unsubstituted methyl group. When the amine compound according to an embodiment of the inventive concept is represented by Formula 3-2, $R_1$ and $R_2$ in Formula 1 may be each an unsubstituted phenyl group. When the amine compound according to an embodiment of the inventive concept is represented by Formula 3-3, $R_1$ and $R_2$ in Formula 1 may be each an unsubstituted phenyl group, and may combine with each other to form a ring.

The amine compound represented by Formula 1 may be any one selected from the compounds represented by the Compound Group 1.

Compound Group 1

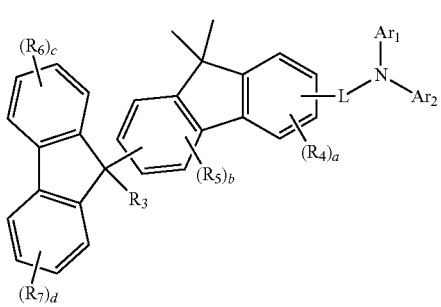

Formula 3-1

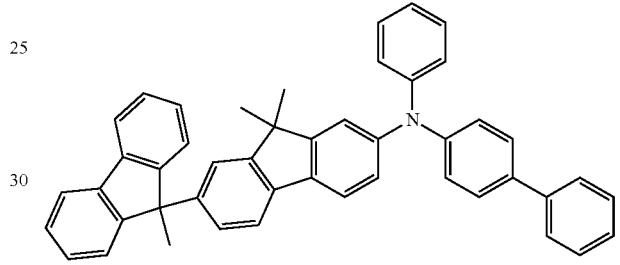

1

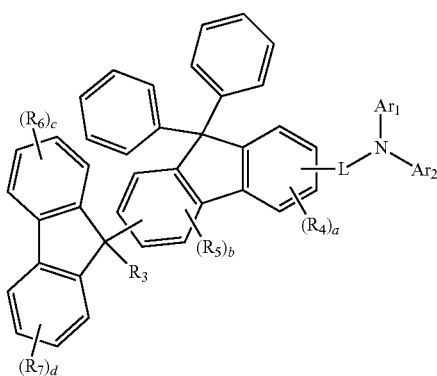

Formula 3-2

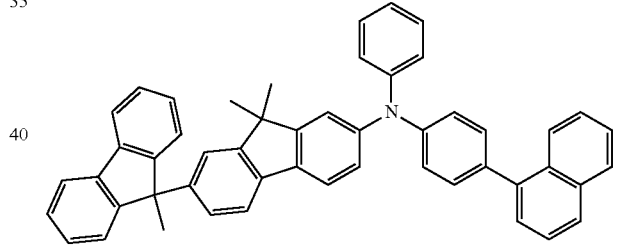

2

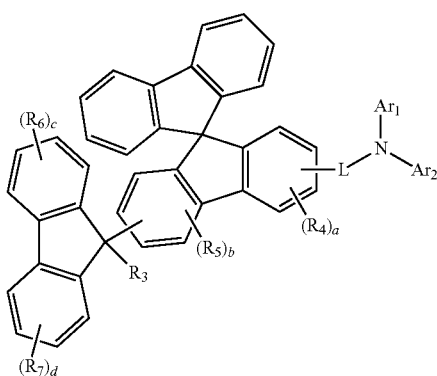

Formula 3-3

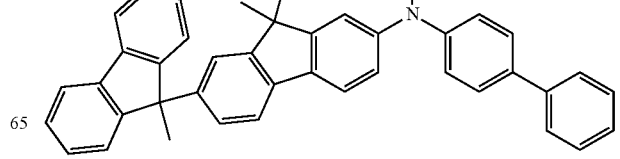

3

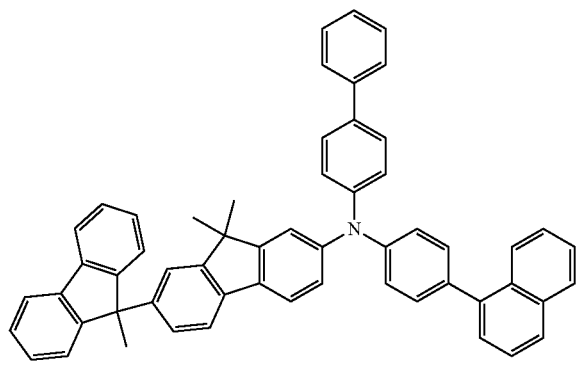
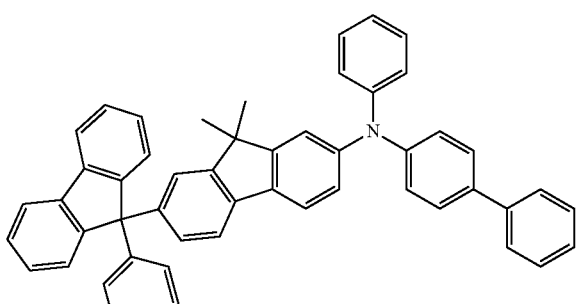

13
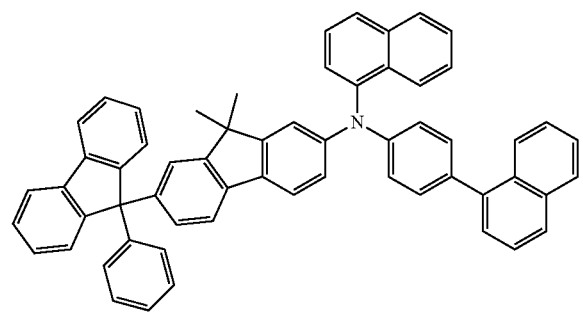
14
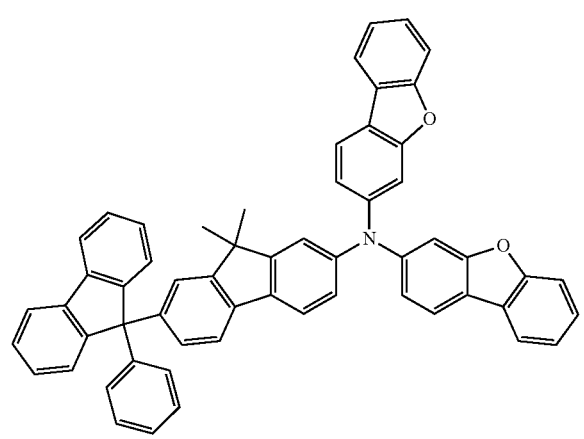
15
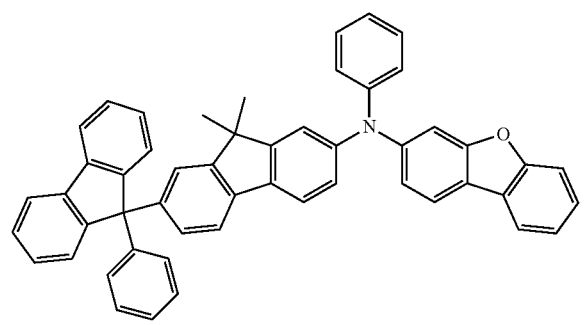
16
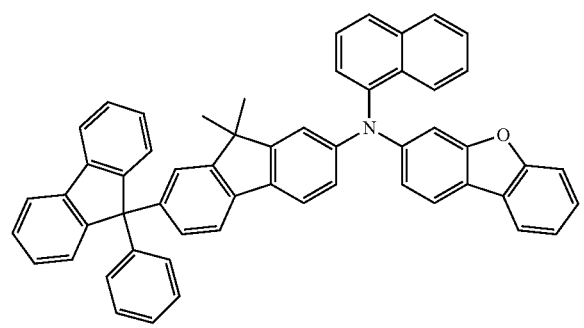
17
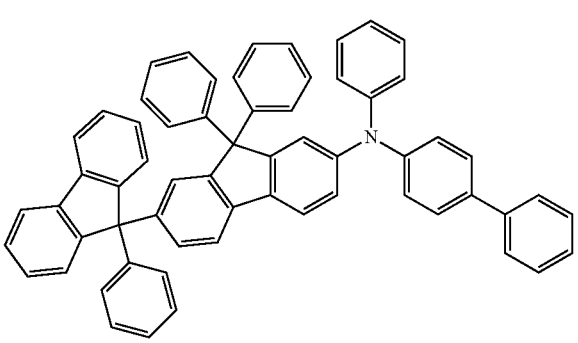
18
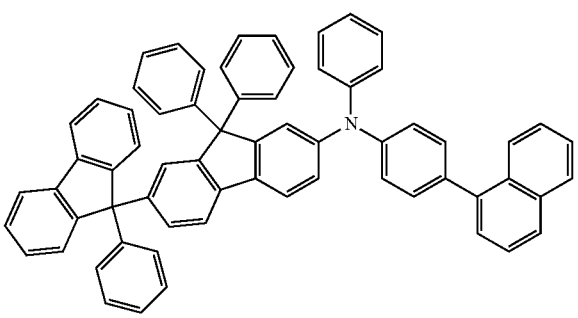
19
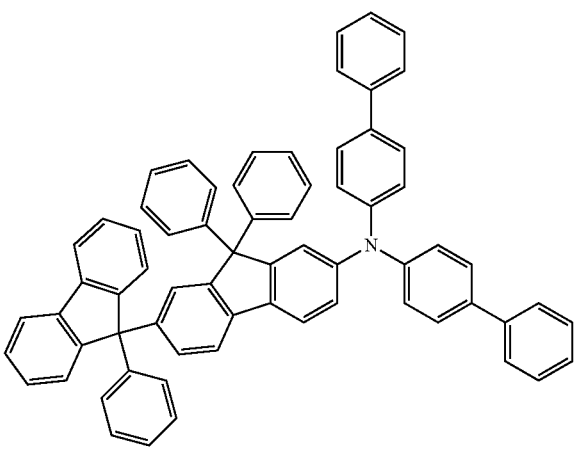
20
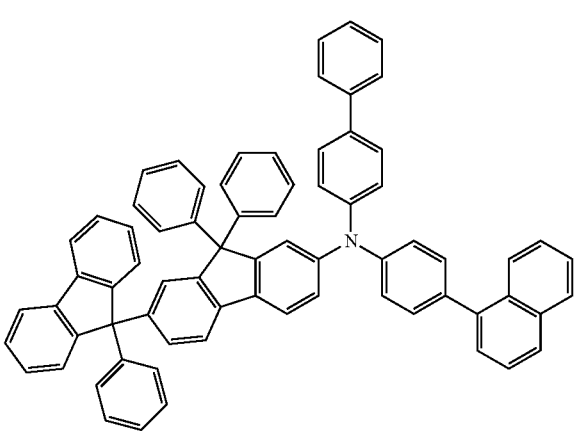

21
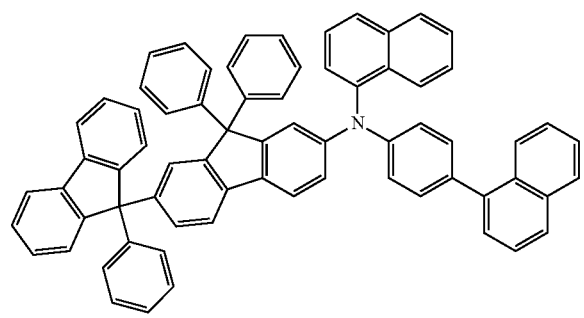
22
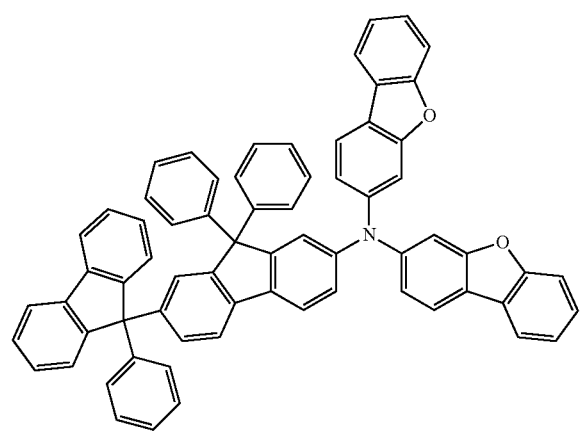
23
24
25
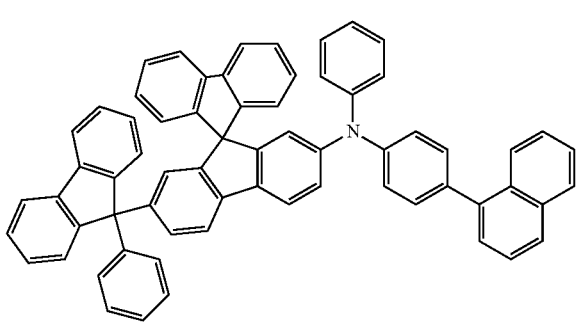
26
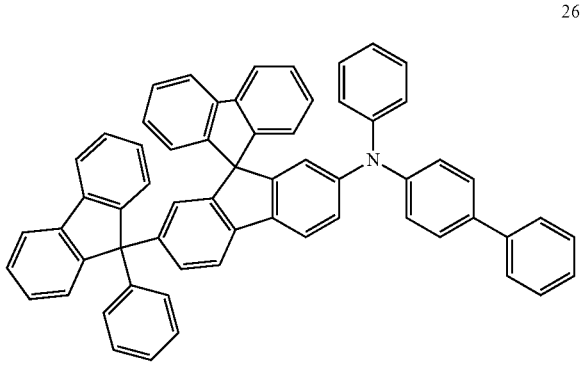
27
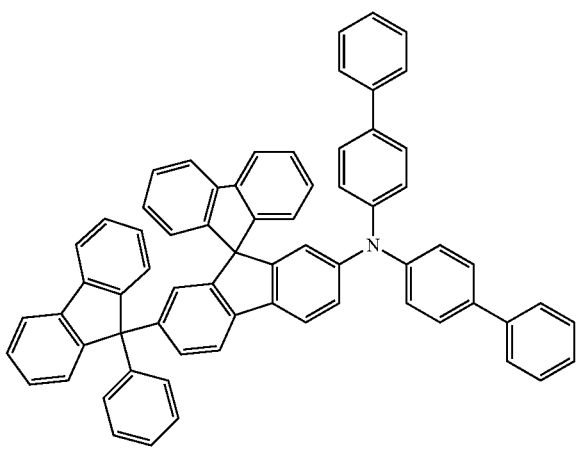
28
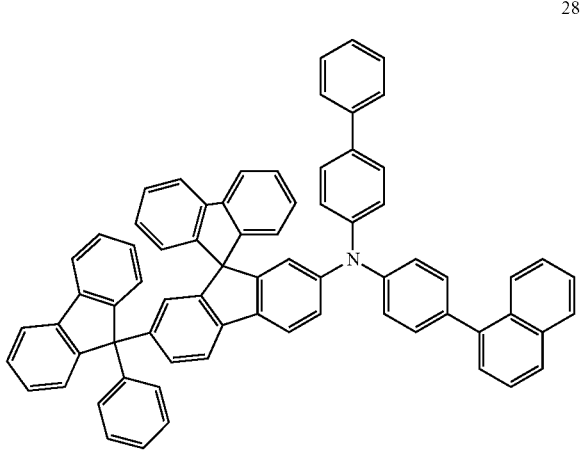
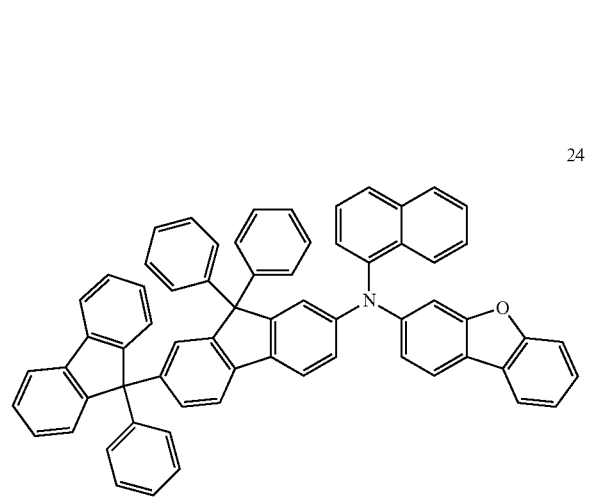

29
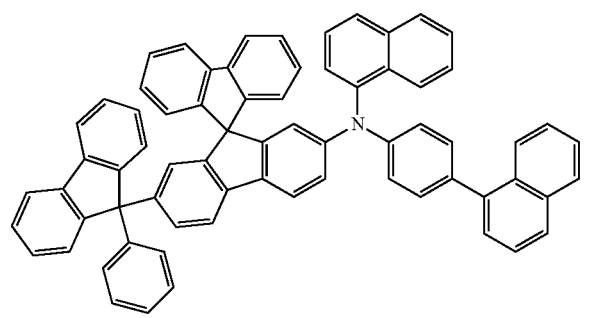
30
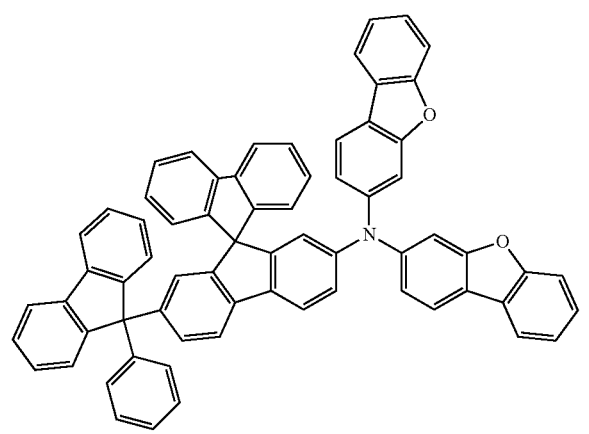
31
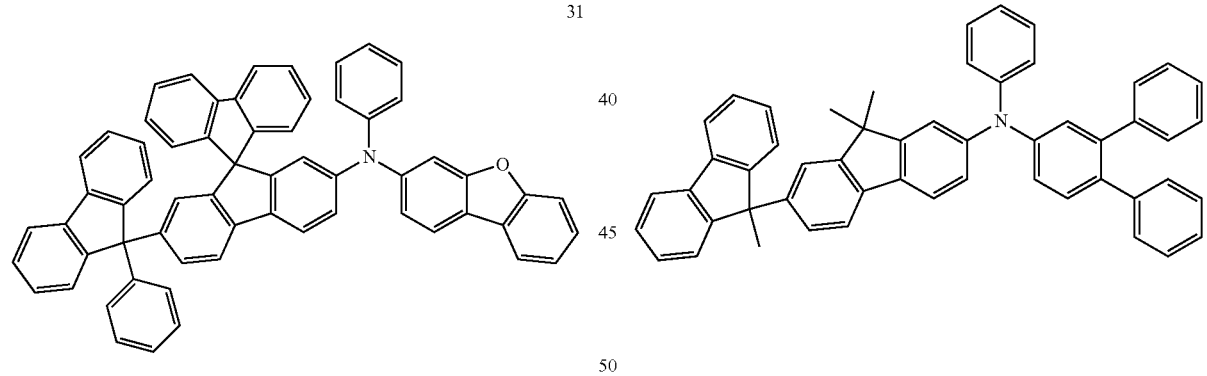
32
33
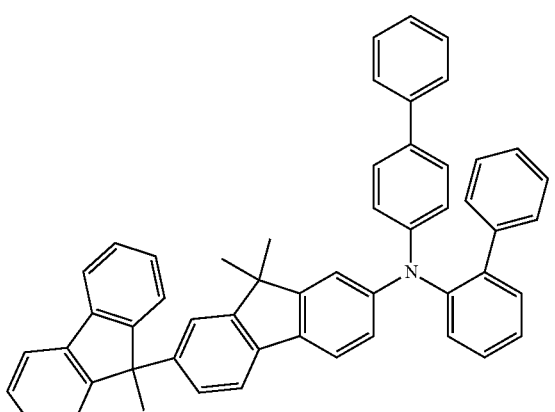
34
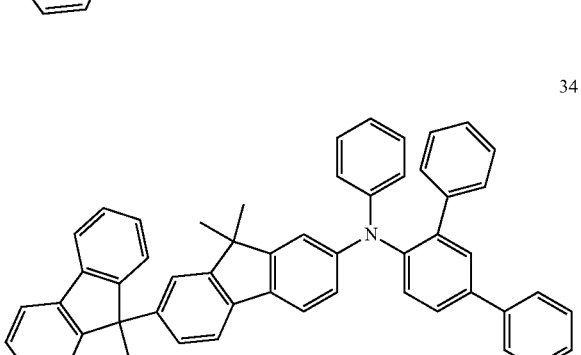
35
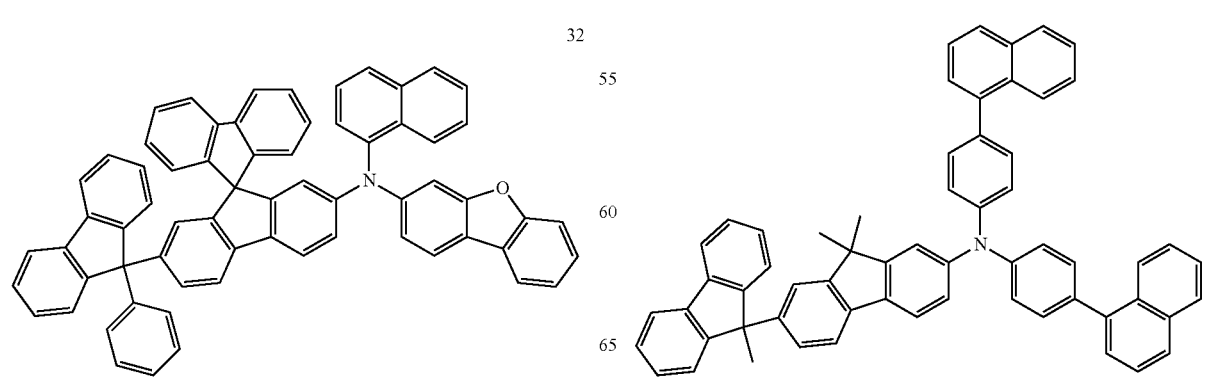
36

37
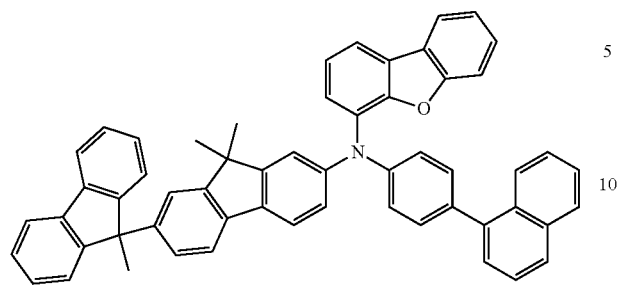
38
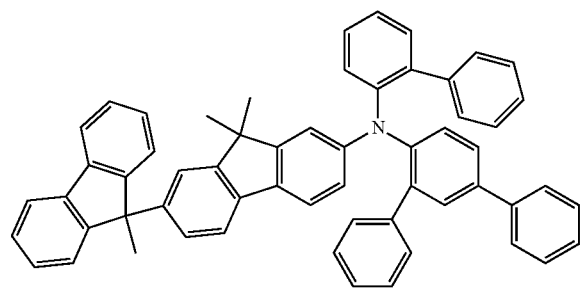
39
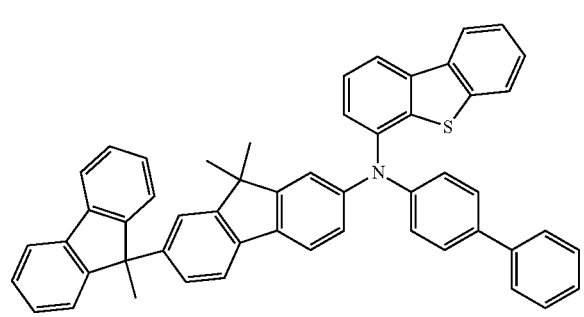
40
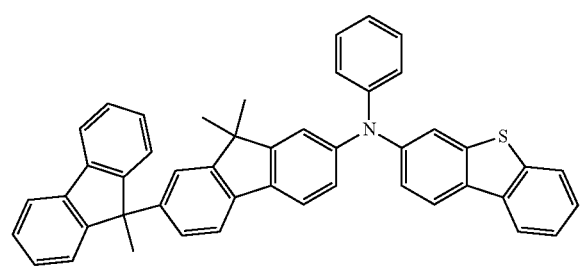
41
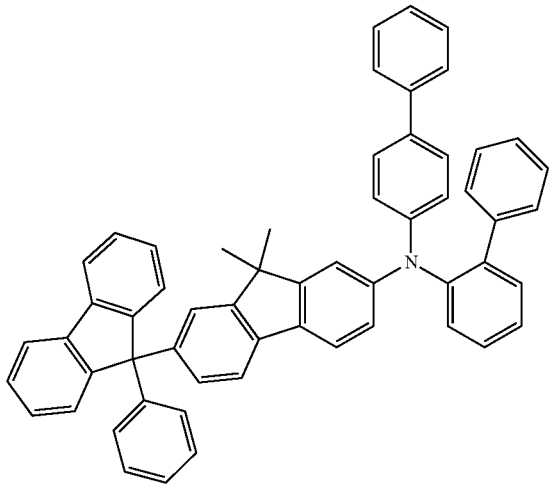
42
43
44
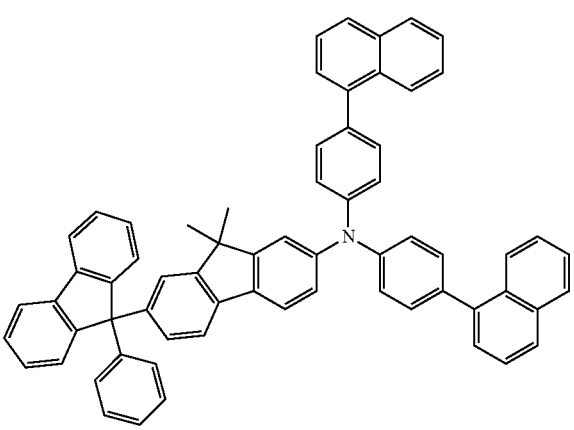

45
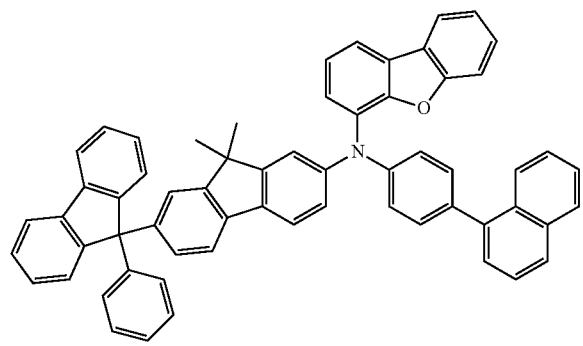
46
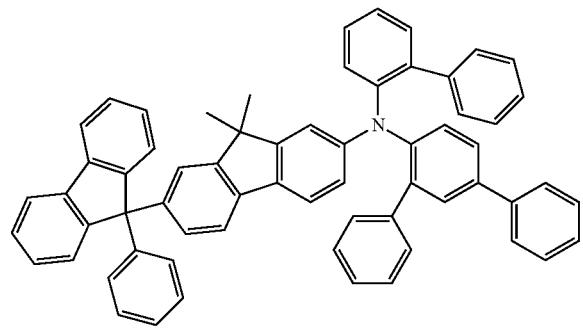
47
49
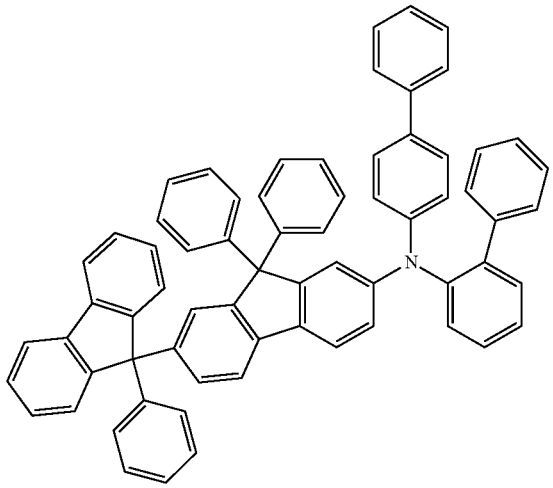
50
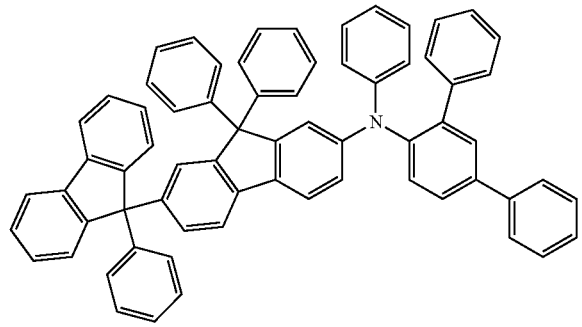
51
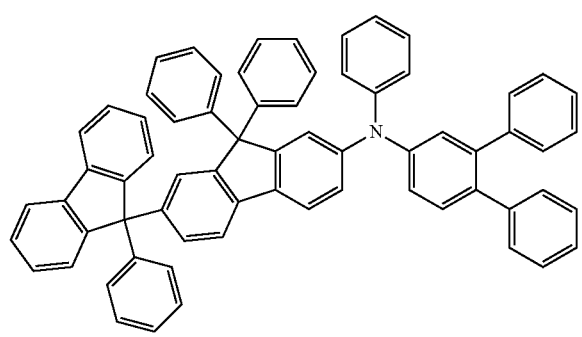
48
52
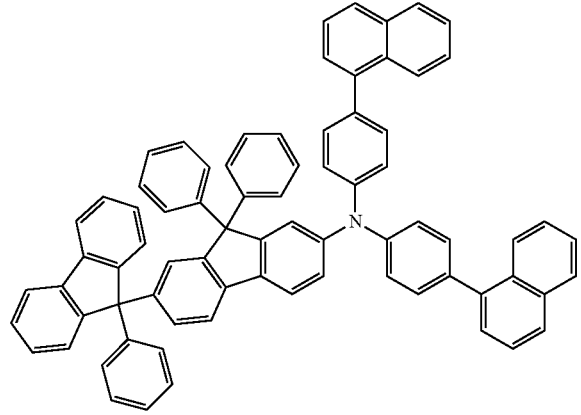

53
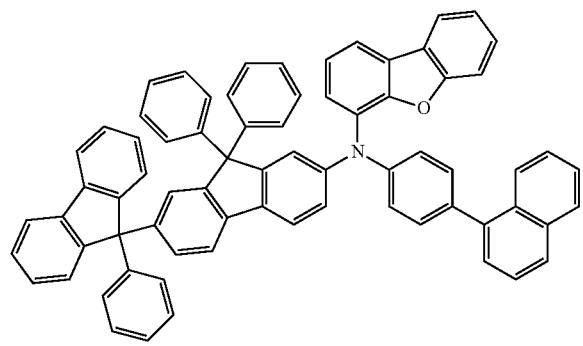
54
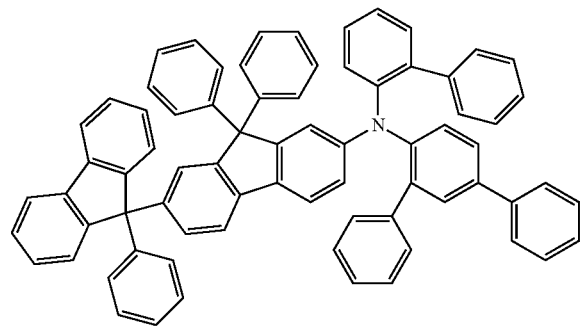
55
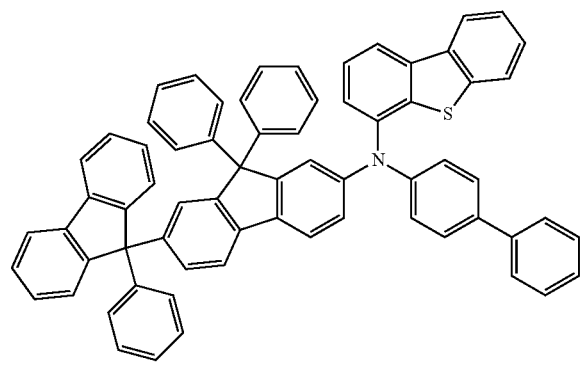
56
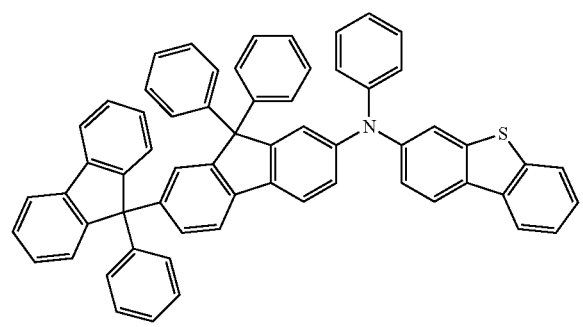
57
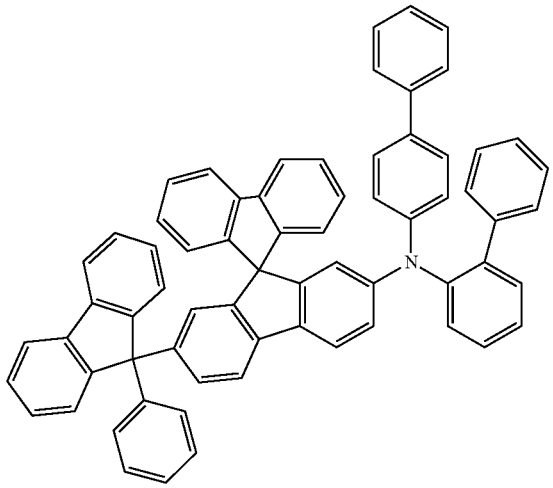
58
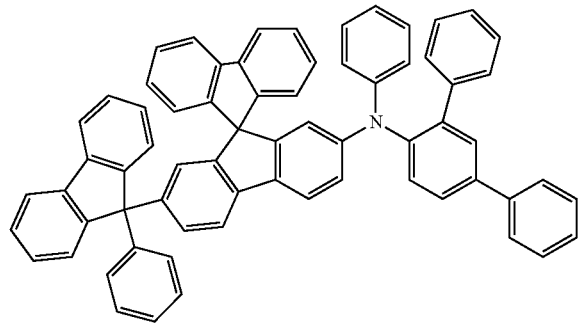
59
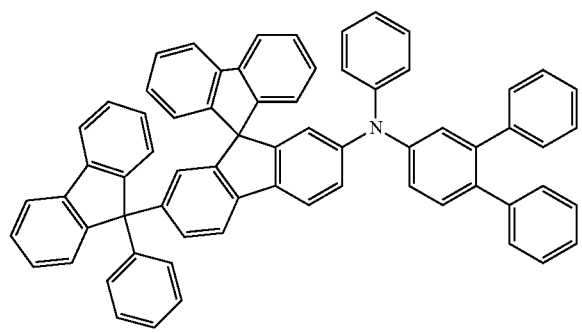
60
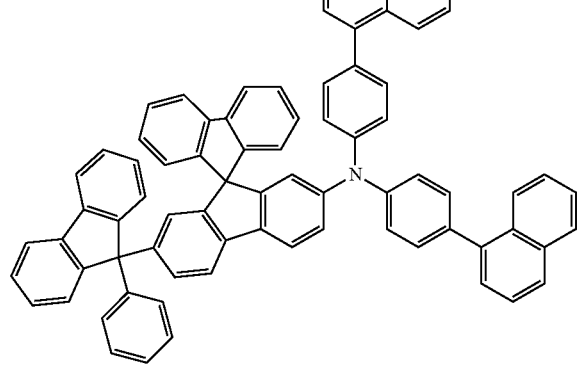

-continued
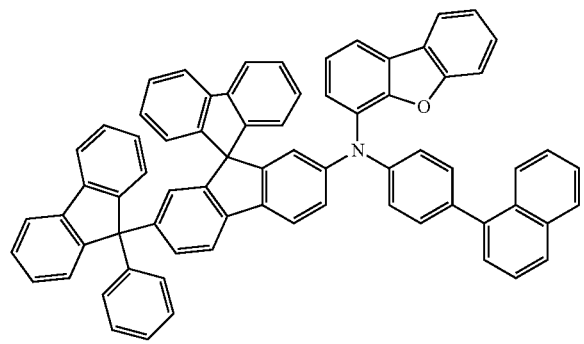
61
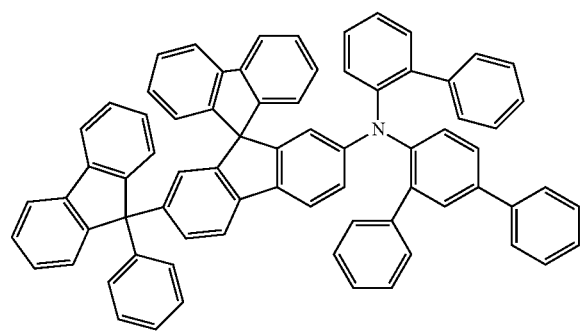
62
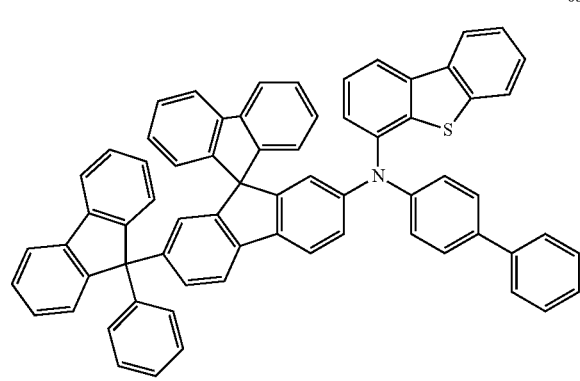
63
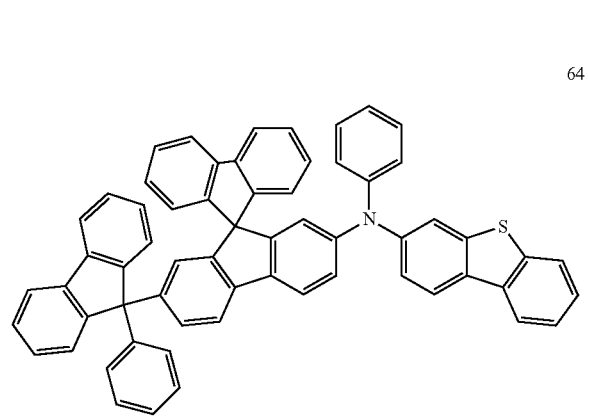
64
The amine compound represented by Formula 1 may be, but is not limited to, any one selected from the compounds represented by the Compound Group 2.
Compound Group 2
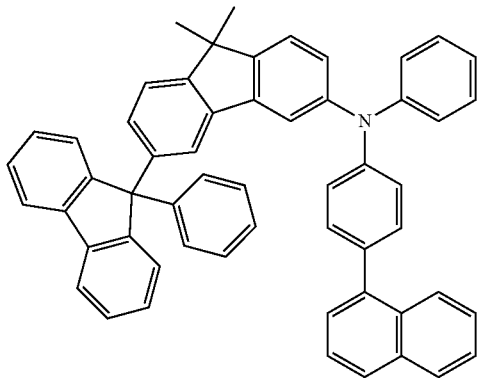
65
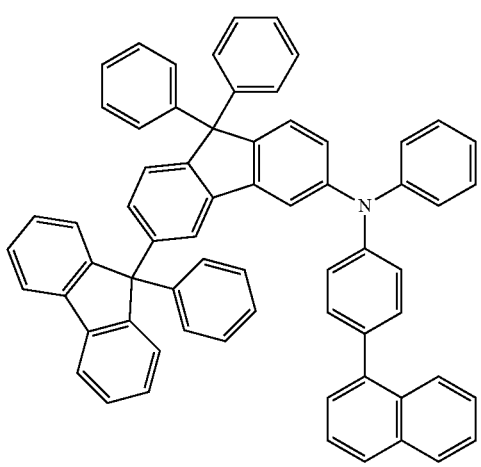
66
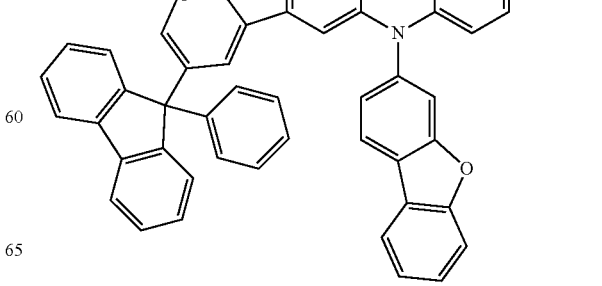
67

68
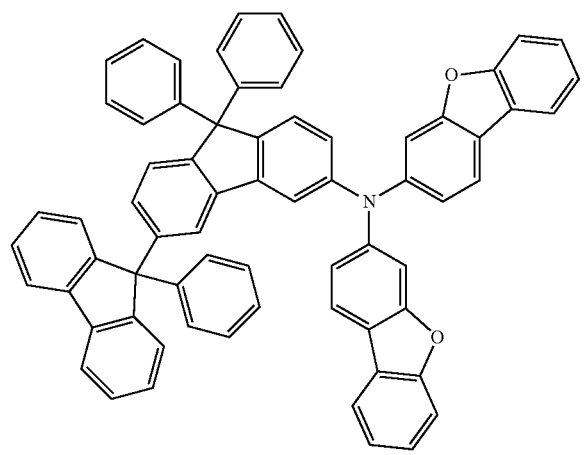
69
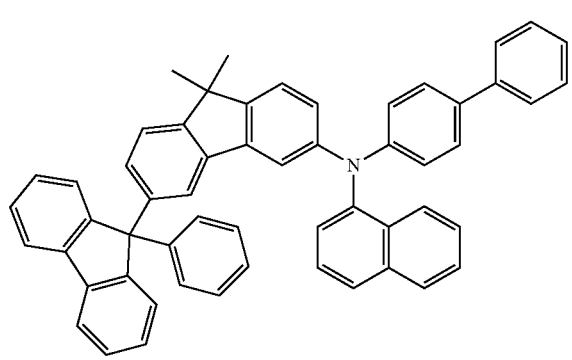
70
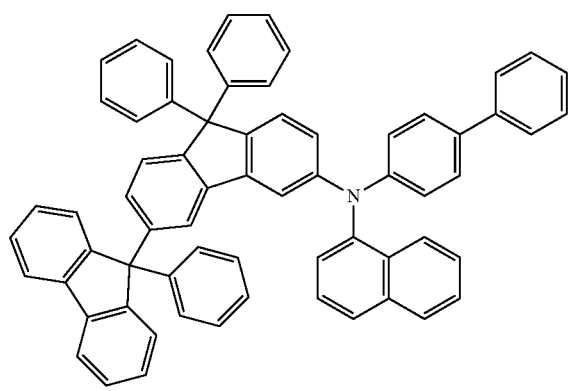
71
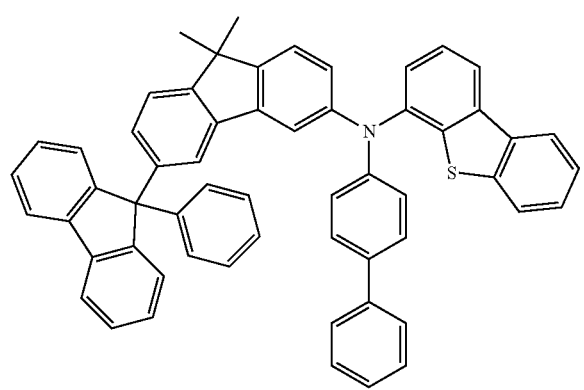
72
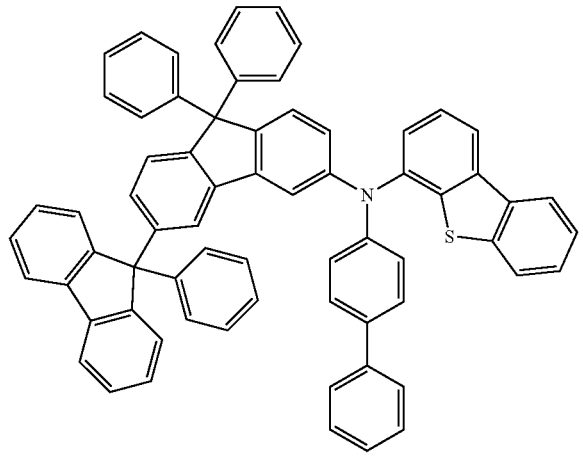
The amine compound represented by Formula 1 may be, but is not limited to, any one selected from the compounds represented by the Compound Group 3.
Compound Group 3
73
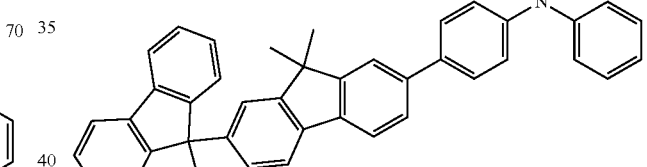
74
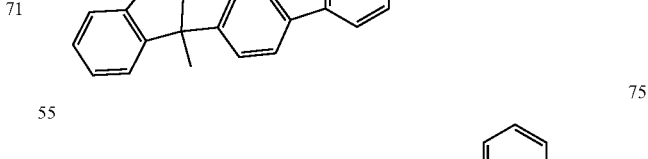
75
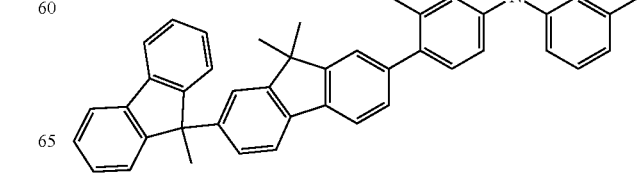

-continued

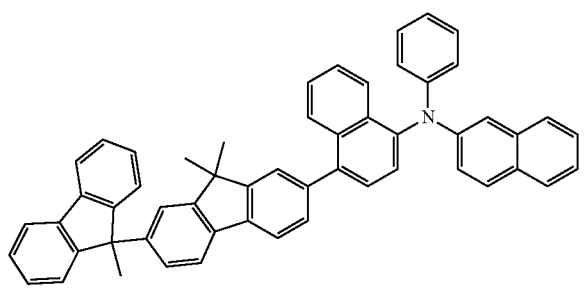
76

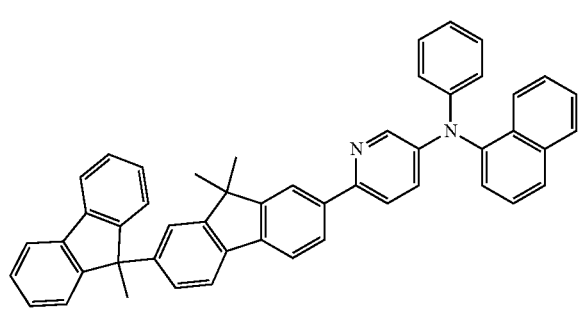
77

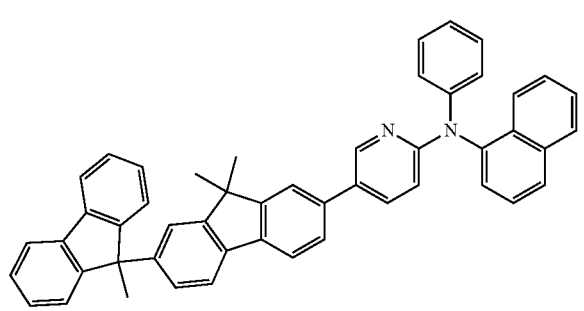
78

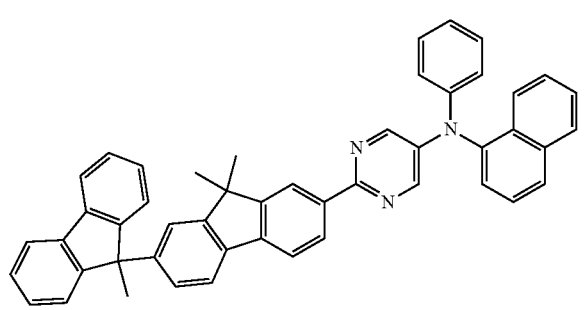
79

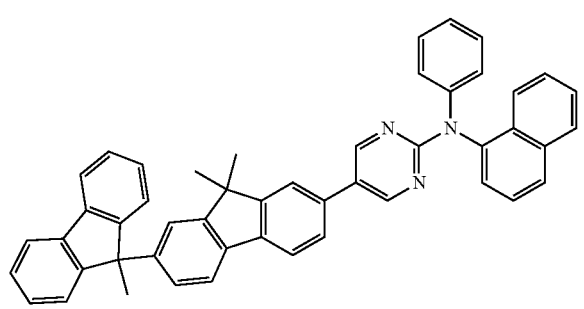
80

The amine compound according to an embodiment of the inventive concept includes a bifluorenyl group. When the amine compound represented by Formula 1 is applied to an organic electroluminescence device, high emission, efficiency, low driving voltage, and long lifetime may be acquired. The amine compound including the bifluorenyl group improves heat resistance and charge resistance while maintaining hole transfer characteristics. Accordingly, the organic electroluminescent device employing (i.e., utilizing) the amine compound may reduce the deterioration of characteristics (e.g., performance) resulting from a high temperature and an electric charge, thereby realizing a longer lifetime. In addition, the amine compound according to an embodiment of the inventive concept may have a strong intermolecular interaction due to the planarity of the fluorenyl group, and thus may improve the mobility of holes, so that the organic electroluminescent device applying (e.g., utilizing) the amine compound may acquire low driving voltage.

Hereinafter, an organic electroluminescence device according to an embodiment of the inventive concept will be described. Hereinafter, differences between the amine compounds according to embodiments of the inventive concept as described above will be described in more detail, and the same descriptions on the amine compounds according to embodiments of the inventive concept described above will not be repeated.

An organic electroluminescence device according to an embodiment of the inventive concept includes the amine compound according to an embodiment of the inventive concept described above.

Figure 2:
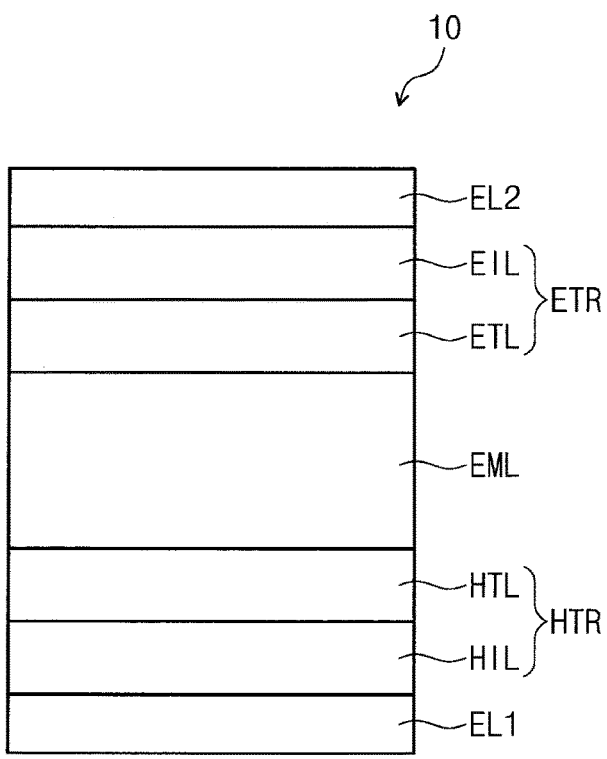
FIG. 2 is a cross sectional view schematically illustrating an organic electroluminescence device according to an embodiment of the inventive concept.

FIG. 1 is a cross sectional view schematically illustrating the organic electroluminescence device, according to an embodiment of the inventive concept. FIG. 2 is a cross sectional view schematically illustrating the organic electroluminescence device, according to an embodiment of the inventive concept.

Referring to FIG. 1 and FIG. 2, the organic electroluminescence device 10 according to an embodiment of the inventive concept includes a first electrode (EL1), a hole transfer region (HTR), a light emitting layer (EML), an electron transfer layer (ETR), and a second electrode (EL2).

The first electrode (EL1) has conductivity (e.g., electrical conductivity). The first electrode (EL1) may be a pixel electrode or a positive electrode. The first electrode may be a transmissive electrode, a transflective electrode, or a reflective electrode. When the first electrode (EL1) is the transmissive electrode, the first electrode (EL1) may be formed of a transparent metal oxide such as indium tin oxide (ITO), indium zinc oxide (IZO), zinc oxide (ZnO), and indium tin zinc oxide (ITZO). When the first electrode (EL1) is a transflective electrode or a reflective electrode, the first electrode (EL1) may include Ag, Mg, Cu, Al, Pt, Pd, Au, Ni, Nd, Ir, Cr, Li, Ca, LiF/Ca, LiF/Al, Mo, Ti, or compounds or mixtures thereof (e.g., a mixture of Ag and Mg). Furthermore, the first electrode may have a multilayered structure including a reflective film or transflective film formed of the foregoing materials and a transparent conductive film formed of indium tin oxide (ITO), indium zinc oxide (IZO), zinc oxide (ZnO), indium tin zinc oxide (ITZO), or the like.

Hereinafter, it will be described as an example that the amine compound according to an embodiment of the inventive concept is included in the hole transfer region (HTR). However, the inventive concept is not limited to the foregoing example, and the amine compound according to an embodiment of the inventive concept may be included in at least one layer of one or more organic layers disposed between the first electrode (EL1) and the second electrode (EL2). For example, the amine compound according to an embodiment of the inventive concept may be included in the light emitting layer (EML).

An organic electroluminescence device according to an embodiment of the inventive concept includes the amine compound according to an embodiment of the incentive concept in the hole transfer region (HTR). For example, the organic electroluminescence device according to an embodiment of the inventive concept may include an amine compound represented by Formula 1 in the hole transfer region (HTR)

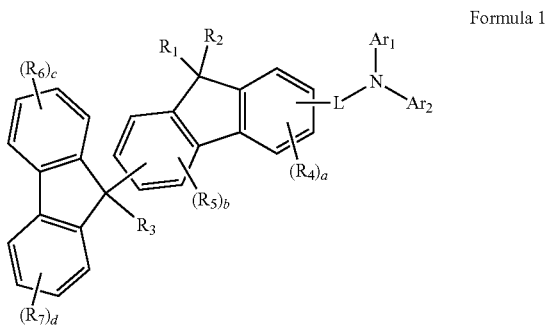

Formula 1

In Formula 1, detailed description for $Ar_1$, $Ar_2$, L, $R_1$ to $R_7$, and a to d is the same as those described above, and will not be repeated again.

Detailed description for the amine compound represented by Formula 1 is the same as those described above, and will not be repeated again.

The hole transfer region (HTR) is disposed on the first electrode (EL1). The hole transfer region (HTR) may include at least one of a hole injection layer (HIL), a hole transfer layer (HTL), a hole buffer layer, or an electron blocking layer.

The hole transfer region (HTR) may be a single layer formed of a single material, a single layer formed of a plurality of different materials, or may have a multilayered structure with a plurality of layers formed of a plurality of different materials.

For example, the hole transfer region (HTR) may have a single layered structure formed of the hole injection layer (HIL) or the hole transfer layer (HTL), and a single layered structure formed of the hole injection material and/or the hole transfer material. Also, the hole transfer region (HTR) may have, but is not limited to, a single layered structure formed of a plurality of different materials or a multilayered structure sequentially layered from the first electrode (EL1), such as a structure formed of a hole injection layer (HIL)/a hole transfer layer, a hole injection layer (HIL)/a hole transfer layer (HTL)/a hole buffer layer, a hole injection layer (HIL)/a hole buffer layer, a hole transfer layer (HTL)/a hole buffer layer, or a hole injection layer (HIL)/a hole transfer layer (HTL)/a hole blocking layer.

The hole transfer region (HTR) may be formed by utilizing various suitable methods such as a vacuum deposition method, a spin coating method, a casting method, a Langmuir-Blodgett (LB) method, an inkjet printing method, a laser printing method, and a laser induced thermal imaging method (LITI).

The hole transfer region (HTR) may include the amine compound according to an embodiment of the inventive concept described above. The hole transfer region (HTR) may include the amine compound according to an embodiment of the inventive concept described above as the hole transfer material.

When the hole transfer layer (HTL) includes the amine compound according to an embodiment of the inventive concept, the hole transfer layer (HTL) may include, for example, phthalocyanine compounds (such as copper phthalocyanine); DNTPD (N,N'-diphenyl-N,N'-bis-[4-(phenyl-m-tolyl-amino)-phenyl]-biphenyl-4,4'-diamine), m-MTDATA (4,4',4"-tris(3-methylphenylphenylamino)triphenylamine), TDATA (4,4'4"-Tris(N,N-diphenylamino)triphenylamine), 2-TNATA (4,4',4"-tris{N,-(2-naphthyl)-N-phenylamino}-triphenylamine), PEDOT/PSS (Poly(3,4-ethylenedioxythiophene)/Poly(4-styrenesulfonate)), PANI/DBSA (Polyaniline/Dodecylbenzenesulfonic acid), PANI/CSA (Polyaniline/Camphor sulfonicacid), PANI/PSS ((Polyaniline)/Poly(4-styrenesulfonate)), NPB (N,N'-di(naphthalene-1-yl)-N,N'-diplienyl-benzidine), polyether ketones (TPA-PEK) containing triphenylamine, 4-Isopropyl-4'-methyldiphenyliodonium Tetrakis(pentafluorophenyl) borate], or the like.

The hole transfer layer (HTL) may further include a known material in addition to the amine compound according to an embodiment of the inventive concept. The hole transfer layer (HTL) may include, for example, carbazole-based derivatives (such as N-phenylcarbazole and polyvinylcarbazole); fluorine-based derivatives; triphenylamine derivatives (such as TPD (N, N'-bis (3-methylphenyl)-N, N'-diphenyl-[1,1-biphenyl]-4,4'-diamine), and TCTA (4,4'-carbazolyl) triphenylamine)); NPB (N,N'-di(1-naphthyl)-N, N'-diphenylbenzidine); TAPC (4,4'-Cyclohexylidene bis[N, N-bis(4-methylphenyl)benzenamine]); HMTPD (4,4'-Bis [N,N'-(3-tolyl)amino]-3,3'-dimethylbiphenyl), or the like.

The thickness of the hole transfer region (HTR) may be about 150 Å to about 10,000 Å, for example, about 150 Å to about 1,500 Å. When the hole transfer region (HTR) includes both the hole injection layer (HIL) and the hole transfer layer (HTL), the thickness of the hole injection layer (HIL) may be about 100 Å to about 10,000 Å, for example, about 100 Å to about 1,000 Å, and the thickness of the hole transfer layer (HTL) may be about 30 Å to about 1,000 Å. When the thicknesses of the hole transfer region (HTR), the hole injection layer (HIL), and the hole transfer layer (HTL) satisfy the ranges above, satisfactory hole transfer characteristics may be obtained without a substantial increase in driving voltage.

In addition to the above-mentioned materials, the hole transfer region (HTR) may further include an electric charge-generating material for improving conductivity. The electric charge-generating material may be uniformly or non-uniformly dispersed in the hole transfer region (HTR). The electric charge-generating material may be, for example, a p-dopant. The p-dopant may be, but is not limited to, one of a quinone derivative, a metal oxide, and a cyano group-containing compound. For example, non-limiting examples of the p-dopant may include quinone derivatives (such as TCNQ (Tetracyanoquinodimethane) or F4-TCNQ (2, 3, 5, 6-tetrafluoro-tetracyanoquinodimethane)) and metal oxides (such as tungsten oxide or molybdenum oxide).

The hole transfer region (HTR) may further include at least one of a hole buffer layer and an electron blocking layer in addition to the hole injection layer (HIL) and/or the hole transfer layer (HTL). The hole buffer layer may compensate for the resonance distance (depending on the wave length of the light emitted from the light emitting layer (EML)) to increase light emission efficiency. The material included in the hole transfer region (HTR) may be utilized as the material included in the hole buffer layer. The electron blocking layer is a layer that serves to reduce or prevent the electron injection from the electron transfer region (HTR) into the hole transfer layer (HTL).

The light emitting layer (EML) is disposed on the hole transfer region (HTR).

The thickness of the light emitting layer (EML) may be, for example, about 100 Å to about 300 Å. The light emitting layer (EML) may be a single layer formed of a single material, a single layer formed of a plurality of different materials, or may have a multilayered structure including a plurality of layers formed of a plurality of different materials.

The light emitting layer (EML) may emit one of red light, green light, blue light, white light, yellow light, and cyan light. The light emitting layer (EML) may include a fluorescent material or a phosphorescent material. Also, the light emitting layer (EML) may include a host and a dopant. The light emitting layer (EML) may have, for example, a thickness of 10 nm to 60 nm.

A host material of the light emitting layer (EML) may be selected from an anthracene derivative, a fluoranthene derivative, a pyrene derivative, an arylacetylene derivative, a fluorene derivative, a perylene derivative, a chrysene derivative, a phenanthrene derivative, etc. For example, the host material of the light emitting layer (EML) may include a pyrene derivative, a perylene derivative, a chrysene derivative, a phenanthrene derivative, and/or an anthracene derivative. For example, as the host material of the light emitting layer (EML), an anthracene derivative represented by the Formula 4 may be utilized.

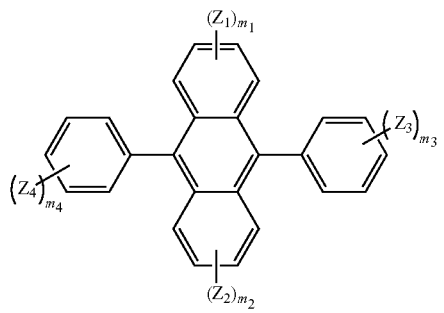

Formula 4

In Formula 4, $Z_1$ to $Z_2$ are each independently hydrogen, deuterium, a halogen atom, a substituted or unsubstituted silyl group, a substituted or unsubstituted alkyl group having 1 to 15 carbon atoms, a substituted or unsubstituted aryl group having 6 to 30 carbon atoms for forming a ring, or a substituted or unsubstituted heteroaryl group having 2 to 30 carbon atoms for forming a ring. Also, $m_1$ and $m_2$ are each independently an integer of 0 to 4, and $m_3$ and $m_4$ are each independently an integer of 0 to 5. In Formula 4, $Z_3$ and $Z_4$ may each independently combine with a neighboring group to form a ring.

An example of the compound represented by Formula 4 may include, but is not limited to, a compound represented by chemical structures a-1 to a-12.

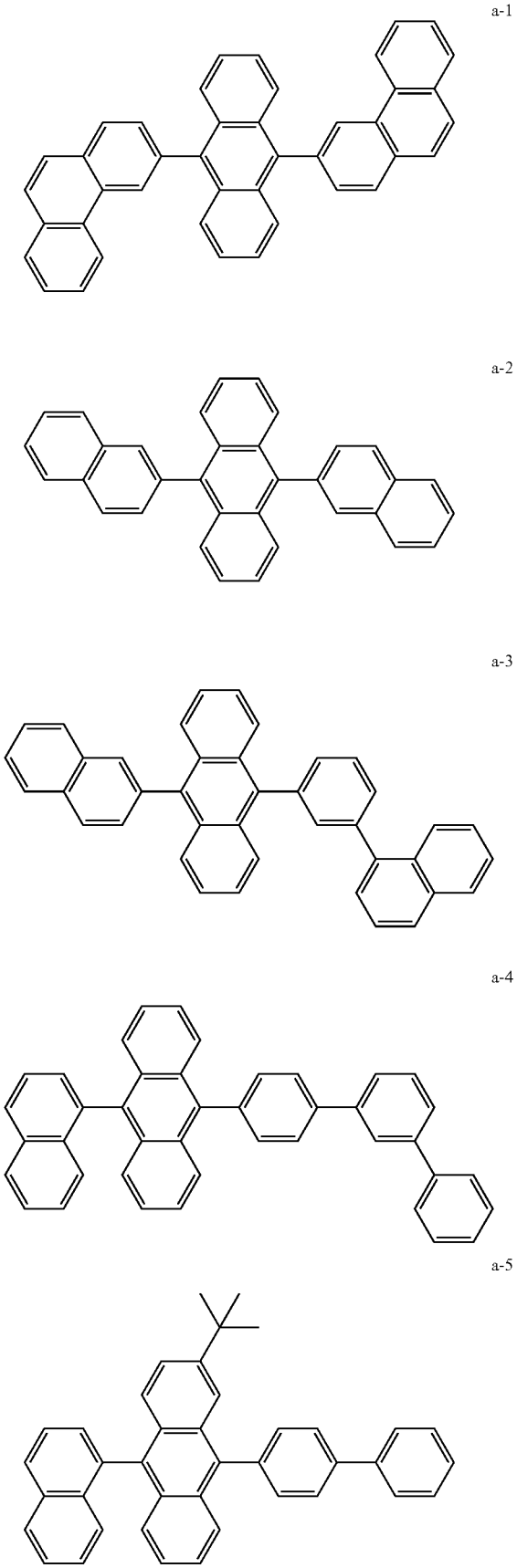

-continued a-6
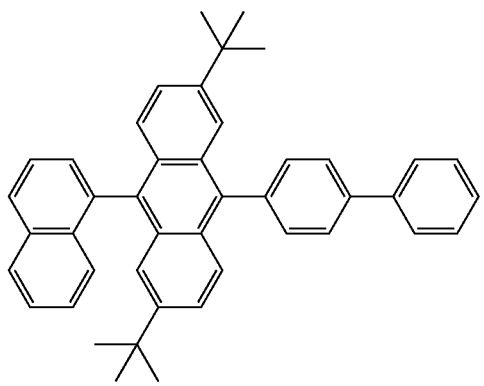

a-7
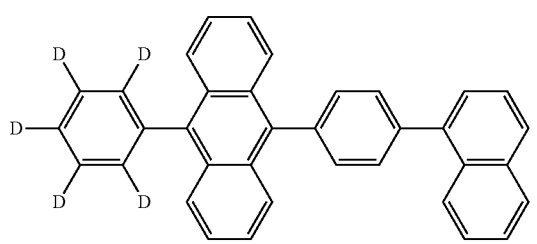

a-8
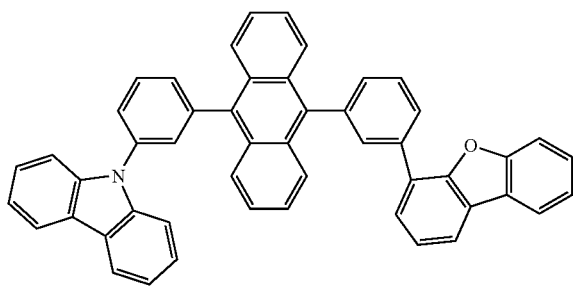

a-9
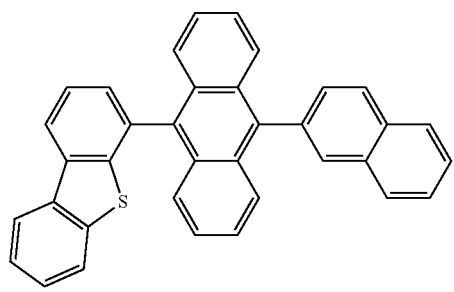

a-10
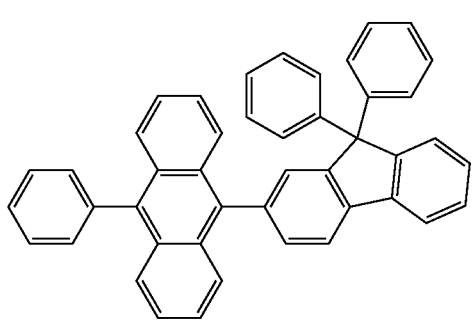

-continued a-11
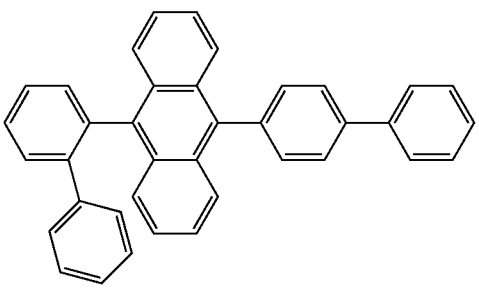

a-12
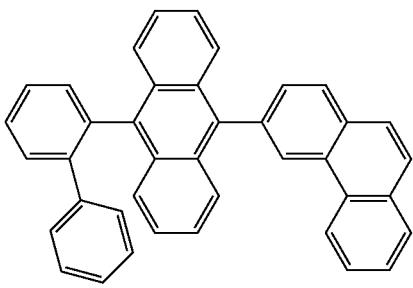

The host material is not particularly limited as long as being a commonly utilized suitable material. Examples of the host material may include Alq$_3$(tris(8-hydroxyquinolino) aluminum), CBP (4,4'-bis(N-carbazolyl)-1,1'-biphenyl), PVK (poly(N-vinylcabazole), ADN (9,10-di(naphthalene-2-yl)anthracene), TCTA (4,4',4''-Tris(carbazol-9-yl)-triphenylamine), TPBi (1,3,5-tris(N-phenylbenzimidazole-2-yl)benzene), TBADN (3-tert-butyl-9,10-di(naphth-2-yl) anthracene), DSA (distyrylarylene), CDBP (4,4'-bis(9-carbazolyl)-2,2'-dimethyl-biphenyl), MADN (2-Methyl-9,10-bis(naphthalen-2-yl)anthracene), or the like.

The dopant may include, for example, styryl derivatives (e.g., 1,4-bis[2-(3-N-ethylcarbazoryl)vinyl]benzene (BCzVB), 4-(di-p-tolylamino)-4'-[(di-p-tolylamino)styryl]stilbene (DPAVB), N-(4-((E)-2-(6-((E)-4-(diphenylamino) styryl)naphthalen-2-yl)vinyl)phenyl)-N-phenylbenze- namine (N-BDAVBi); perylene and derivatives thereof (e.g., 2,5,8,11-Tetra-tert-butylperylene (TBP)); a pyrene and derivatives thereof (e.g., 1,1-dipyrene, 1,4-dipyrenylbenzene, 1,4-Bis (N, N-diphenylamino) pyrene), or the like.

When the light emitting layer (EML) emits red light, the light emitting layer (EML) may further include, for example, PBD: Eu(DBM)$_3$(Phen)(tris(dibenzoylmethanato)phenanthroline europium) or a fluorescent material including perylene. When the light emitting layer (EML) emits red light, the dopant included in the light emitting layer (EML) may be selected from, for example, a metal complex or organometallic complex (such as PIQIr(acac) (bis(1-phenylisoquinoline) acetylacetonate iridium), PQIr(acac) (bis (1-phenylquinoline) acetylacetonate iridium), PQIr (tris(1-phenylquinoline)iridium), or PtOEP (octaethylporphyrin platinum)); rubrene and derivatives thereof; and 4-dicyanomethylene-2-(p-dimethylaminostyryl)-6-methyl-4H-pyran (DCM) and derivatives thereof.

When the light emitting layer (EML) emits green light, the light emitting layer (EML) may further include, for example, a fluorescent material including Alq$_3$ (tris(8-hydroxyquinolino) aluminum). When the light emitting layer (EML) emits green light, the dopant included in the light emitting layer (EML) may be selected from, for example, a metal complex or an organometallic complex (such as Ir(ppy)$_3$(fac-tris (2-phenylpyridine) iridium), coumarin or derivatives thereof).

When the light emitting layer (EML) emits blue light, the light emitting layer (EML) may further include, for example, a fluorescent material including any one selected from spiro-DPVBi, spiro-6P, DSB (distyryl-benzene), DSA (distyryl-arylene), PFO (polyfluorene) based polymer, and PPV (poly (p-phenylene vinylene) based polymer. When the light emitting layer (EML) emits blue light, the dopant included in the light emitting layer (EML) may be selected from, for example, a metal complex or organometallic complex (such as (4,6-F$_2$ppy)$_2$Irpic, perylene or derivatives thereof).

The electron transfer region (ETR) is disposed on the light emitting layer. The electron transfer region (ETR) may include, but is not limited to, at least one of a hole blocking layer, an electron transfer layer (ETL), or an electron injection layer (EIL).

The electron transfer region (ETR) may be a single layer formed of a single material, a single layer formed of a plurality of different materials, or may have a multilayered structure including a plurality of layers formed of a plurality of different materials.

For example, the electron transfer region (ETR) may have a single layer structure formed of the electron injection layer (EIL) or the electron transfer layer (ETL), or may have a single layer structure formed of an electron injection material and/or an electron transfer material. In addition, the electron transfer region (ETR) may have, but is not limited to, a single layer structure formed of a plurality of different materials, or a multilayered structure sequentially layered from the first electrode (EL1), such as a structure formed of an electron transfer layer (ETL)/electron injection layer (EIL) or a hole blocking layer/electron transfer layer (ETL)/electron injection layer (EIL).

The electron transfer region (ETR) may be formed utilizing various suitable methods such as a vacuum deposition method, a spin coating method, a casting method, an LB (Langmuir-Blodgett) method, an inkjet printing method, a laser printing method, or a laser induced thermal imaging (LITI) method.

When the electron transfer region (ETR) includes an electron transfer layer (ETL), the electron transfer region (ETR) may include, but is not limited to, Alq3 (Tris(8-hydroxyquinolinato)aluminum), 1,3,5-tri[(3-pyridyl)-phen-3-yl]benzene, 2,4,6-tris(3'-(pyridin-3-yl)biphenyl-3-yl)-1,3,5-triazine, 2-(4-(N-phenylbenzoimidazolyl-1-ylphenyl)-9,10-dinaphthyllanthracene, TPBi (1,3,5-Tri(1-pheny-1H-benzo[d]imidazol-2-yl)phenyl), BCP (2,9-Dimethyl-4,7-diphenyl-1,10-phenanthroline), Bphen (4,7-Diphenyl-1,10-phenanthroline), TAZ (3-(4-Biphenylyl)-4-phenyl-5-tert-butylphenyl-1,2,4-triazole), NTAZ (4-(Naphthalen-1-yl)-3,5-diphenyl-4H-1,2,4-triazole), tBu-PBD (2-(4-Biphenylyl)-5-(4-tert-butylphenyl)-1,3,4-oxadiazole), BAlq (Bis(2-methyl-8-quinolinolato-N1,O8)-(1,1'-Biphenyl-4-olato) aluminum), Bebq$_2$ (berylliumbis(benzoquinolin-10-olate), ADN (9,10-di(naphthalene-2-yl)anthracene), and mixtures thereof. The thickness of the electron transfer layers (ETL) may be about 100 Å to about 1,000 Å, for example, about 150 Å to about 500 Å. When the thickness of the electron transfer layer (ETL) satisfies the ranges above, satisfactory electron transfer characteristics may be obtained without a substantial increase in driving voltage.

When the electron transfer region (ETR) includes an electron injection layer (EIL), metals such as Al, Ag, Li, Mg and Ca, and mixtures thereof may be included. However, the embodiment of the inventive concept is not limited thereto. For example, the electron injection layer may include, but is not limited to, lanthanum group metals (such as LiF, Lithium quinolate (LiQ), Li$_2$O, BaO, NaCl, CsF, or Yb); or halogenated metals (such as RbCl or RbI). The electron injection layer (EIL) may also be formed of a mixture of the electron transfer material and an insulating organo metal salt. The organo metal salt may be a material having an energy band gap of about 4 eV or more. For example, the organo metal salt may include a metal acetate, a metal benzoate, a metal acetoacetate, a metal acetylacetonate, or a metal stearate. The thickness of the electron injection layers (EIL) may be about 1 Å to about 100 Å, about 3 Å to about 90 Å. When the thickness of the electron injection layers (EIL) satisfies the ranges above, satisfactory electron injection characteristics may be obtained without substantial increase in driving voltage.

As described above, the electron transfer region (ETR) may include a hole blocking layer. For example, the hole blocking layer may include, but is not limited to, at least one of BCP (2,9-dimethyl-4,7-diphenyl-1,10-phenanthroline) or Bphen (4,7-diphenyl-1,10-phenanthroline).

The second electrode (EL2) is disposed on the electron transfer region (ETR). The second electrode (EL2) may be a common electrode or a negative electrode. The second electrode (EL2) may be a transmissive electrode, a transflective electrode or a reflective electrode. When the second electrode (EL2) is the transmissive electrode, the second electrode (EL2) may be formed of a transparent metal oxide (such as indium tin oxide (ITO), indium zinc oxide (IZO), zinc oxide (ZnO), or indium tin zinc oxide (ITZO)).

When the second electrode (EL2) is a transflective electrode or a reflective electrode, the second electrode (EL2) may include Ag, Mg, Cu, Al, Pt, Pd, Au, Ni, Nd, Ir, Cr, Li, Ca, LiF/Ca, LiF/Al, Mo, Ti, or compounds or mixtures thereof (for example, a mixture of Ag and Mg). Also, the second electrode (EL2) may have a multilayered structure including a reflective film or a transflective film formed of the foregoing materials, and a transparent conductive film formed of indium tin oxide (ITO), indium zinc oxide (IZO), zinc oxide (ZnO), indium tin zinc oxide (ITZO), or the like.

Although not illustrated, the second electrode (EL2) may be connected to an auxiliary electrode. When the second electrode (EL2) is connected to the auxiliary electrode, the resistance of the second electrode (EL2) may be reduced.

In the organic electroluminescence device 10, holes injected from the first electrode (EL1) according to a voltage applied to the first electrode (EL1) and the second electrode (EL2) are moved to the light emitting layer (EML) through the hole transfer region (HTR), and electrons injected from the second electrode (EL2) are moved to the light emitting layer (EML) through the electron transfer region (ETR). The electrons and holes are recombined in the light emitting layer (EML) to generate excitons, and the excitons emit light when falling from the excited state to the ground state.

When the organic electroluminescence device 10 is a front emission device, the first electrode (EL1) may be a reflective electrode, and the second electrode (EL2) may be a transmissive electrode or a transflective electrode. When the organic electroluminescence device 10 is a rear emission device, the first electrode (EL1) may be a transmissive electrode or a transflective electrode, and the second electrode (EL2) may be a reflective electrode.

The organic electroluminescence device according to an embodiment of the inventive concept may include an amine compound represented by Formula 1 to obtain low driving voltage and long lifetime. The amine compound according to an embodiment of the inventive concept may be disposed in the hole transfer region (HTR) of the organic electroluminescence device, and have a high hole transfer characteristic and a reduced thermal load, thereby acquiring low driving voltage, high emission efficiency, and long lifetime. For example, the amine compound represented by Formula 1 may include a bifluorenyl group, thereby improving heat resistance and charge resistance while maintaining the hole transfer characteristics. Therefore, the organic electroluminescence device employing the amine compound may reduce the deterioration of characteristics resulting from a high temperature and an electric charge, thereby achieving a longer lifetime. Also, due to the planarity of the fluorenyl group, an intermolecular interaction is strengthened and thus the mobility of holes is improved, so that the organic electroluminescent device employing the same may acquire low driving voltage.

Hereinafter, the inventive concept will be described in more detail with reference to specific production methods, examples and comparative examples. The following examples are provided only for illustrative purposes and will not be construed as limiting the scope of the inventive concept.

The amine compound according to an embodiment of the inventive concept may be synthesized, for example, as follows. However, the embodiment of the inventive concept is not limited thereto.

Synthesis Example

1. Synthesis of Compound 18
(Synthesis of Compound A)

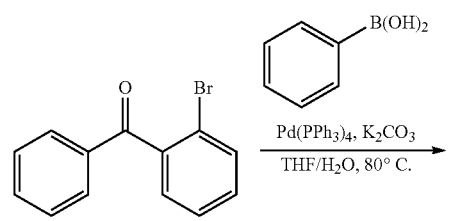

In an atmosphere of argon (Ar), 80 mL of a mixed solution of THF/water (20%) in which 2.61 g of 2-bromobenzophenone, 1.50 g of phenylboronic acid, 0.441 g of $K_2CO_3$ and 0.122 g of Pd $(PPh_3)_4$ were dissolved in a 200 ml three-necked flask was heated and stirred for 5 hours at 80° C. After air cooling, dichloromethane was added to separate an organic layer, and the solvent was evaporated. The obtained product was purified by silica gel column chromatography (hexane/AcOEt) to obtain 1.86 g (yield 72%) of Compound A having a pale yellow solid. The molecular weight of Compound A measured by FAB-MS measurement was 258.

(Synthesis of Compound B)

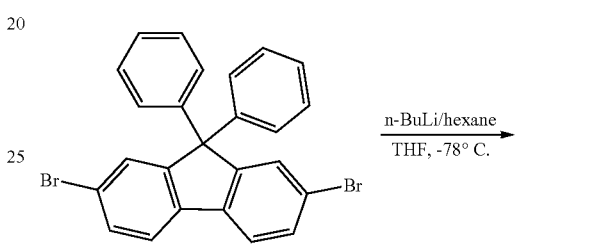

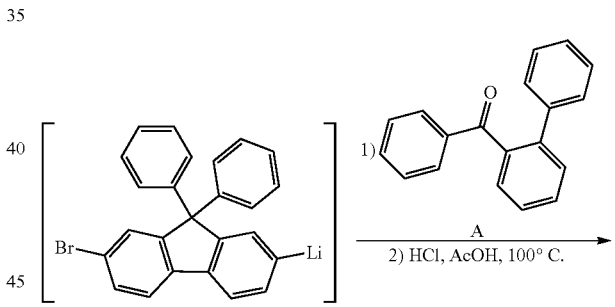

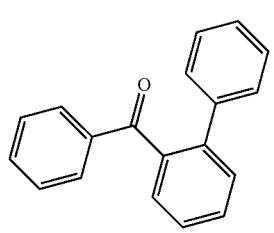

A (72%)

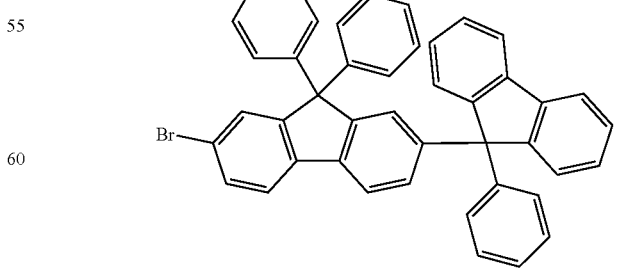

B (87%)

In an atmosphere of argon (Ar), after 5.30 g of 2,7-dibromo-9,9-diphenyl-9H-fluorene and 40 mL of THF solvent were added to a 200 mL three-necked flask and cooled to −78° C., 7.00 mL of hexane solution (1.6 M) of n-BuLi was added and stirred for 50 minutes. Thereafter, 30 mL of THF solution in which 3.16 g of Compound A was dissolved was added dropwise, followed by stirring at −78° C. for 50 minutes, returning to room temperature, and further stirring for 3 hours. A saturated aqueous NH$_4$Cl solution was then added to separate an organic layer and the solvent was evaporated. The obtained residue, 100 mL of acetic anhydride, and 4 mL of hydrochloric acid were added to a 200 mL three-necked flask, and the mixture was heated at 100° C. and stirred while heating for 3 hours. The reaction solution was poured into 40 mL of ice water to precipitate a solid and the precipitated solid was subjected to suction filtration. The obtained residue was purified by silica gel column chromatography (hexane/AcOEt) to obtain 6.17 g (yield 87%) of Compound B as a white solid. The molecular weight of the compound B measured by FAB-MS measurement was 637.

[Synthesis of Compound 18]

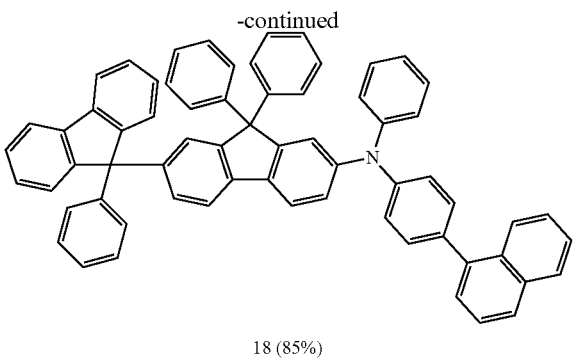

18 (85%)

In an atmosphere of argon (Ar), 6.17 g of compound B, 2.60 g of 4-(1-naphthalenyl)-N-phenyl-benzenamine, 0.081 g of Pd(OAc)$_2$, 1.69 g of NaOtBu, and 0.033 g of tBu$_3$P were added to a 100 ml two-necked flask. The mixture was refluxed for 6 hours with heating and stirring. After air cooling, water was added to separate an organic layer and the solvent was evaporated. The obtained product was purified by a Silica gel column chromatography (hexane/toluene) to obtain 6.28 g (yield 85%) of Compound 18 as a white solid. The molecular weight of the measured compound by FAB-MS measurement was 852. Also, the chemical shift values of the compounds measured in $^1$H-NMR measurement were 8.45 (dd, 4H), 8.41 (d, 1H), 8.25 (dd, 4H), 8.10 (d, 2H), 8.02-7.89 (m, 8H), 7.92-7.77 (m, 8H), 7.69-7.62 (m, 8H), 7.48-7.43 (m, 3H), 7.41-7.25 (m, 4H), 7.18-7.02 (m, 3H). From the above results, the compound as a white solid was confirmed to be Compound 18.

2. Synthesis of Compound 10

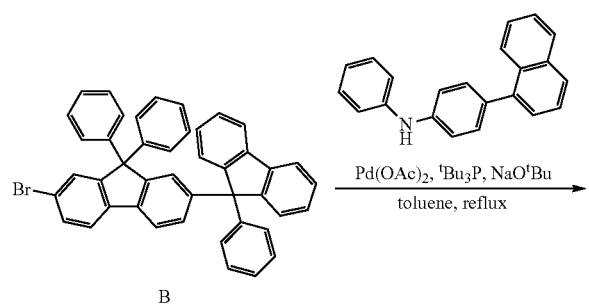

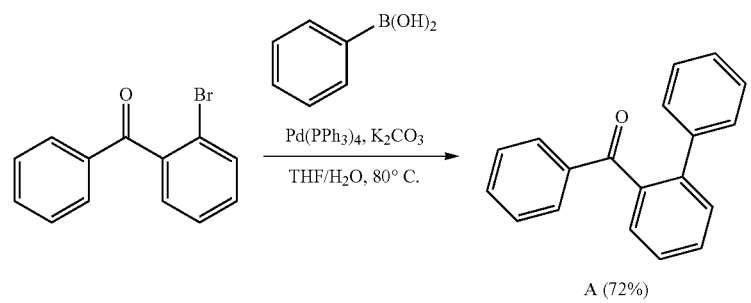

A (72%)

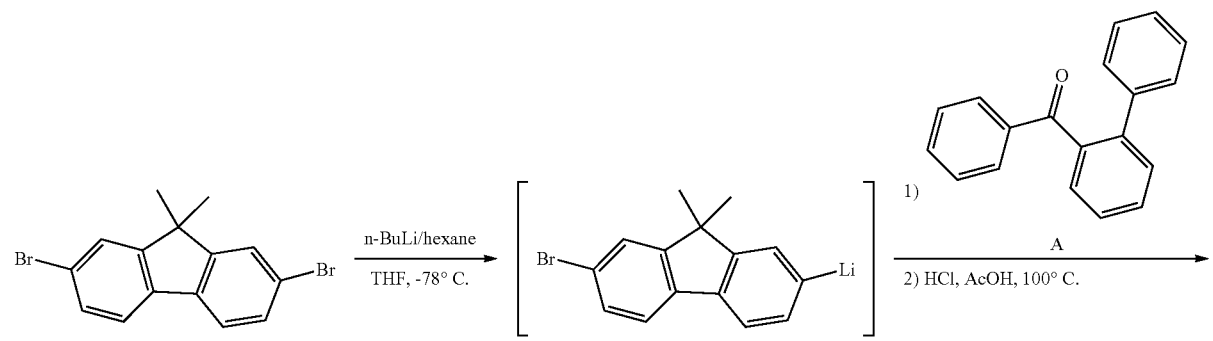

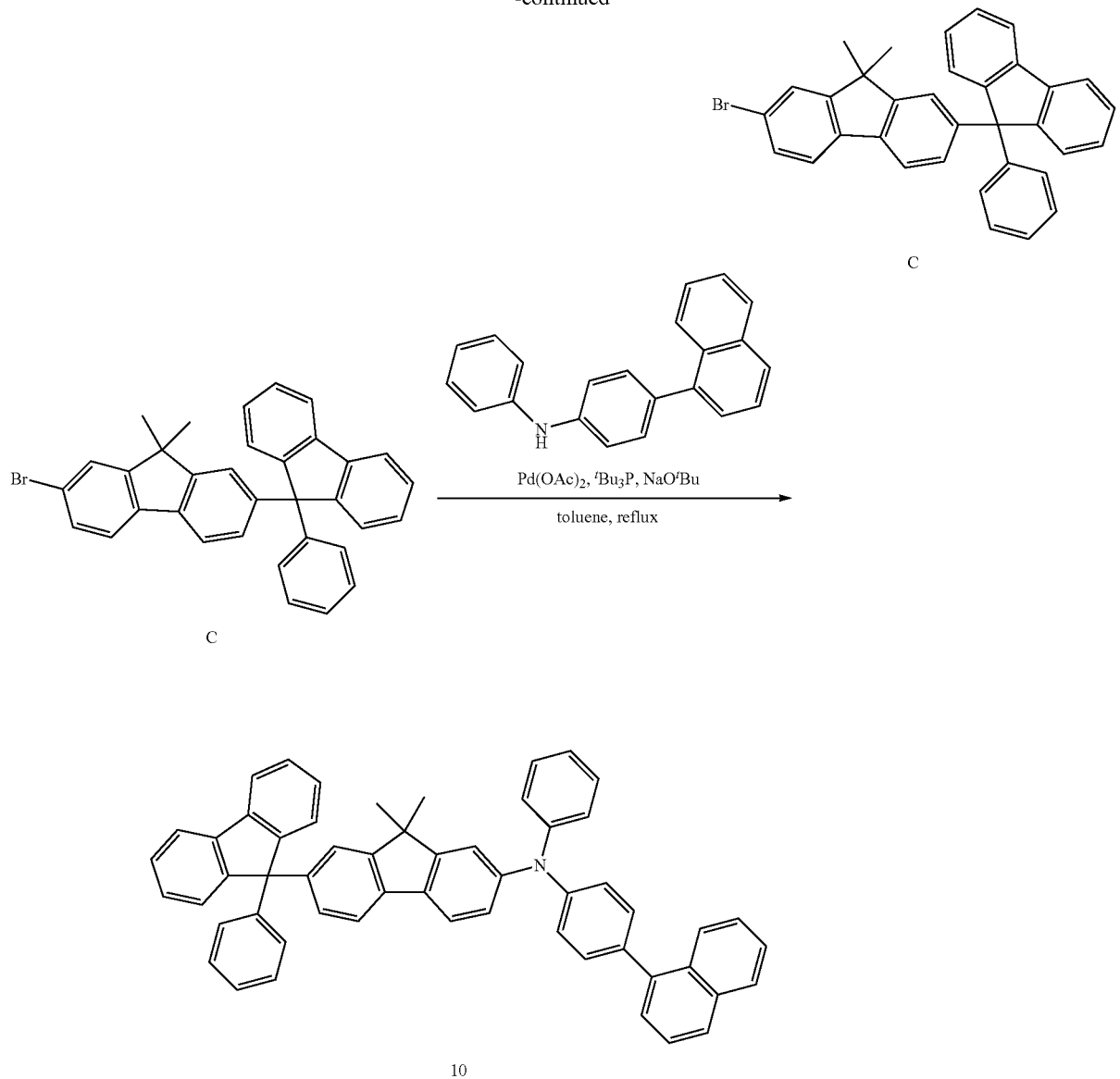

Compound 10 was synthesized in substantially the same manner as in the synthesis of Compound 18 except that 2,7-dibromo-9,9-dimethyl-9H-fluorene was utilized in place of 2,7-dibromo-9,9-diphenyl-9H-fluorene. The molecular weight of the compound measured by FAB-MS measurement was 728. Also, the chemical shift values of the compound measured by $^1$H-NMR were 8.43 (dd, 4H), 8.40 (d, 1H), 8.25 (dd, 4H), 8.10 (d, 2H), 7.98-7.78 (m, 6H), 7.69-7.60 (m, 8H), 7.51-7.25 (m, 7H), 7.18-7.02 (m, 3H), 0.90 (s, 6H). From the above results, the synthesized compound was confirmed to be Compound 10.

3. Synthesis of Compound 25

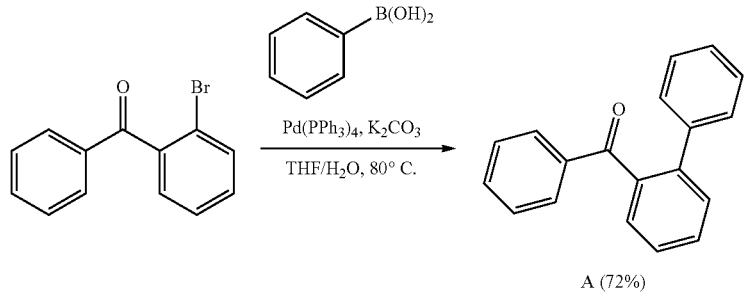

-continued
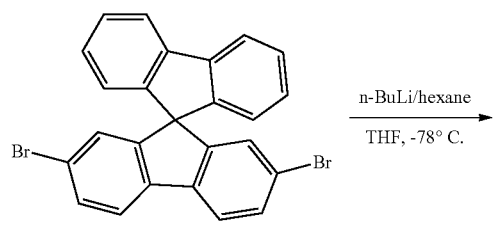
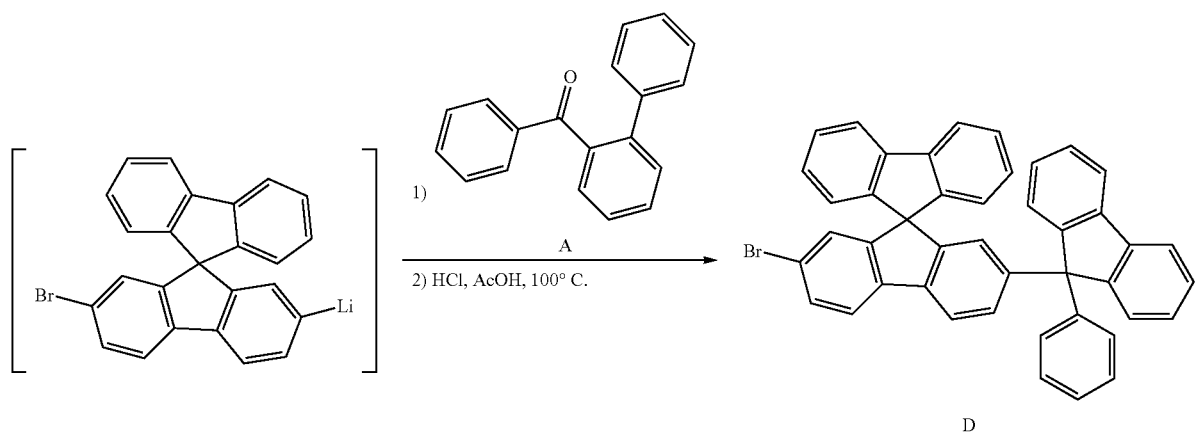
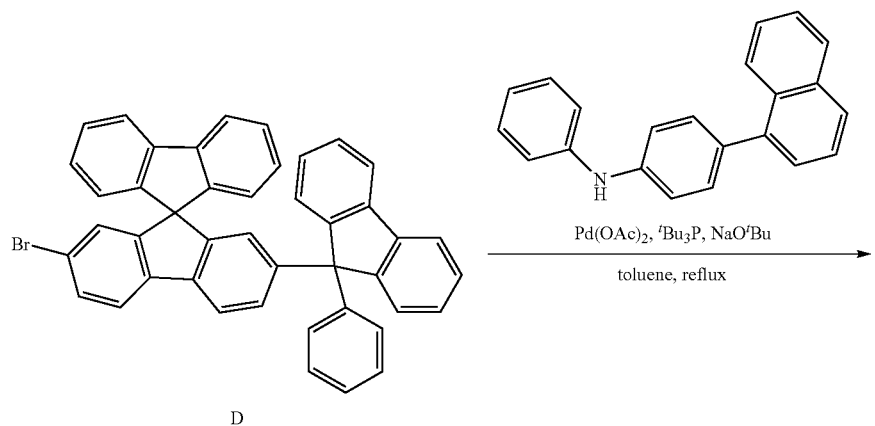
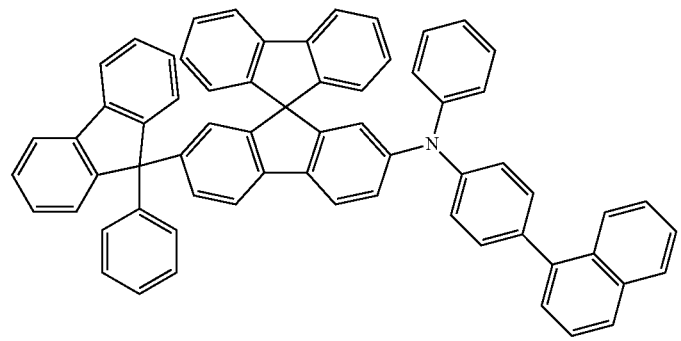
25

Compound 25 was synthesized in substantially the same manner as in the synthesis of Compound 18, except that 2,7-dibromo-9,9'-Spirobi[9H-fluorene] was utilized in place of 2,7-dibromo-9,9-diphenyl-9H-fluorene. The molecular weight of the compound measured by FAB-MS was 850. Also, the chemical shift values of the compound measured by $^1$H-NMR measurement was 8.46 (dd, 4H), 8.41 (d, 1H), 8.28 (dd, 4H), 8.02-7.89 (m, 8H), 7.90-7.77 (m, 8H), 7.69-7.62 (m, 8H), 7.49-7.44 (m, 3H), 7.41-7.33 (m, 4H), 7.17-7.02 (m, 3H). From the above results, the synthesized compound was confirmed to be Compound 25.

4. Synthesis of Compound 66

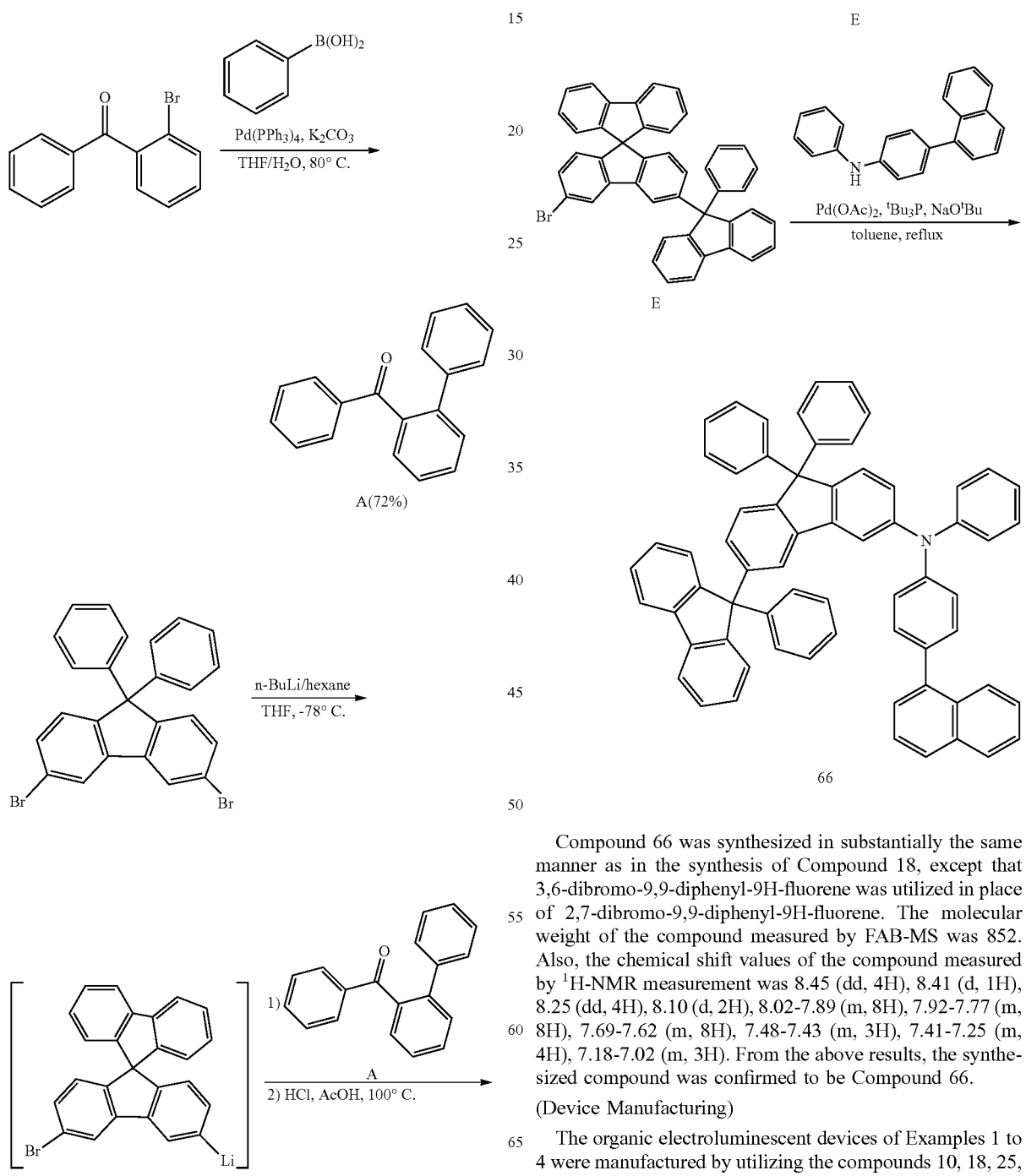

Compound 66 was synthesized in substantially the same manner as in the synthesis of Compound 18, except that 3,6-dibromo-9,9-diphenyl-9H-fluorene was utilized in place of 2,7-dibromo-9,9-diphenyl-9H-fluorene. The molecular weight of the compound measured by FAB-MS was 852. Also, the chemical shift values of the compound measured by $^1$H-NMR measurement was 8.45 (dd, 4H), 8.41 (d, 1H), 8.25 (dd, 4H), 8.10 (d, 2H), 8.02-7.89 (m, 8H), 7.92-7.77 (m, 8H), 7.69-7.62 (m, 8H), 7.48-7.43 (m, 3H), 7.41-7.25 (m, 4H), 7.18-7.02 (m, 3H). From the above results, the synthesized compound was confirmed to be Compound 66.

(Device Manufacturing)

The organic electroluminescent devices of Examples 1 to 4 were manufactured by utilizing the compounds 10, 18, 25, and 66 described above as a hole transfer layer material.

Example Compounds
Comparative Example Compounds
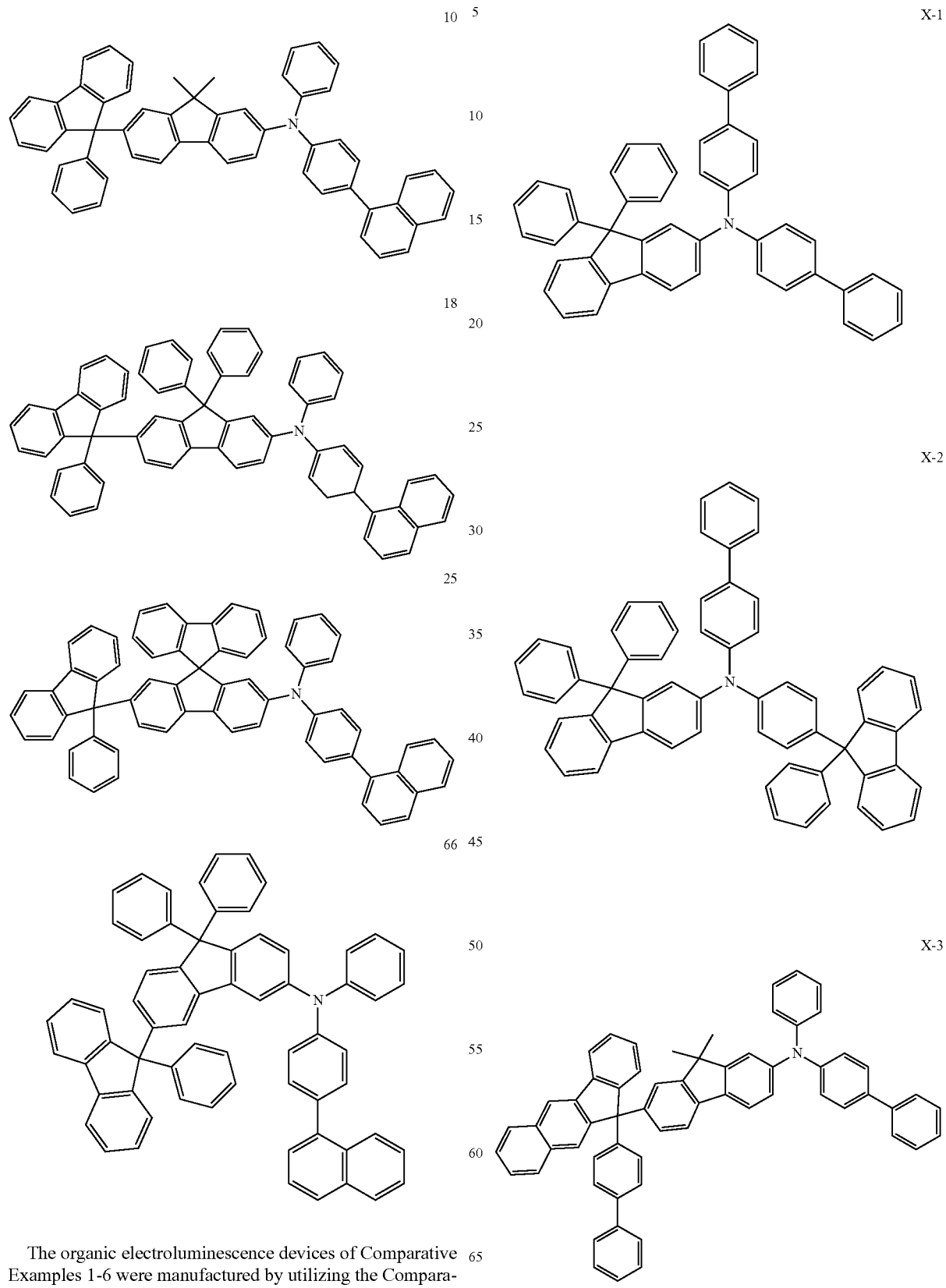
The organic electroluminescence devices of Comparative Examples 1-6 were manufactured by utilizing the Comparative Examples X-1 to X-6 as the hole transfer layer material.

-continued

X-4

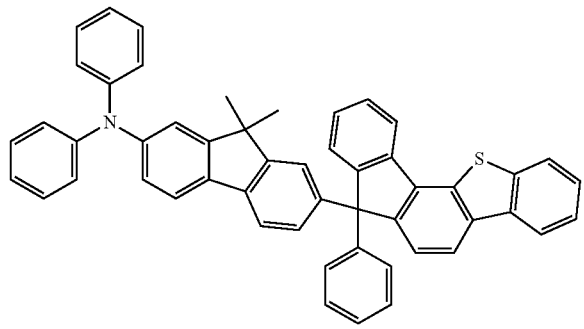

X-5

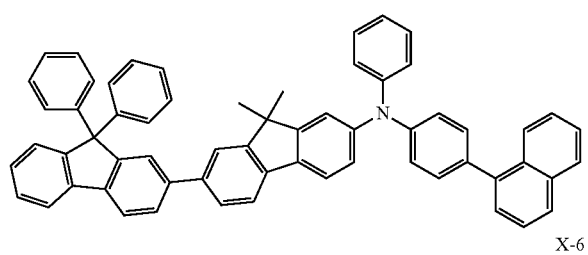

X-6

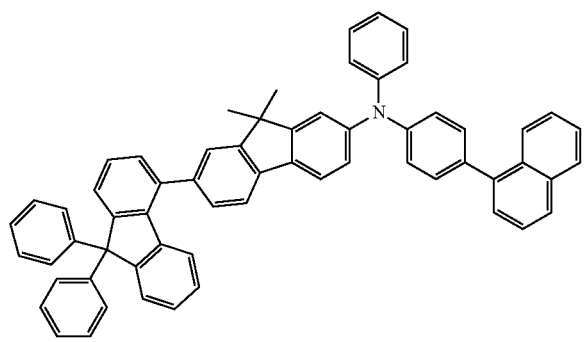

The organic electroluminescent devices of Examples 1 to 4 and Comparative Examples 1 to 6 were provided with: a first electrode having a thickness of 150 nm utilizing ITO; a hole injection layer having a thickness of 60 nm utilizing TNATA (4,4',4''-Tris[2-naphthyl(phenyl)amino]triphenylamine); a hole transfer layer having a thickness of 30 nm utilizing the respective example compounds or comparative example compounds; a light emitting layer having a thickness of 25 nm including 3% of TBP (2,5,8,11-Tetra-tert-butylperylene) doped in ADN (dinaphthylthracene); an electron transfer layer having a thickness of 25 nm utilizing $Alq_3$; an electron injection layer having a thickness of 1 nm utilizing LiF; and a second electrode having a thickness of 100 nm utilizing Al. Each layer was formed by a deposition method under a vacuum atmosphere.

Experimental Example

The driving voltage and lifetime of the organic electroluminescent devices manufactured with Example Compounds 10, 18, 25, 66 and Comparative Example Compounds X-1 to X-6 were evaluated. The evaluation results are illustrated in Table 1 below. The driving voltage in each of the Examples and the Comparative Examples was measured at a current density of 10 mA/cm$^2$, and the lifetime was measured as the time it took for the luminance to reduce to half from an initial luminance of 1000 cd/m$^2$.

TABLE 1

| Device Preparation Example | Hole Transfer Layer | Driving Voltage (V) | Lifetime $LT_{50}$ (h) |
|---|---|---|---|
| Example 1 | Example Compound 10 | 5.4 | 1900 |
| Example 2 | Example Compound 18 | 5.5 | 2000 |
| Example 3 | Example Compound 25 | 5.6 | 1950 |
| Example 4 | Example Compound 66 | 5.6 | 1850 |
| Comparative Example 1 | Comparative Example Compound X-1 | 6.2 | 1400 |
| Comparative Example 2 | Comparative Example Compound X-2 | 6.5 | 1450 |
| Comparative Example 3 | Comparative Example Compound X-3 | 6.2 | 1500 |
| Comparative Example 4 | Comparative Example Compound X-4 | 6.4 | 1500 |
| Comparative Example 5 | Comparative Example Compound X-5 | 6.5 | 1500 |
| Comparative Example 6 | Comparative Example Compound X-6 | 6.4 | 1550 |

Referring to the results of Table 1, it may be seen that the driving voltages of Examples 1 to 4 were lower than those of Comparative Examples 1-6, and the lifetime of the corresponding device was improved. In Examples 1 to 4, an amine compound containing a bifluorenyl group was included in the hole transfer layer to improve heat resistance and charge resistance while maintaining the characteristics of amine, thereby reducing the deterioration of characteristics (e.g., performance) resulting from high temperatures and electric charges. Therefore, long lifetime has been achieved. Further, the planarity of the fluorenyl group strengthens the intermolecular interaction of the compound forming the hole transfer layer and improves the mobility of holes, thereby improving the hole transfer characteristics. Therefore, a low driving voltage is obtained.

Comparative Examples 1 and 2 include a fluorenyl group in each of Comparative Compounds X-1 and X-2 utilized in forming the hole transfer layer, but does not include a bifluorenyl group, thereby having low heat resistance and low charge resistance. Accordingly, the lifetime of the device is short and the driving voltage is high, compared to the devices manufactured according to the Examples. Comparative Examples 3 and 4 include bifluorene derivatives, but the bifluorenyl group has a condensed ring structure and has lower charge resistance than that of a general bifluorenyl group, thereby having short device lifetime and higher driving voltage. Comparative Example 5 includes a bifluorenyl group, but the resonance structure between the two fluorenyl groups is long, so that the LUMO (lowest unoccupied molecular orbital) of the compound becomes very low, and the electric charge balance is collapsed. Therefore, the lifetime of the device is short and the driving voltage is high. In Comparative Example 6, a bond is provided at No. 4 carbon position of the second fluorenyl group, and the bond is easily broken due to the increased volume. Therefore, the lifetime of the device is shortened.

Although the exemplary embodiments of the present invention have been described with reference to the accompanying drawings, it is understood that the present invention should not be limited to these exemplary embodiments but various suitable changes and modifications can be made by one ordinary skilled in the art within the spirit and scope of the present invention as hereinafter claimed, and equivalents thereof. It is therefore to be understood that the previous embodiments are illustrative and non-restrictive in every respect.

68
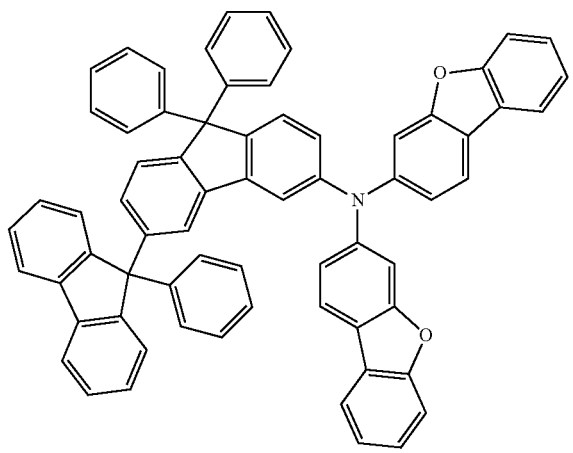
71
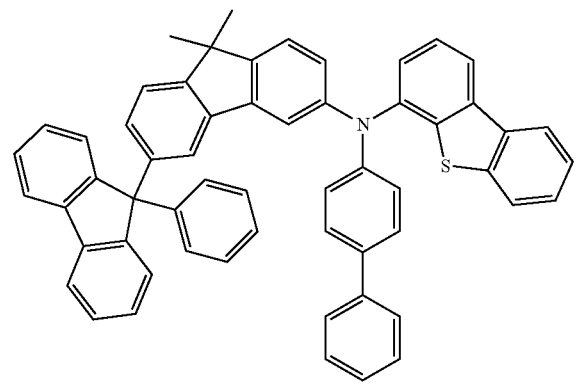
69
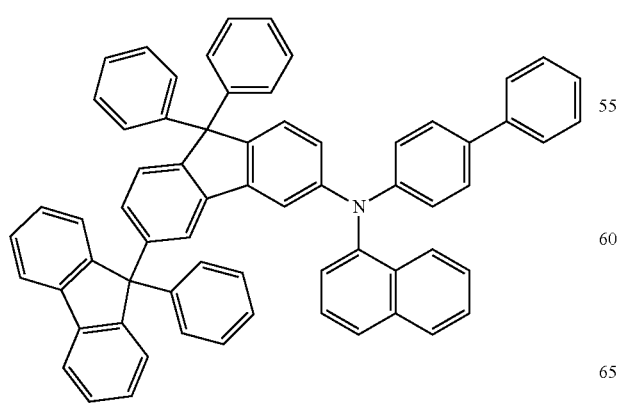
72
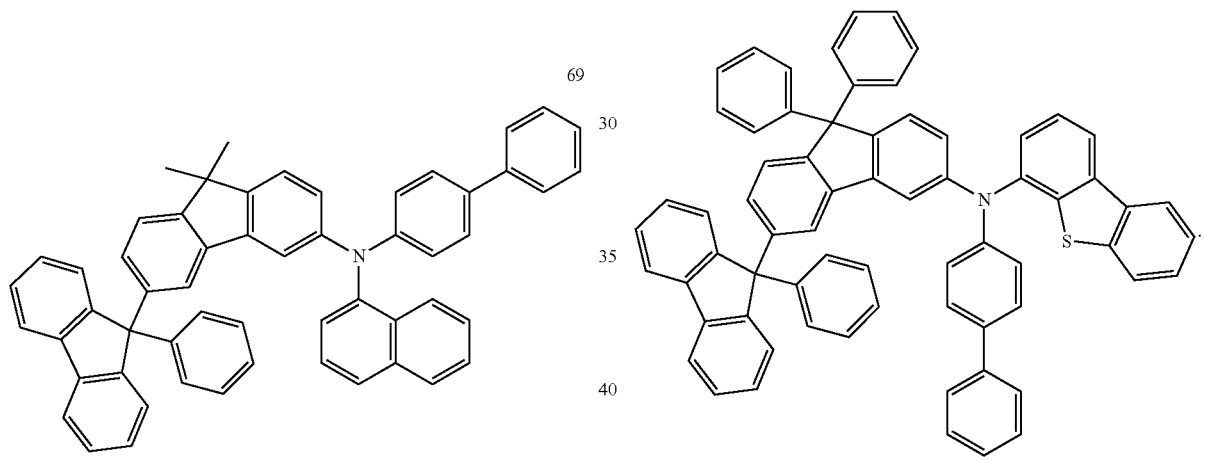
19. The organic electroluminescence device of claim 10, wherein the amine compound represented by Formula 1 is any one selected from the compounds represented by Compound Group 3 below:
Compound Group 3
70
73
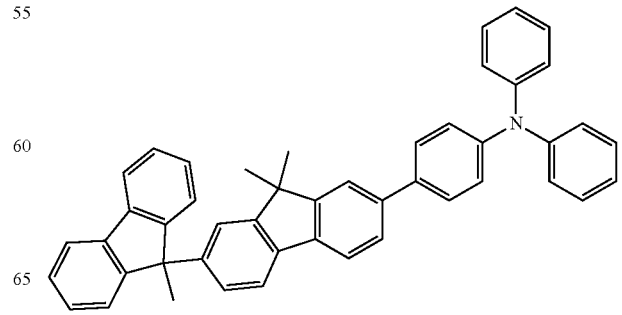

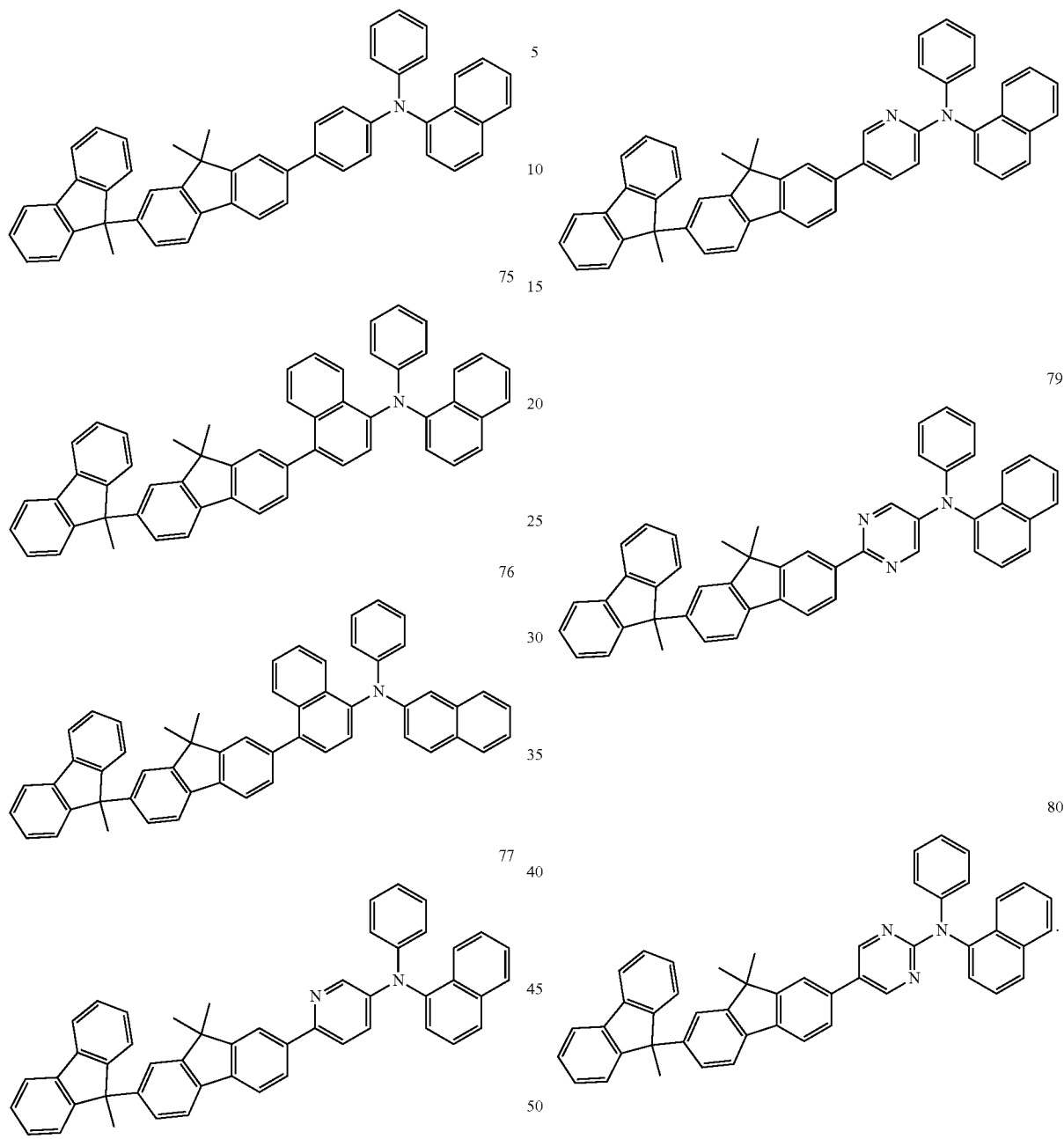

What is claimed is:

1. An amine compound represented by Formula 1 below:

[Formula 1 structure]

wherein in Formula 1, $Ar_1$ and $Ar_2$ are each independently a substituted or unsubstituted aryl group having 6 to 30 carbon atoms for forming a ring or a substituted or unsubstituted heteroaryl group having 2 to 30 carbon atoms for forming a ring;

L is a direct linkage, a substituted or unsubstituted arylene group having 6 to 30 carbon atoms for forming a ring, or a substituted or unsubstituted heteroarylene group having 2 to 30 carbon atoms for forming a ring;

$R_1$ to $R_7$ are each independently hydrogen, deuterium, a halogen atom, a substituted or unsubstituted alkyl group having 1 to 20 carbon atoms, a substituted or unsubstituted aryl group having 6 to 30 carbon atoms for forming a ring, or a substituted or unsubstituted heteroaryl group having 2 to 30 carbon atoms for forming a ring; and $R_1$ and $R_2$ optionally combine with each other to form a ring;

a and b are each independently an integer of 0 to 3; and c and d are each independently an integer of 0 to 4.

2. The amine compound of claim 1, wherein the amine compound represented by Formula 1 is represented by Formula 2-1 below:

[Formula 2-1 structure]

wherein in Formula 2-1, $Ar_1$, $Ar_2$, L, $R_1$ to $R_7$, and a to d are the same as defined in Formula 1.

3. The amine compound of claim 1, wherein the amine compound represented by Formula 1 is represented by Formula 2-2 below:

[Formula 2-2 structure]

wherein in Formula 2-2, $Ar_1$, $Ar_2$, L, $R_1$ to $R_7$, and a to d are the same as defined in Formula 1.

4. The amine compound of claim 1, wherein $Ar_1$ and $Ar_2$ are each independently a substituted or unsubstituted phenyl group, a substituted or unsubstituted biphenyl group, a substituted or unsubstituted naphthyl group, a substituted or unsubstituted dibenzofuranyl group, or a substituted or unsubstituted dibenzothiophenyl group.

5. The amine compound of claim 1, wherein $R_1$ and $R_2$ are each independently a methyl group, a substituted or unsubstituted phenyl group, or combine with each other to form a ring.

6. The amine compound of claim 1, wherein the amine compound represented by Formula 1 is represented by any one selected from Formulae 3-1 to 3-3:

[Formula 3-1 structure]

[Formula 3-2 structure]

Formula 3-3
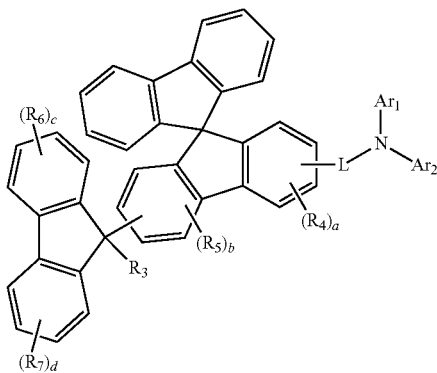
wherein in Formulae 3-1 to 3-3,
Ar$_1$, Ar$_2$, L, R$_3$ to R$_7$, and a to d are the same as defined in Formula 1.
7. The amine compound of claim 1,
wherein the amine compound represented by Formula 1 is any one selected from the compounds represented by Compound Group 1 below,
Compound Group 1
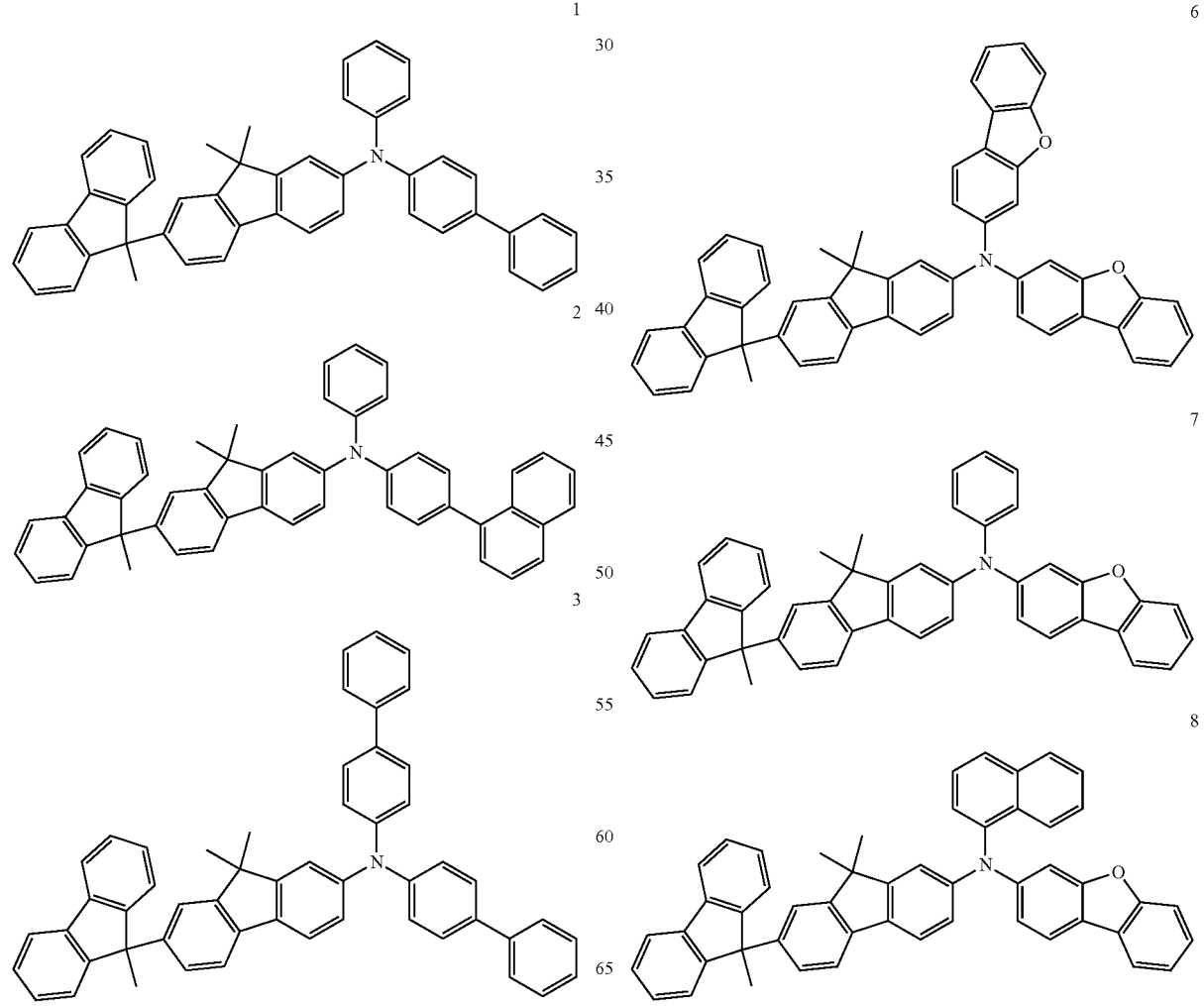
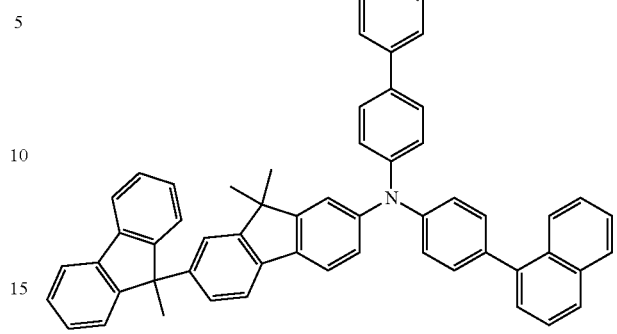

9
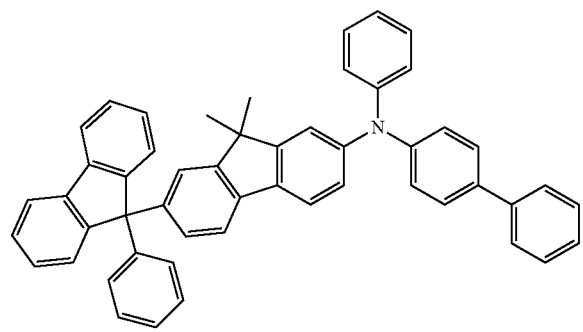
10
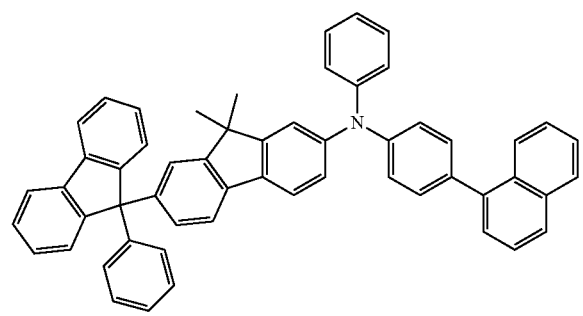
11
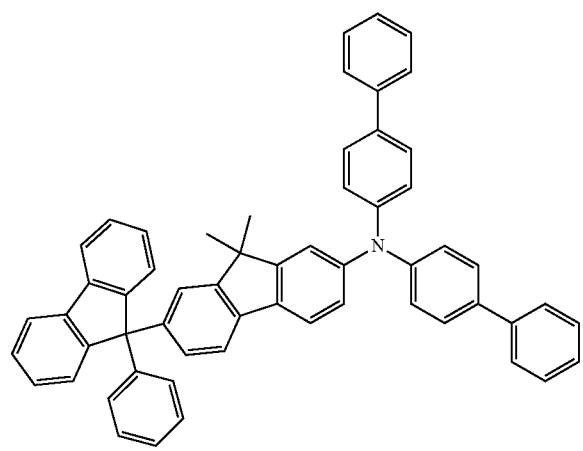
12
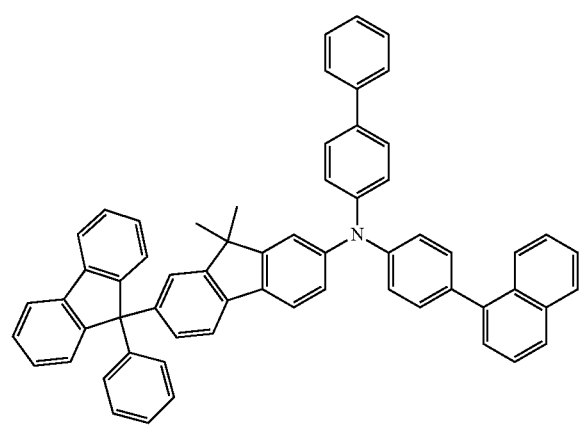
13
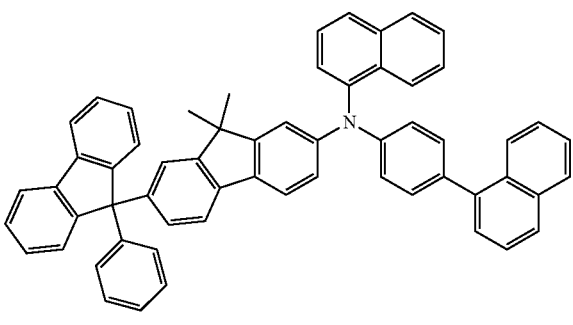
14
15
16
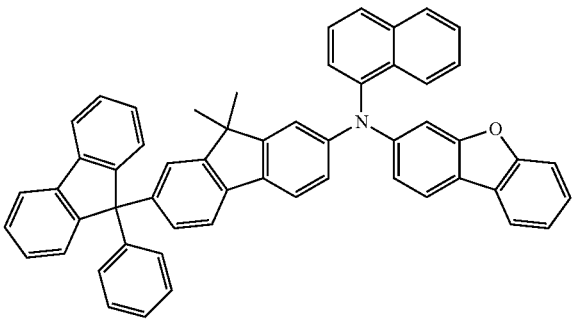

17
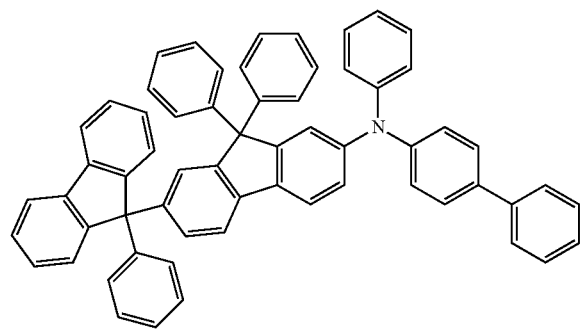
18
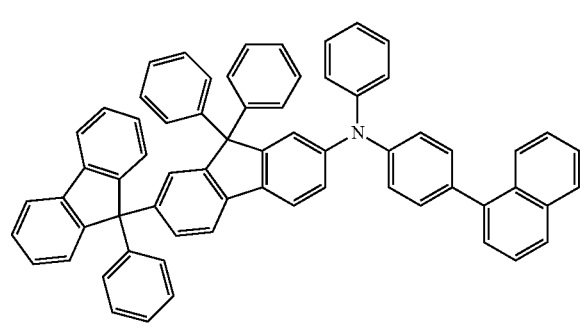
19
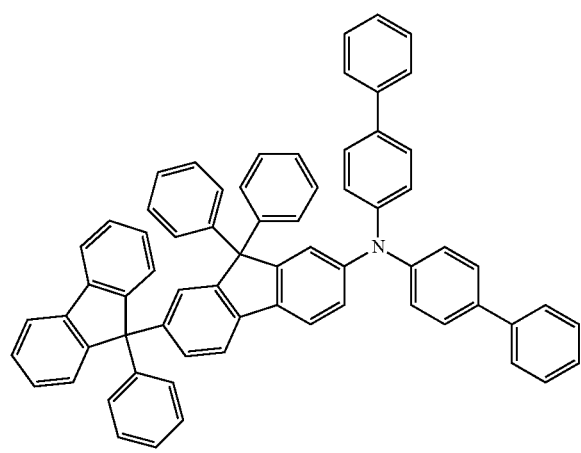
20
21
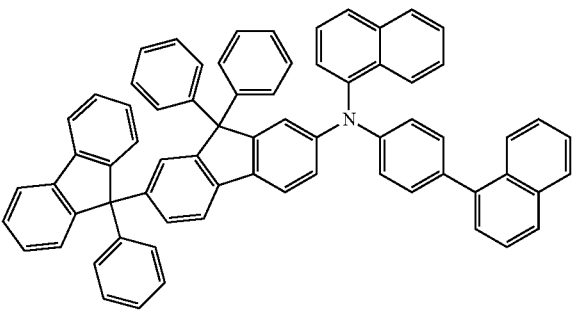
22
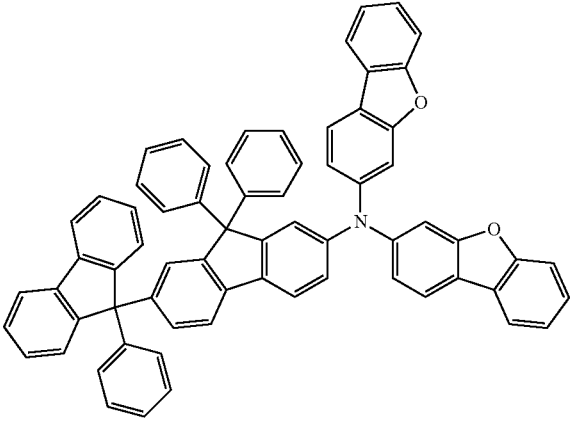
23
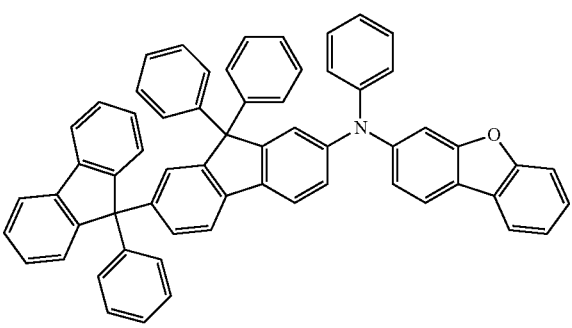
24
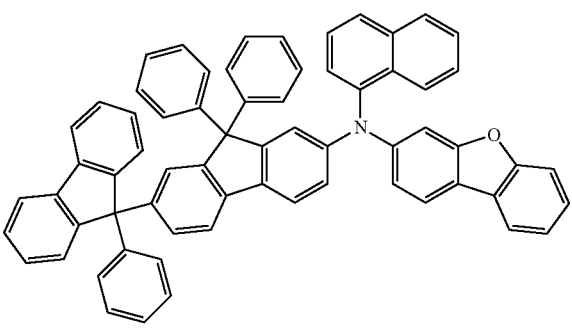

25
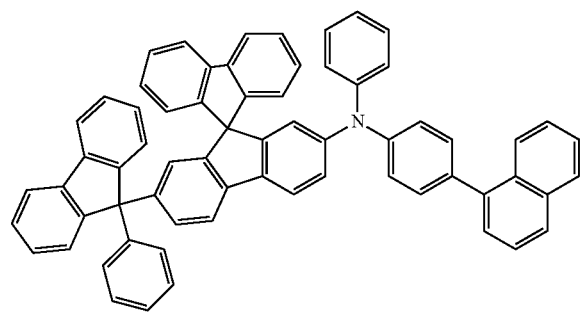
26
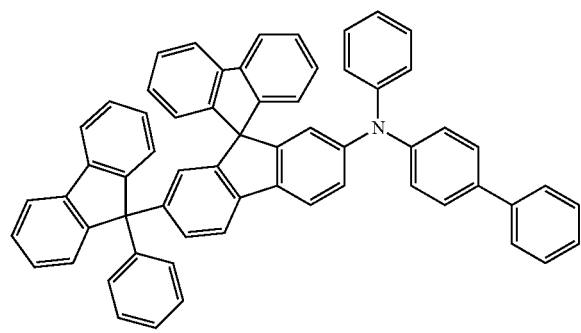
27
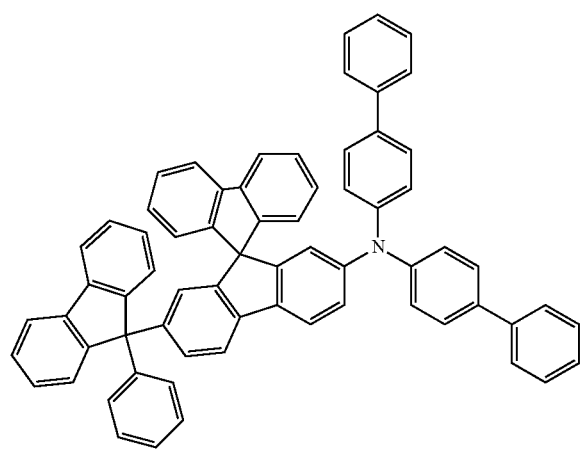
28
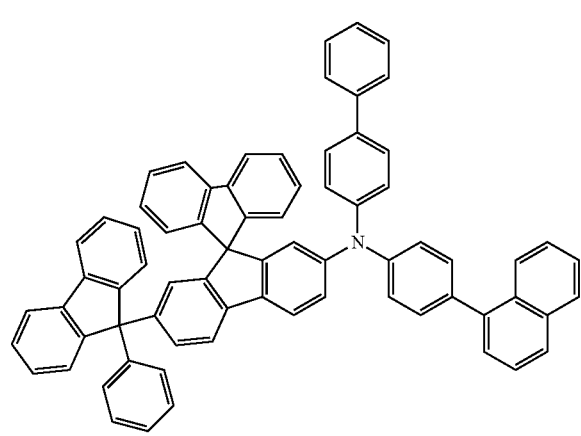
29
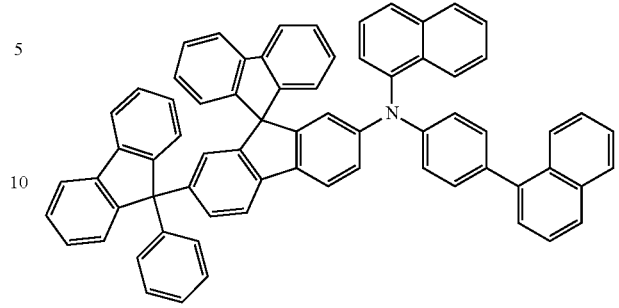
30
31
32
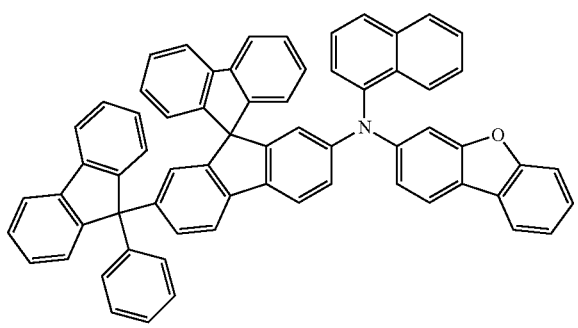

33
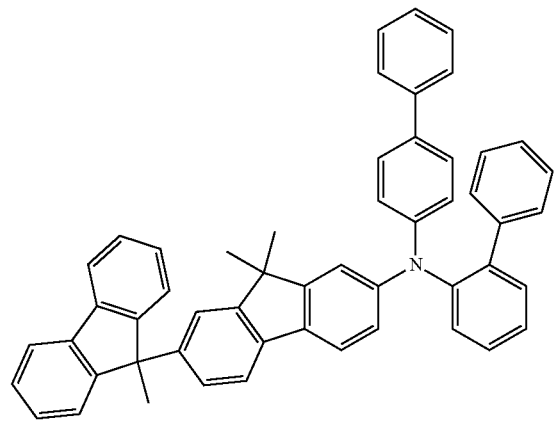
34
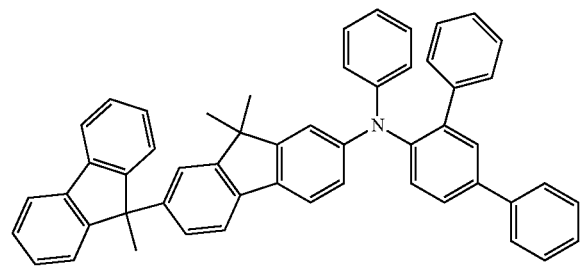
35
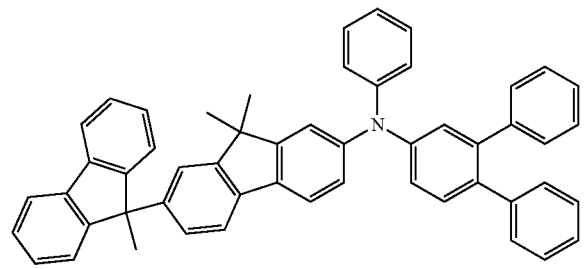
36
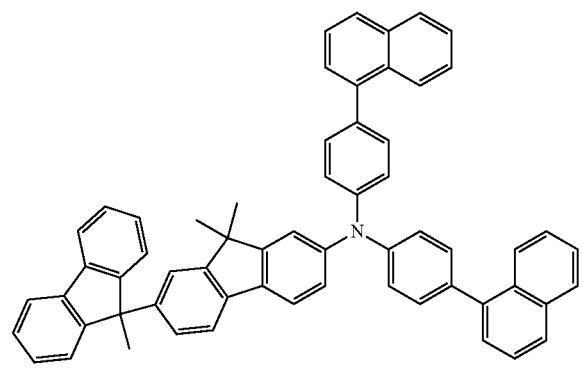
37
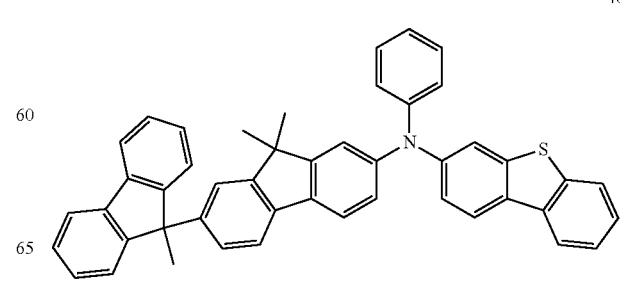

-continued
41
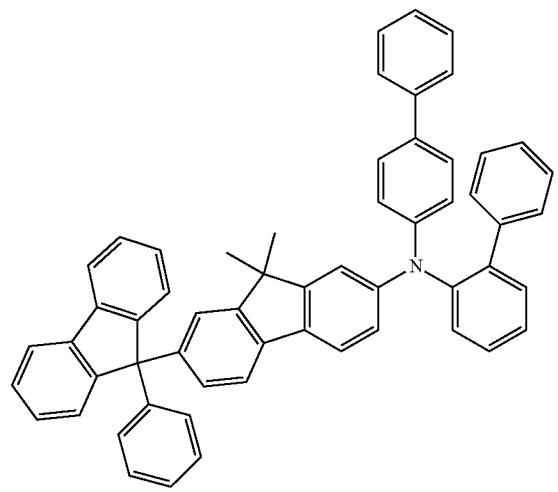
42
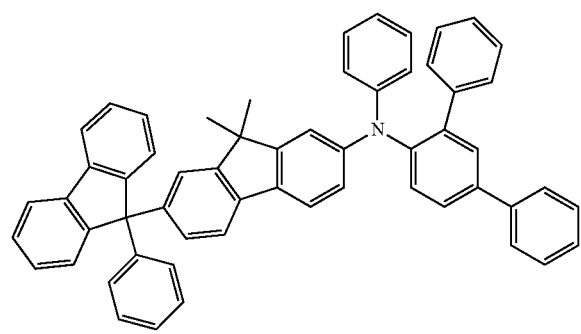
43
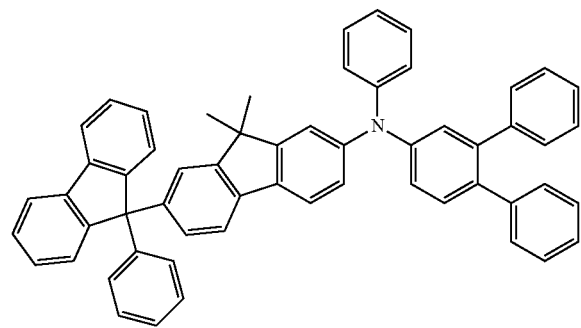
44
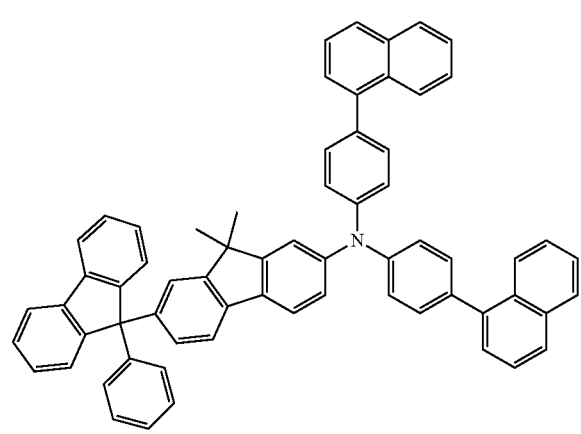
-continued
45
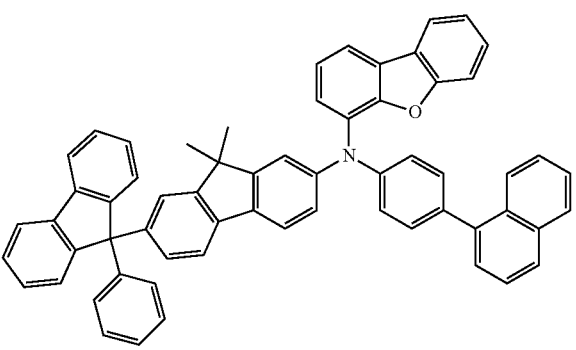
46
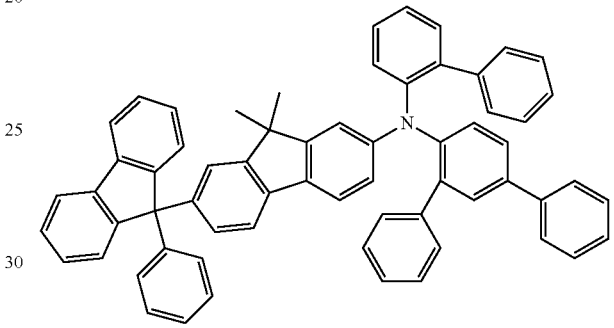
47
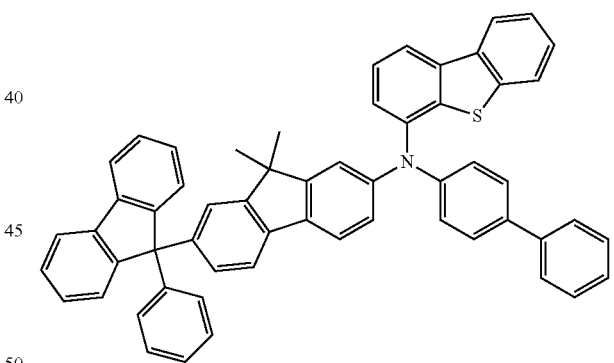
48
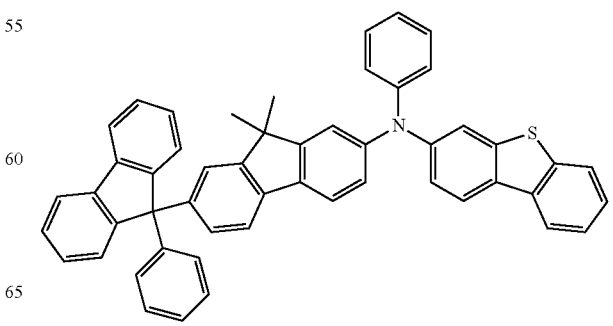

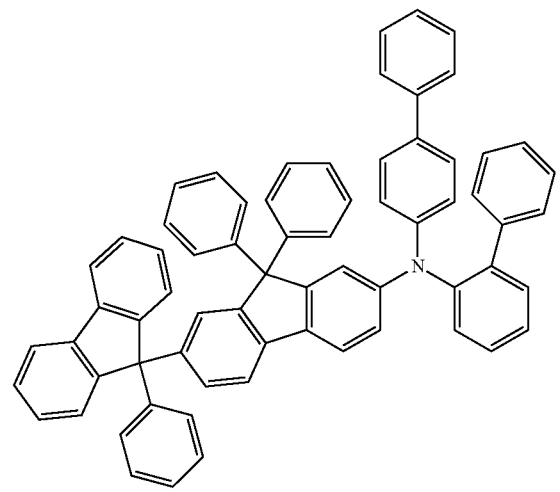
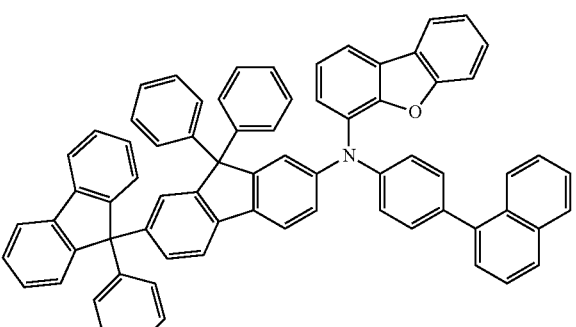

57
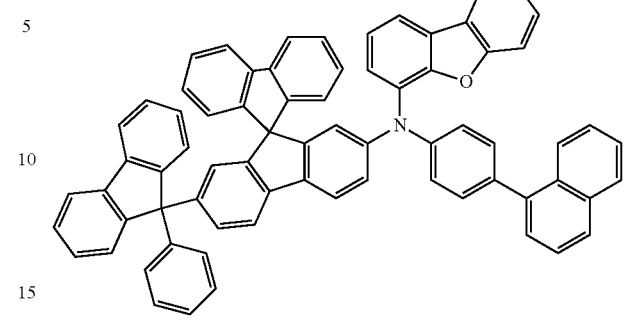
58
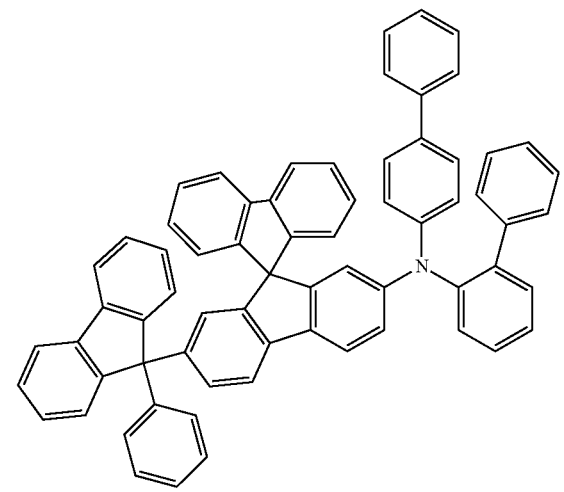
59
61
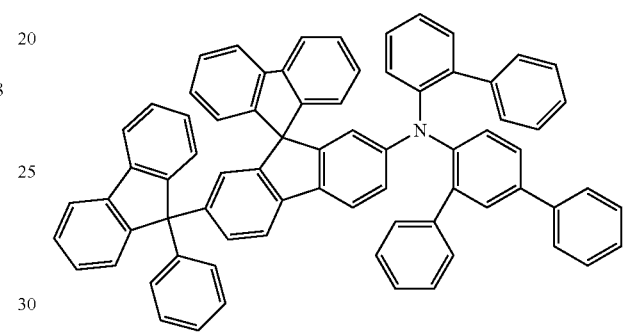
62
63
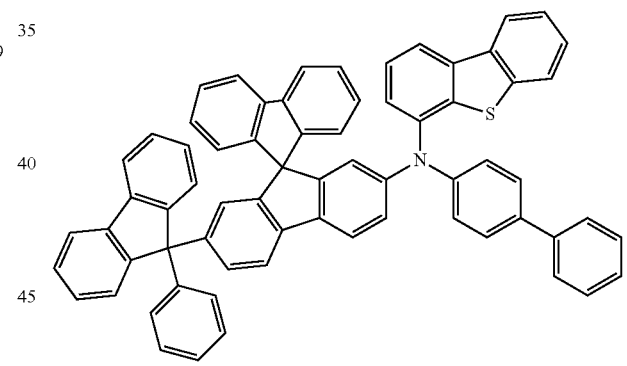
64
60
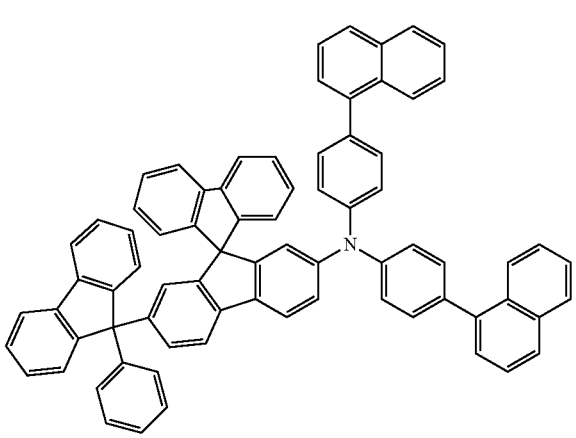
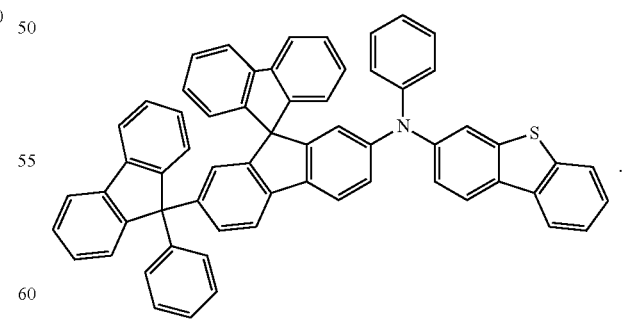
8. The amine compound of claim 1, wherein the amine compound represented by Formula 1 is any one selected from the compounds represented by Compound Group 2 below:

Compound Group 2
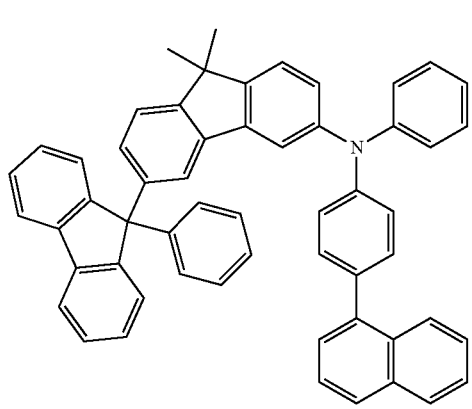
65
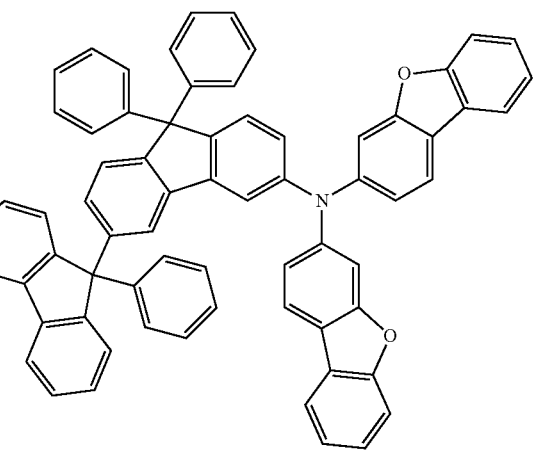
68
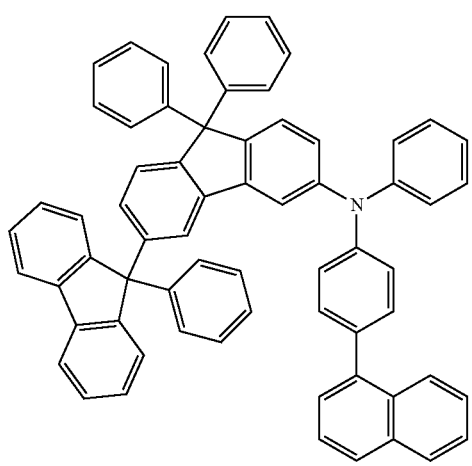
66
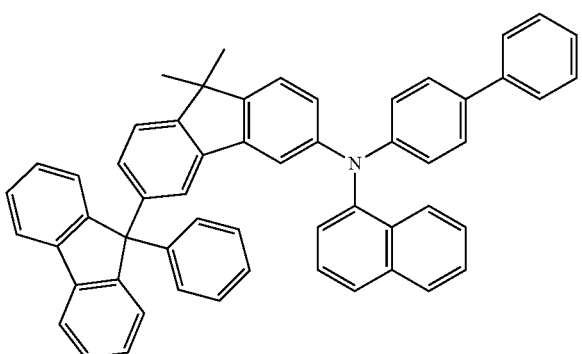
69
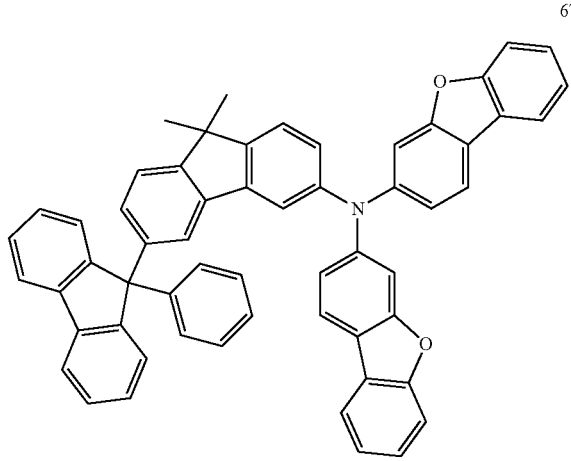
67
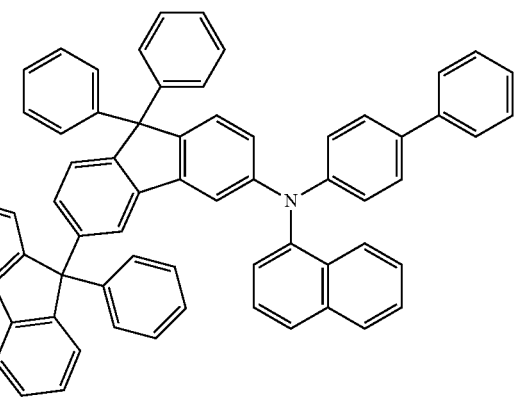
70

73
-continued
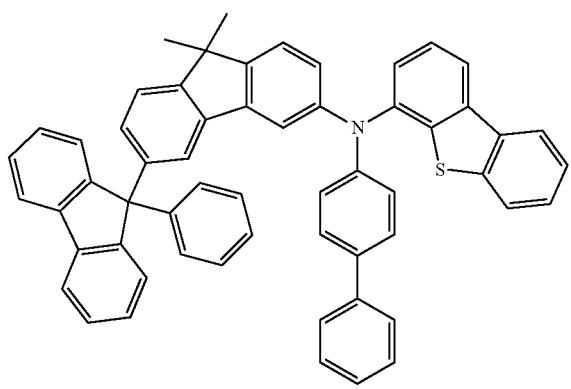
71
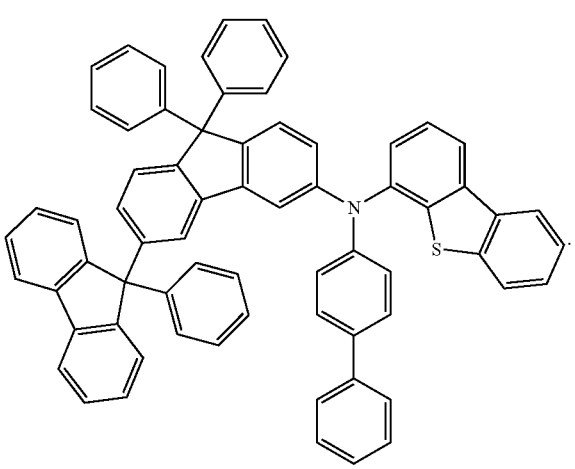
72
9. The amine compound of claim 1,
   wherein the amine compound represented by Formula 1 is any one selected from the compounds represented by Compound Group 3 below:
Compound Group 3
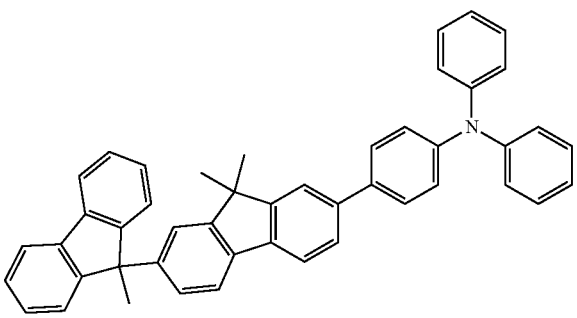
73
74
-continued
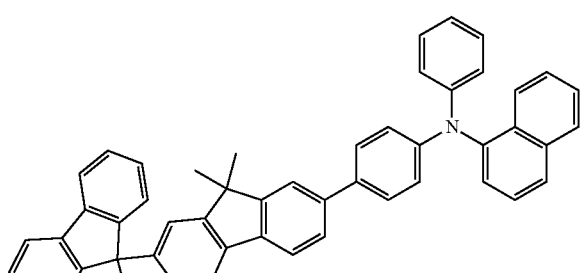
74
75
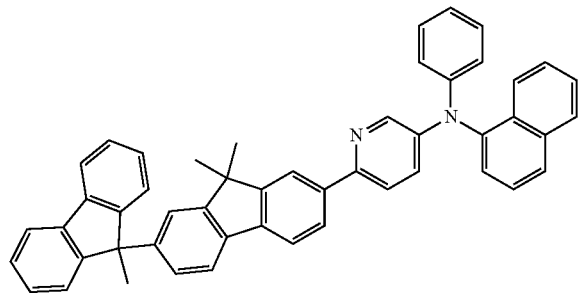
76
77
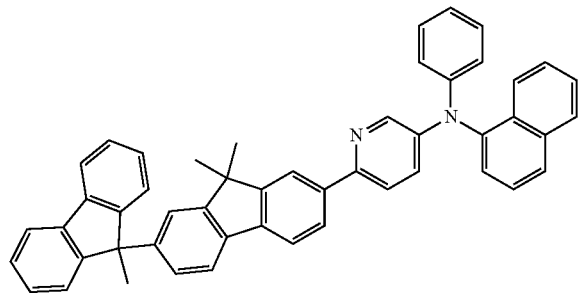
78

-continued

79

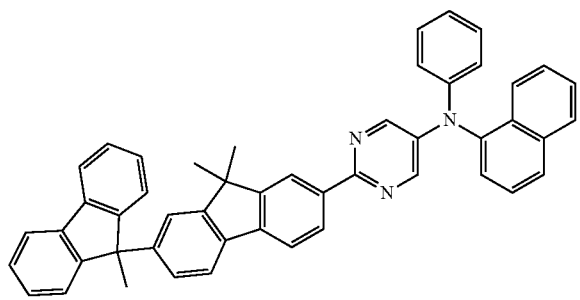

80

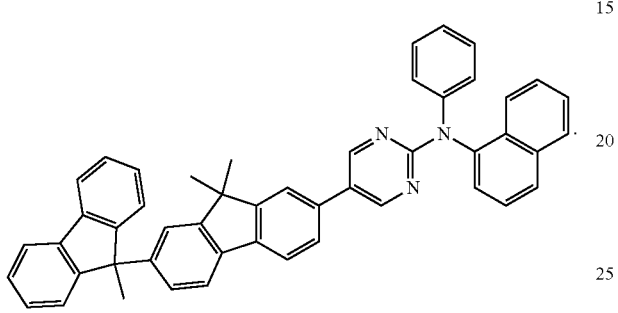

10. An organic electroluminescence device comprising:
a first electrode;
a hole transfer region on the first electrode;
a light emitting layer on the hole transfer region;
an electron transfer layer on the light emitting layer; and
a second electrode on the electron transfer layer,
wherein the hole transfer region comprises an amine compound represented by Formula 1 below:

Formula 1

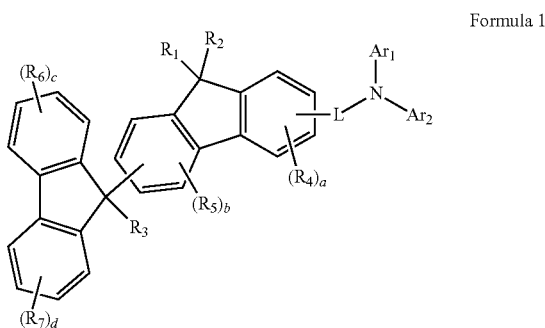

wherein in Formula 1,
Ar$_1$ and Ar$_2$ are each independently a substituted or unsubstituted aryl group having 6 to 30 carbon atoms for forming a ring, a substituted or unsubstituted heteroaryl group having 2 to 30 carbon atoms for forming a ring;
L is a direct linkage, a substituted or unsubstituted arylene group having 6 to 30 carbon atoms for forming a ring, or a substituted or unsubstituted heteroarylene group having 2 to 30 carbon atoms for forming a ring;
R$_1$ to R$_7$ are each independently hydrogen, deuterium, a halogen atom, a substituted or unsubstituted alkyl group having 1 to 20 carbon atoms, a substituted or unsubstituted aryl group having 6 to 30 carbon atoms for forming a ring, or a substituted or unsubstituted heteroaryl group having 2 to 30 carbon atoms for forming a ring; and R$_1$ and R$_2$ optionally combine with each other to form a ring;
a and b are each independently an integer of 0 to 3; and
c and d are each independently an integer of 0 to 4.

11. The organic electroluminescence device of claim 10, wherein the hole transfer region comprises:
a hole injection layer on the first electrode; and
a hole transfer layer on the hole injection layer, the hole transfer layer comprising the amine compound represented by Formula 1.

12. The organic electroluminescence device of claim 10, wherein the amine compound represented by Formula 1 is represented by Formula 2-1:

Formula 2-1

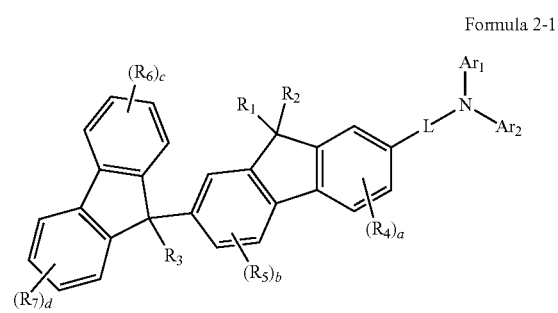

wherein in Formula 2-1,
Ar$_1$, Ar$_2$, L, R$_1$ to R$_7$, and a to d are the same as defined in Formula 1.

13. The organic electroluminescence device of claim 10, wherein the amine compound represented by Formula 1 is represented by Formula 2-2:

Formula 2-2

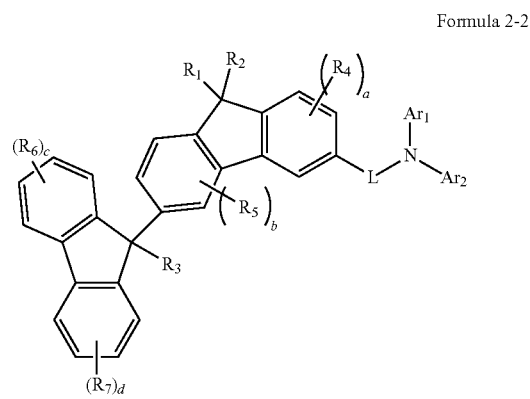

wherein in Formula 2-2,
Ar$_1$, Ar$_2$, L, R$_1$ to R$_7$, and a to d are the same as defined in Formula 1.

14. The organic electroluminescence device of claim 10, wherein Ar$_1$ and Ar$_2$ are each independently a substituted or unsubstituted phenyl group, a substituted or unsubstituted biphenyl group, a substituted or unsubstituted naphthyl group, a substituted or unsubstituted dibenzofuranyl group, or a substituted or unsubstituted dibenzothiophenyl group.

15. The organic electroluminescence device of claim 10, wherein R$_1$ and R$_2$ are each independently a methyl group, a substituted or unsubstituted phenyl group, or combine with each other to form a ring.

16. The organic electroluminescence device of claim 10, wherein the amine compound represented by Formula 1 is represented by any one of Formulae 3-1 to 3-3:

Formula 3-1
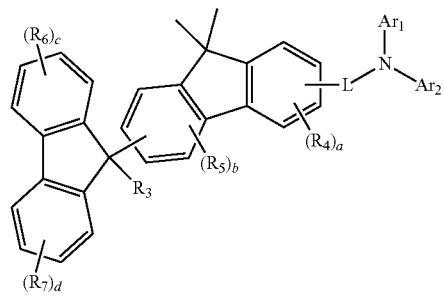

Formula 3-2
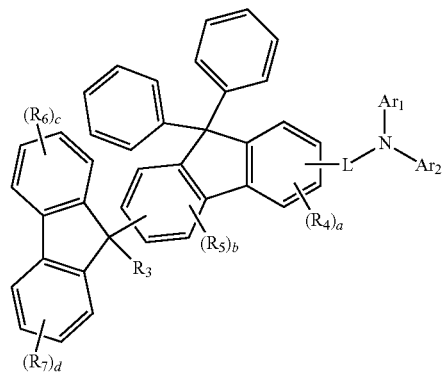

Formula 3-3
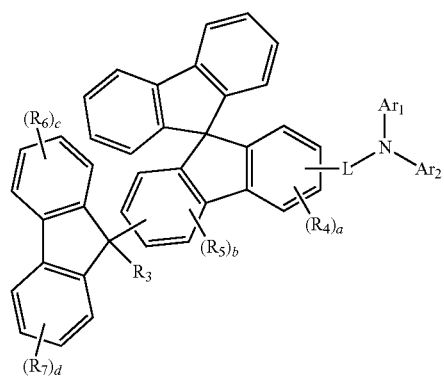

wherein in Formulae 3-1 to 3-3,

Ar$_1$, Ar$_2$, L, R$_4$ to R$_7$, L, and a to d are the same as defined in Formula 1.

17. The organic electroluminescence device of claim 10, wherein the amine compound represented by Formula 1 is any one selected from the compounds represented by Compound Group 1 below:

Compound Group 1

1
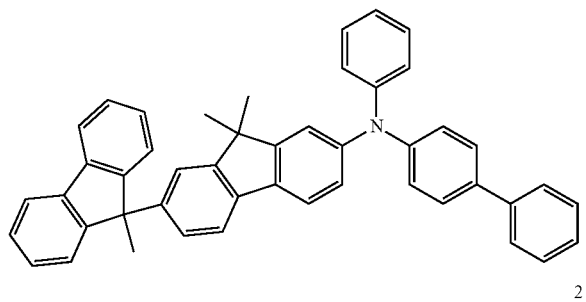

2

3
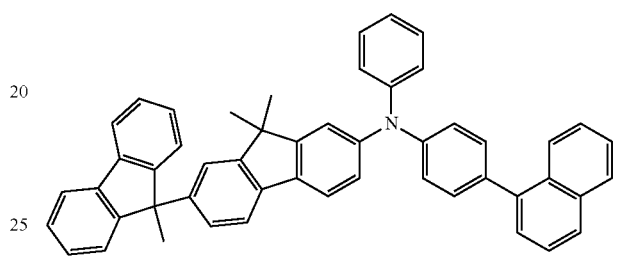

4
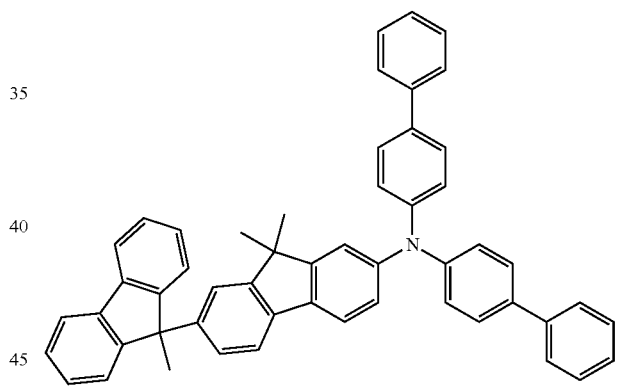

-continued
5
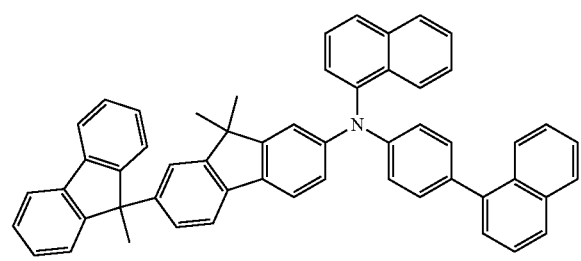
6
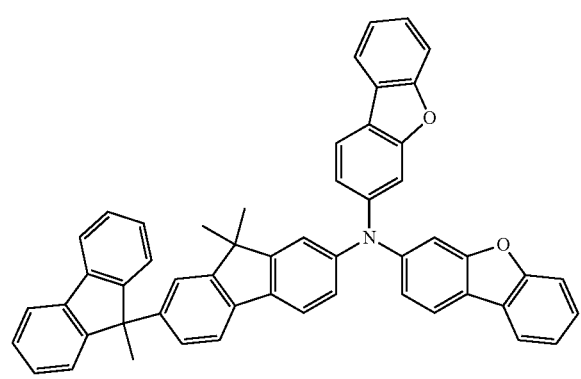
7
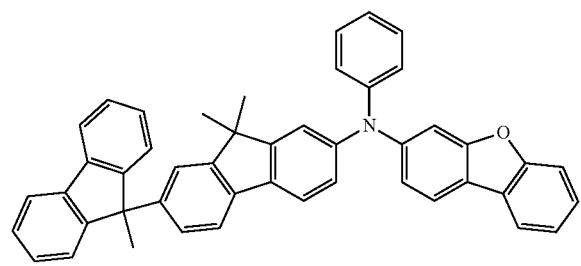
8
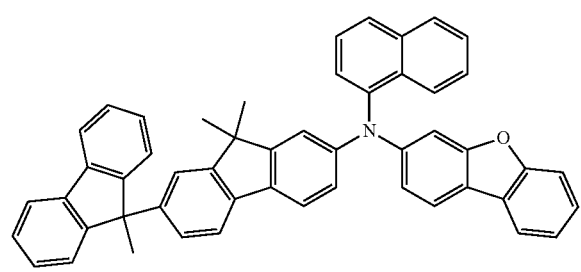
9
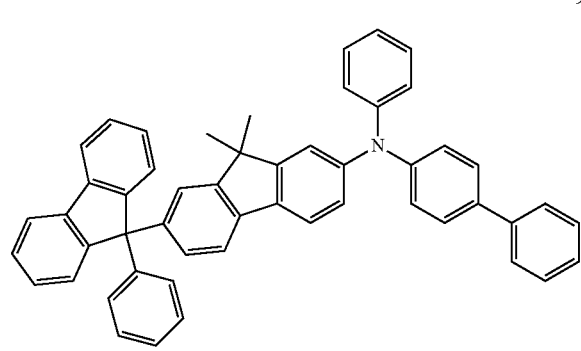
-continued
10
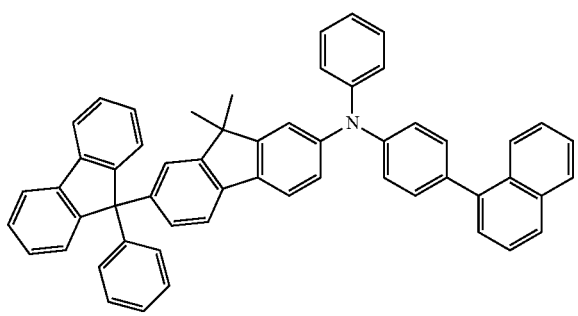
11
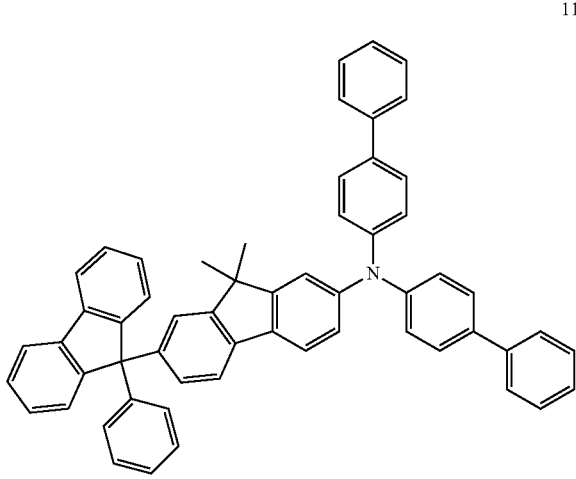
12
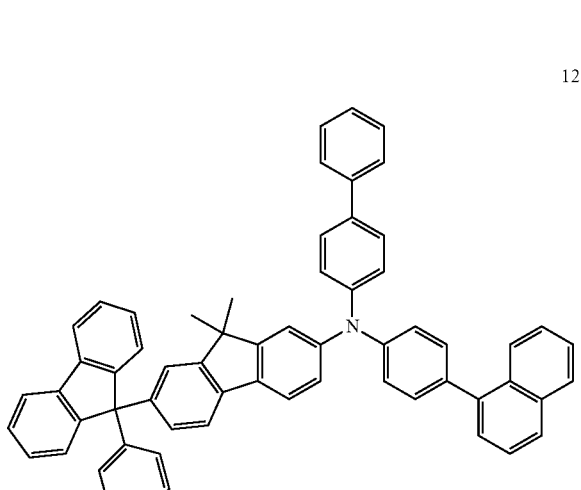
13
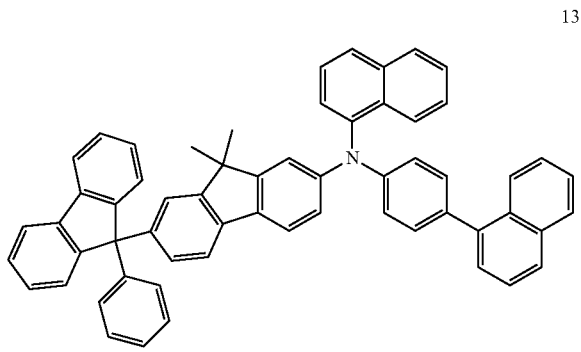

14
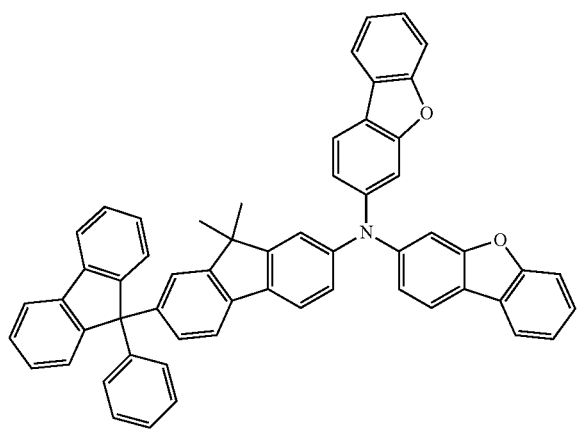
15
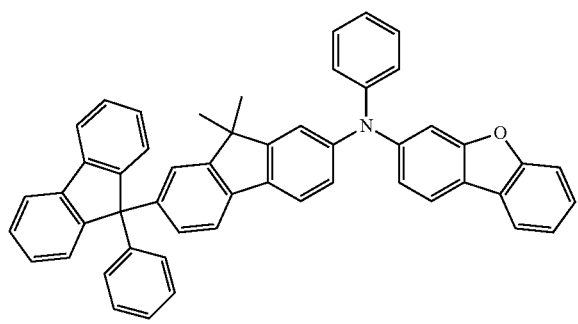
16
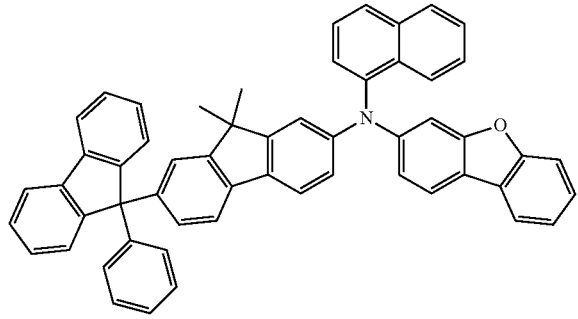
33
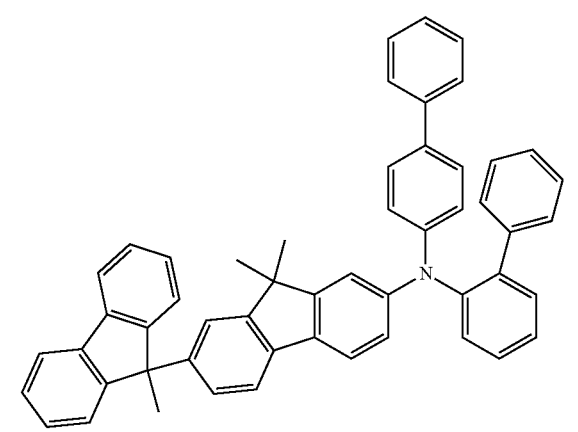
34
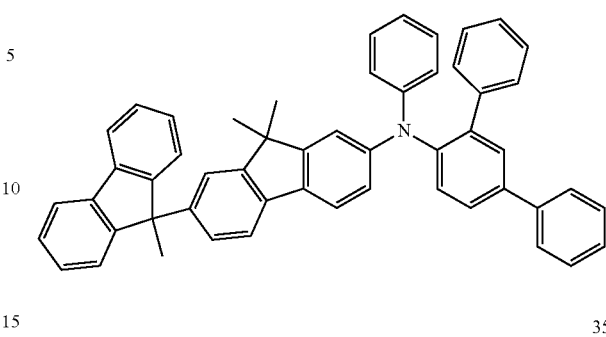
35
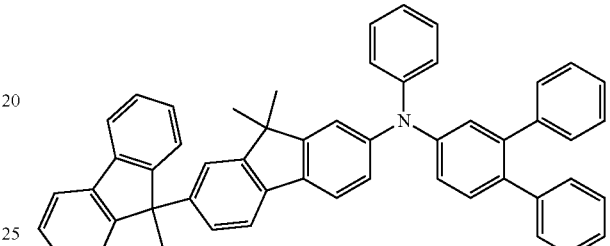
36
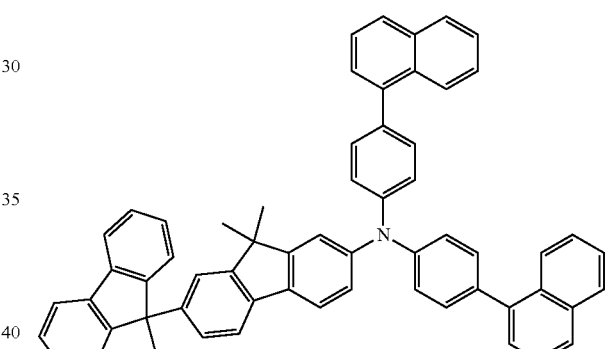
37
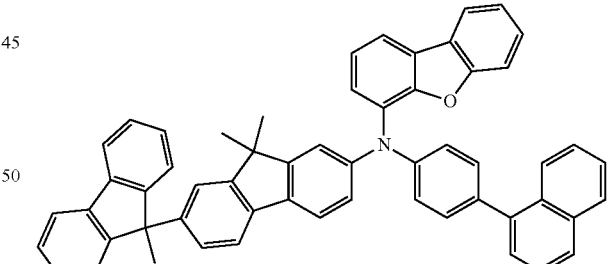
38
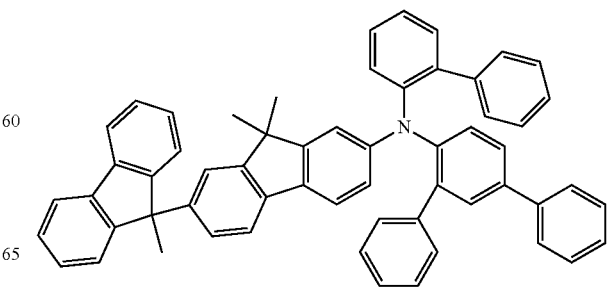

39
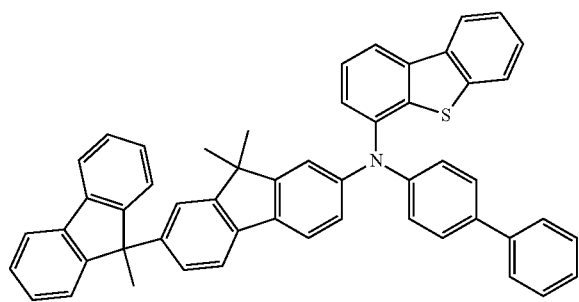
40
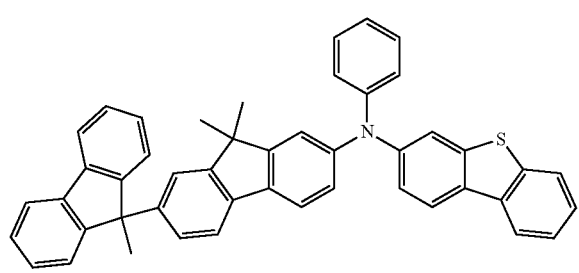
41
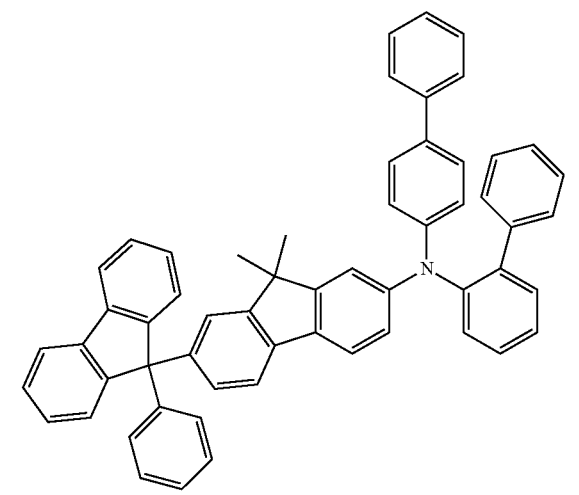
42
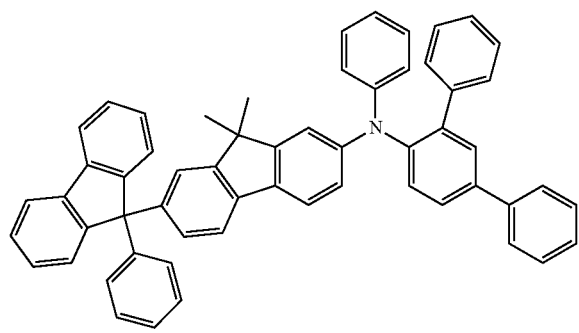
43
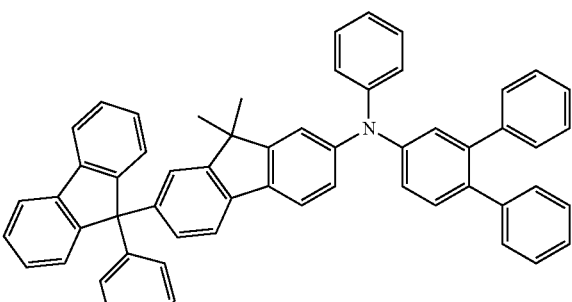
44
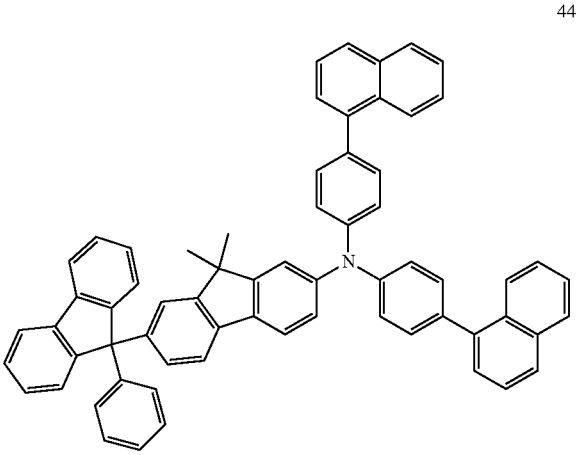
45
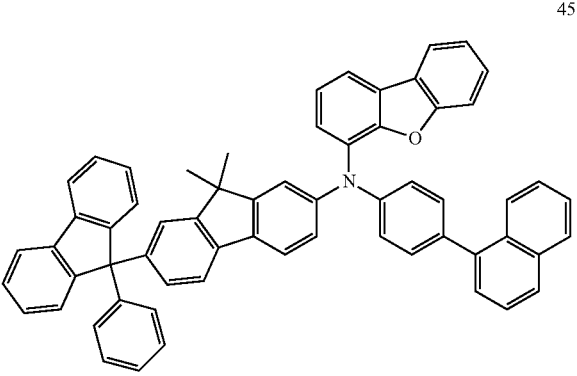
46
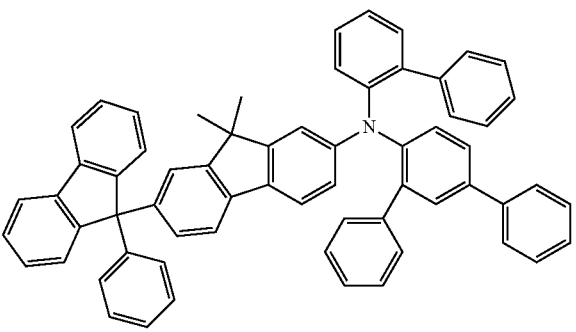

47
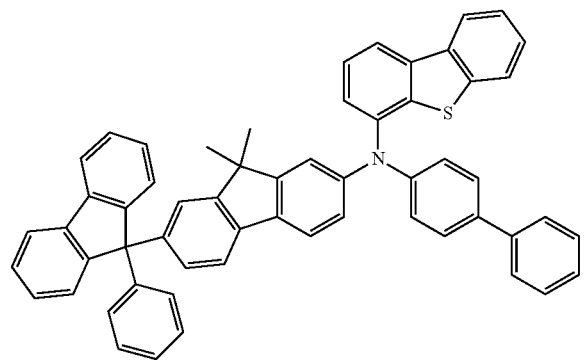
48
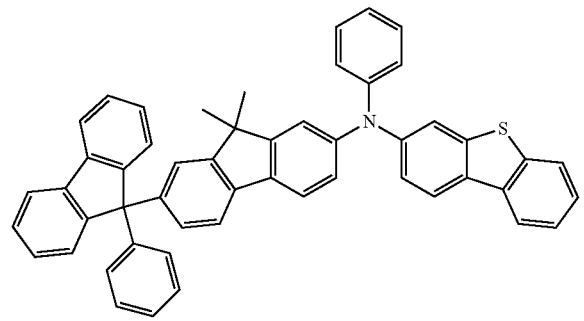
17
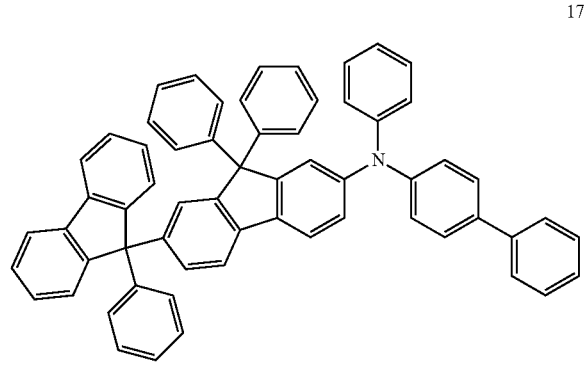
18
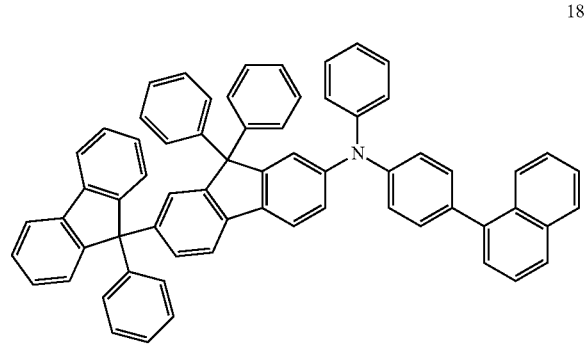
19
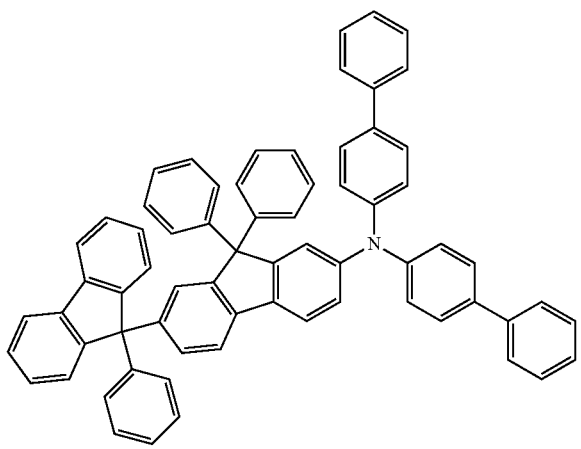
20
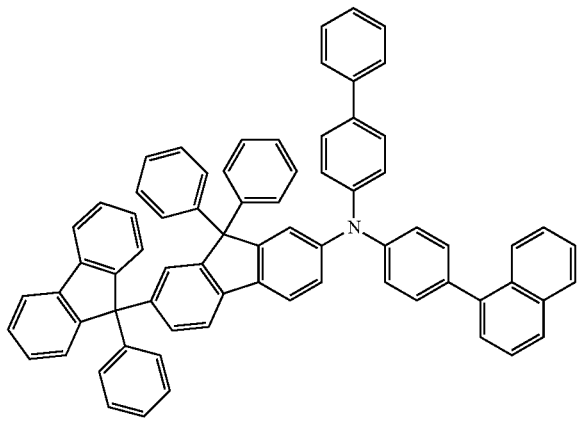
21
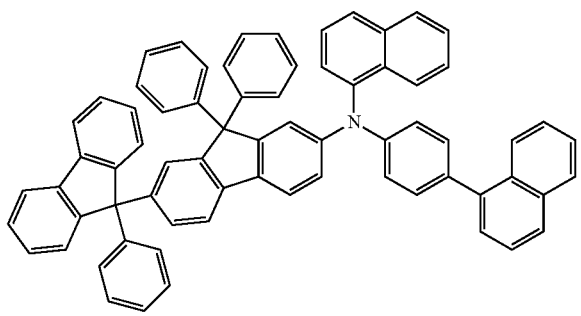

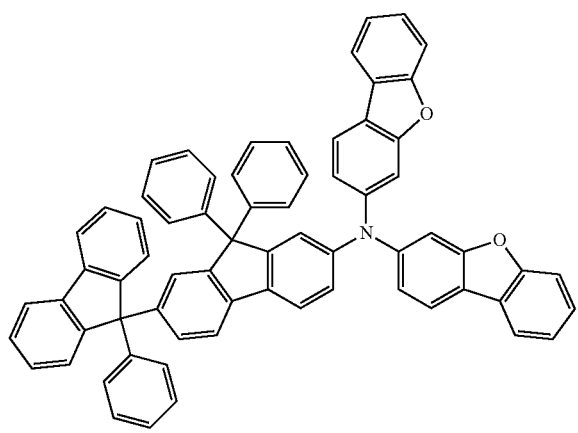
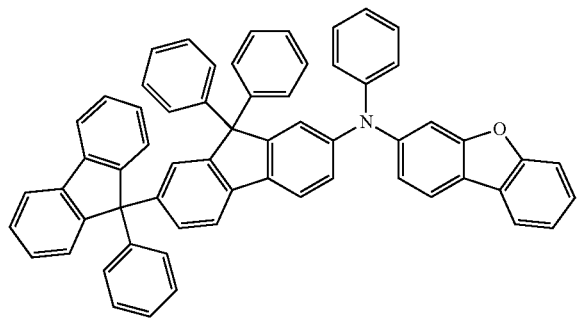
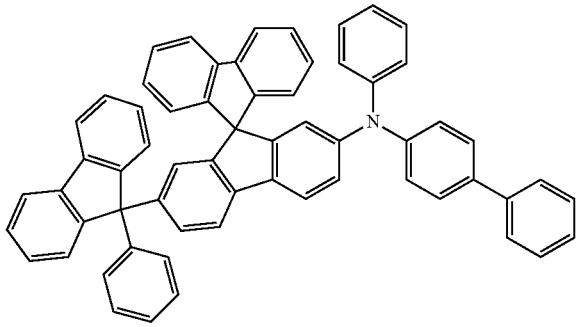
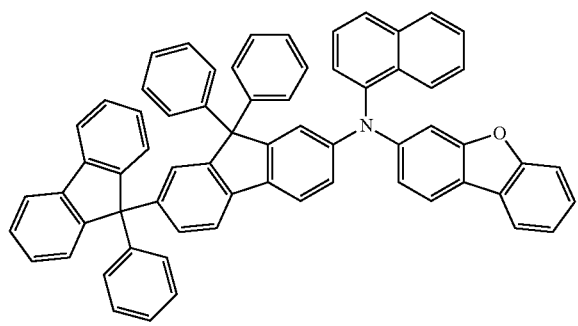
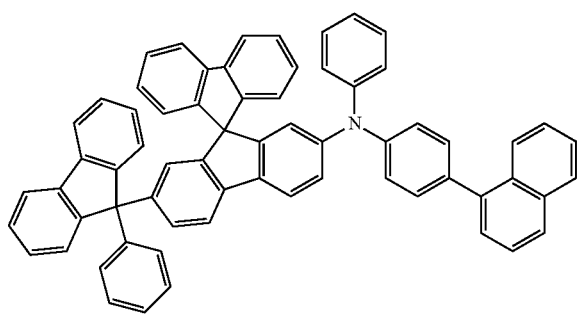

30
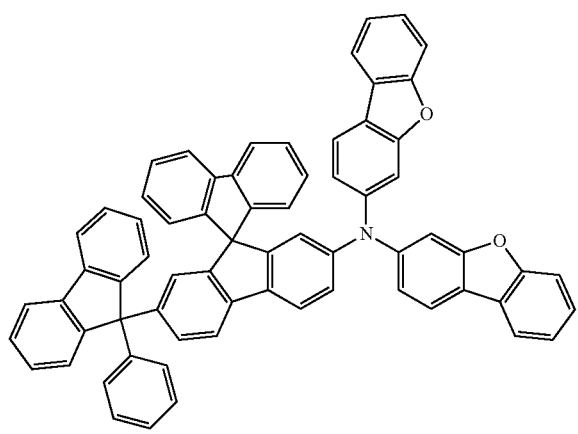
31
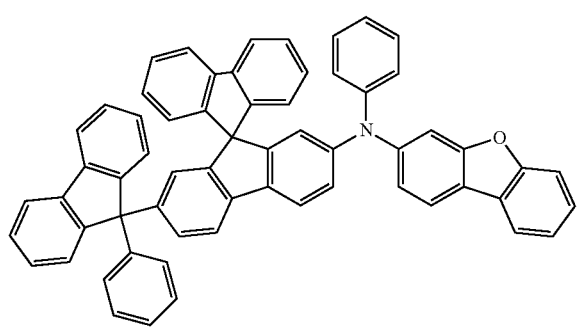
32
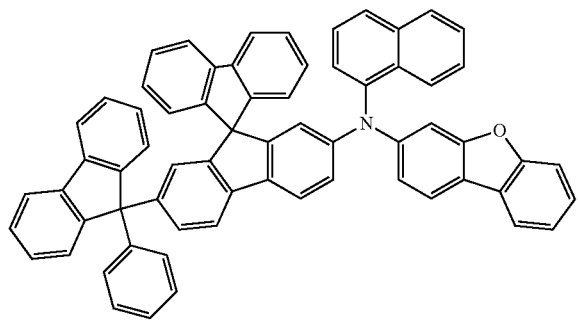
49
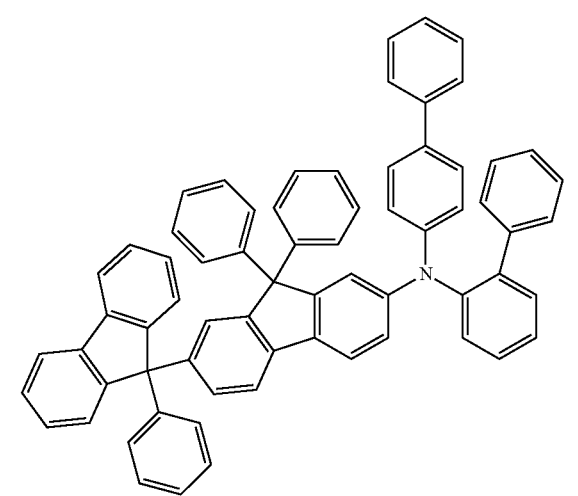
50
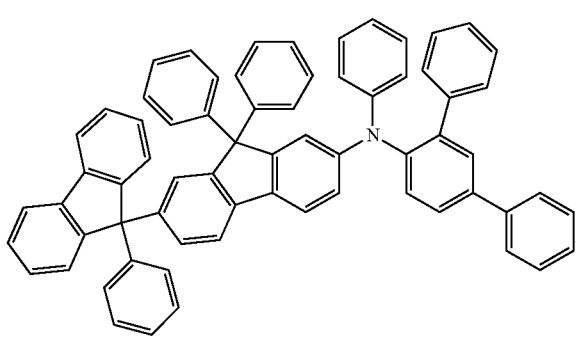
51
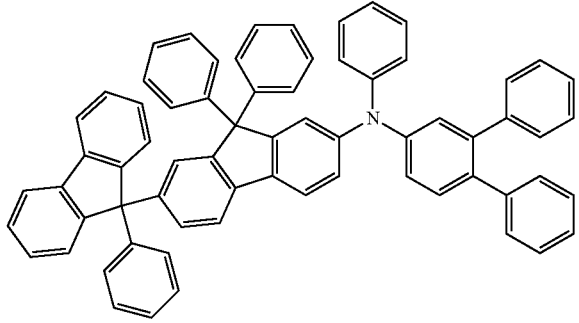
52
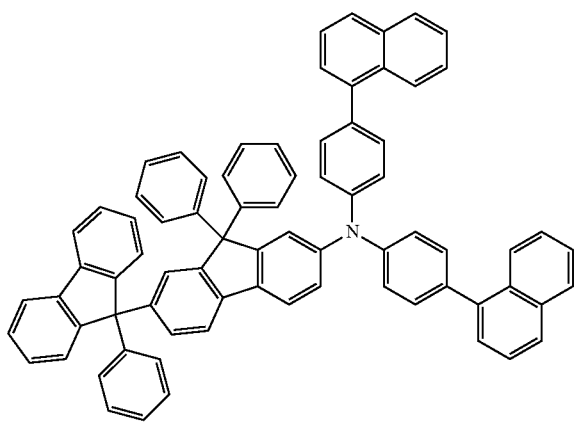
53
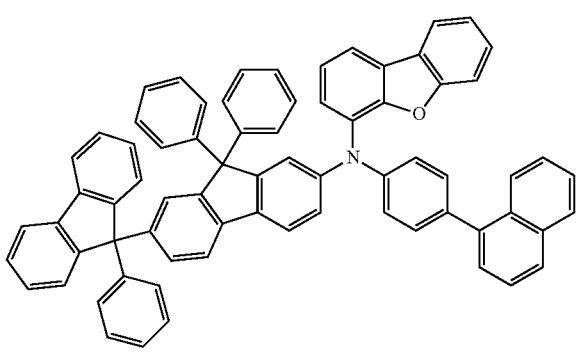

54
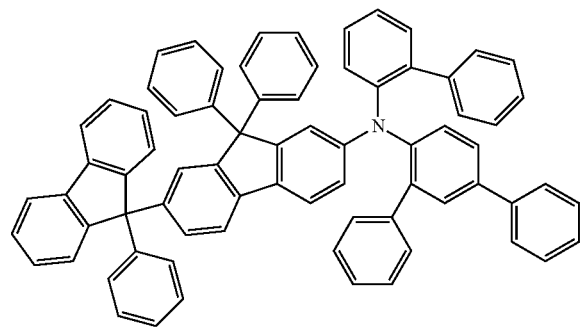
55
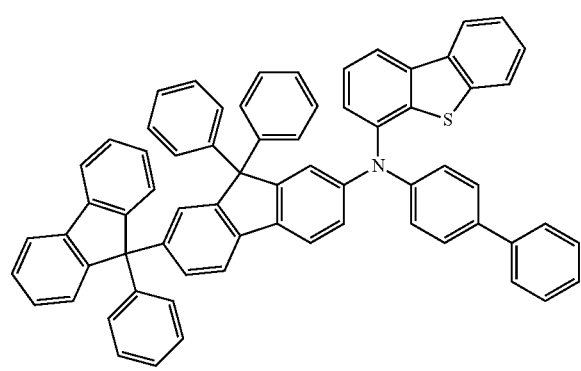
56
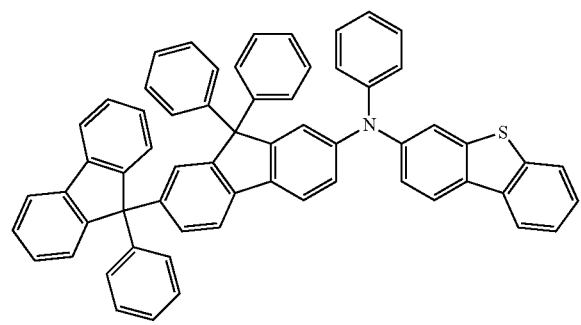
57
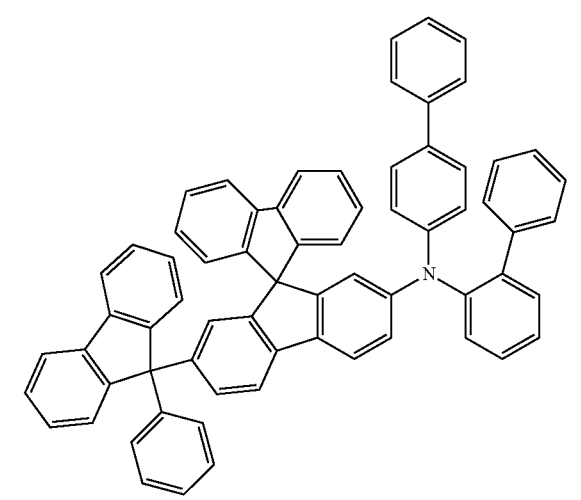
58
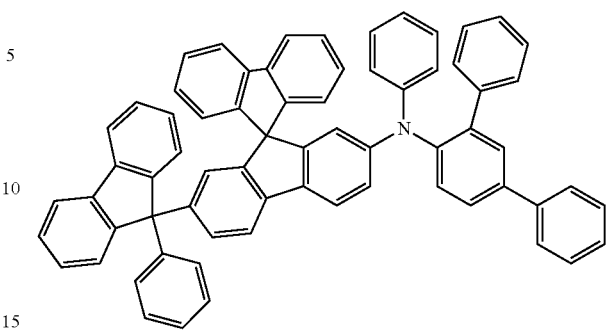
59
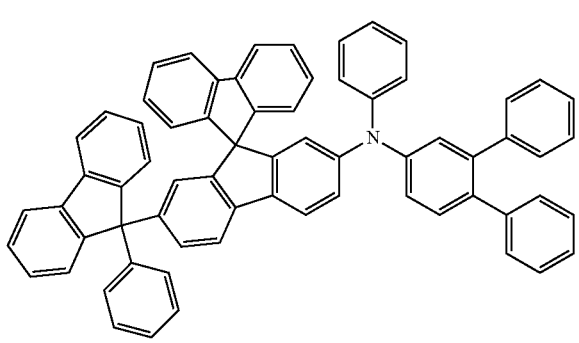
60
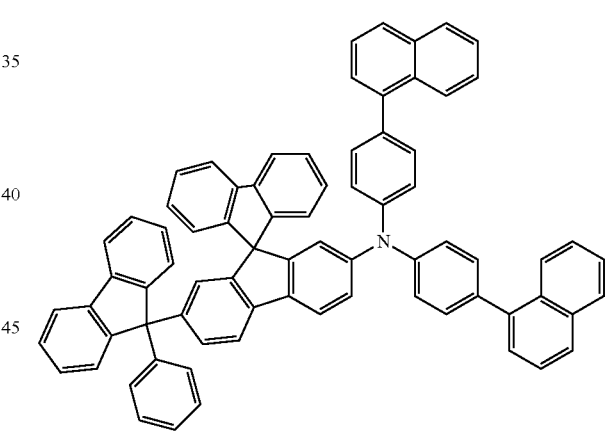
61
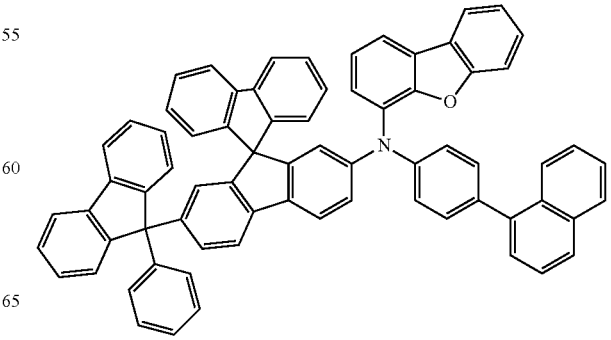

-continued
62
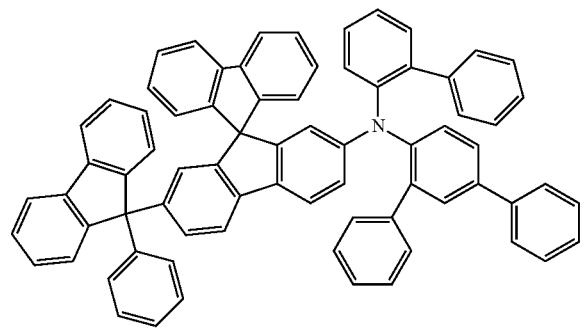
63
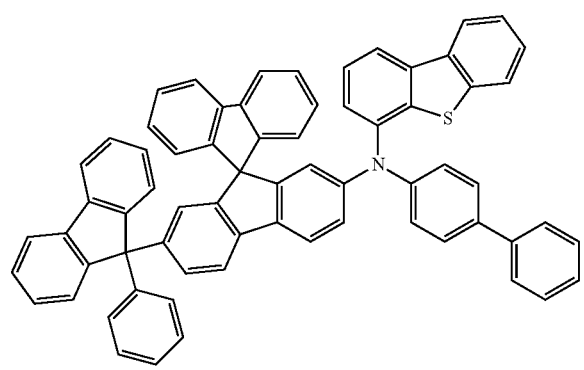
64
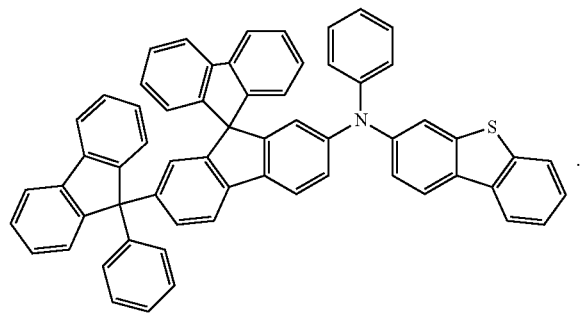
Compound Group 2
65
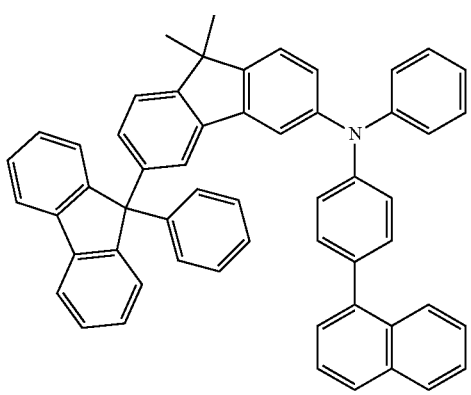
66
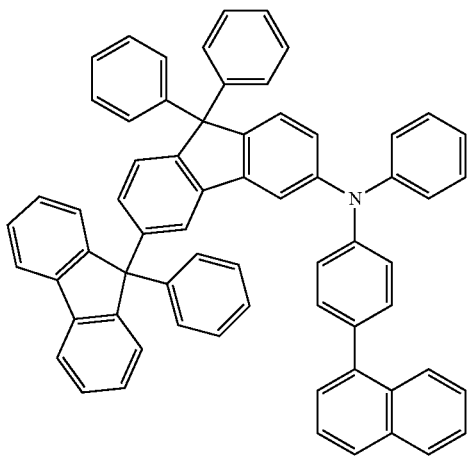
67
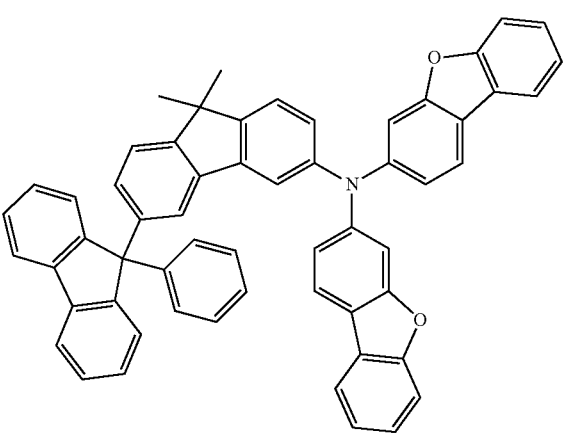
18. The organic electroluminescence device of claim 10, wherein the amine compound represented by Formula 1 is any one selected from the compounds represented by Compound Group 2 below: